US010130705B2

(12) United States Patent
Weiner et al.

(10) Patent No.: US 10,130,705 B2
(45) Date of Patent: Nov. 20, 2018

(54) VACCINES WITH INTERLEUKIN-33 AS AN ADJUVANT

(71) Applicants: The Trustees of the University of Pennsylvania, Philadelphia, PA (US); Inovio Pharmaceuticals, Inc., Plymouth Meeting, PA (US)

(72) Inventors: David Weiner, Merion, PA (US); Daniel Villarreal, San Diego, CA (US); Matthew Morrow, Bala Cynwyd, PA (US); Jian Yan, Wallingford, PA (US)

(73) Assignees: THE TRUSTEES OF THE UNIVERSITY OF PENNSYLVANIA, Philadelphia, PA (US); INOVIO PHARMACEUTICALS, INC., Plymouth Meeting, PA (US)

( * ) Notice: Subject to any disclaimer, the term of this patent is extended or adjusted under 35 U.S.C. 154(b) by 90 days.

(21) Appl. No.: 15/026,162

(22) PCT Filed: Oct. 2, 2014

(86) PCT No.: PCT/US2014/058727
§ 371 (c)(1),
(2) Date: Mar. 30, 2016

(87) PCT Pub. No.: WO2015/054012
PCT Pub. Date: Apr. 16, 2015

(65) Prior Publication Data
US 2016/0235838 A1 Aug. 18, 2016

Related U.S. Application Data

(60) Provisional application No. 61/887,502, filed on Oct. 7, 2013, provisional application No. 61/895,673, filed on Oct. 25, 2013.

(51) Int. Cl.
| C12N 15/67 | (2006.01) |
| C07K 14/54 | (2006.01) |
| A61K 38/20 | (2006.01) |
| C07K 14/005 | (2006.01) |
| C07K 14/025 | (2006.01) |
| C07K 14/445 | (2006.01) |
| C07K 14/35 | (2006.01) |
| A61K 39/39 | (2006.01) |
| A61K 38/16 | (2006.01) |
| A61K 39/015 | (2006.01) |
| A61K 39/04 | (2006.01) |
| A61K 39/12 | (2006.01) |
| A61K 39/21 | (2006.01) |
| C12N 7/00 | (2006.01) |
| C07K 14/16 | (2006.01) |
| A61K 39/00 | (2006.01) |

(52) U.S. Cl.
CPC ............ *A61K 39/39* (2013.01); *A61K 38/162* (2013.01); *A61K 38/164* (2013.01); *A61K 38/20* (2013.01); *A61K 39/015* (2013.01); *A61K 39/04* (2013.01); *A61K 39/12* (2013.01); *A61K 39/21* (2013.01); *C07K 14/54* (2013.01); *C12N 7/00* (2013.01); *A61K 39/0011* (2013.01); *A61K 2039/53* (2013.01); *A61K 2039/54* (2013.01); *A61K 2039/55527* (2013.01); *A61K 2039/57* (2013.01); *A61K 2039/572* (2013.01); *A61K 2039/575* (2013.01); *A61K 2039/585* (2013.01); *C07K 14/005* (2013.01); *C07K 14/025* (2013.01); *C07K 14/16* (2013.01); *C07K 14/35* (2013.01); *C07K 14/445* (2013.01); *C12N 2710/20034* (2013.01); *C12N 2740/16034* (2013.01); *C12N 2760/10034* (2013.01); *Y02A 50/412* (2018.01)

(58) Field of Classification Search
None
See application file for complete search history.

(56) References Cited

U.S. PATENT DOCUMENTS

| 8,119,771 B2 | 2/2012 | Martin |
| 2014/0099280 A1 | 4/2014 | Girard et al. |

FOREIGN PATENT DOCUMENTS

| EP | 2021799 A2 | 2/2009 |
| JP | 2010-208985 A | 9/2010 |
| JP | 2012-509340 A | 4/2012 |
| JP | 2013-517800 A | 5/2013 |
| WO | 2007143295 A2 | 12/2007 |
| WO | 2008066443 A1 | 6/2008 |
| WO | 2008/132709 A1 | 11/2008 |
| WO | 2008132709 A1 | 11/2008 |
| WO | 2010/059732 A1 | 5/2010 |
| WO | 2011/031600 A1 | 3/2011 |
| WO | 2011/094358 A1 | 4/2011 |
| WO | 2012113927 A1 | 8/2012 |

(Continued)

OTHER PUBLICATIONS

Bonilla et al., "The Alarmin Interleukin-33 Drives Protective Antiviral CD8+ T Cell Response" Science 335:984-989 (2012).

(Continued)

*Primary Examiner* — Joanne Hama
*Assistant Examiner* — Fozia Hamud
(74) *Attorney, Agent, or Firm* — Riverside Law LLP

(57) ABSTRACT

Disclosed herein is a vaccine comprising an antigen and IL-33. Also disclosed herein is a method for increasing an immune response in a subject in need thereof. Further disclosed herein is a method for treating cancer in a subject in need thereof. The methods may comprise administering the vaccine to the subject.

22 Claims, 39 Drawing Sheets

Specification includes a Sequence Listing.

(56) References Cited

FOREIGN PATENT DOCUMENTS

| WO | 2012116810 A1 | 9/2012 |
|---|---|---|
| WO | 2013113502 A1 | 8/2013 |

OTHER PUBLICATIONS

Lauren A Hirao, "Enhancement of immune responses to DNA vaccines" (Jan. 1, 2010); pp. 1-2. http://repository.upenn.edu/dissertations/AAI3414202.

Villarreal et al., "Alarmin IL-33 acts as an immunoadjuvant to enhance antigen-specific tumor immunity" Cancer Res 74 (6):1789-800 (2014).

Tu et al., "Molecular adjuvant interleukin-33 enhances the antifertility effect of Lagurus lagurus zona pellucida 3 DNA vaccine administered by the mucosal route" Braz J Med Biol Res 46(12):1064-1073 (2013).

Wieking et al., "A non-oncogenic HPV 16 E6/E7 vaccine enhances treatment of HPV expressing tumors" Cancer Gene Ther 19:667-674 (2012).

John et al., "Antibodies to the Plasmodium falciparum antigens circumsporozoite protein, thrombospondin-related adhesive protein, and liver-stage antigen 1 vary by ages of subjects and by season in a highland area of Kenya" Infect Immun 71(8):4320-4325 (2003).

Lozes et al., "Immunogenicity and efficacy of a tuberculosis DNA Vaccine encoding the components of the secreted antigen 85 complex" Vaccine 15(8):830-3 (1997).

Rodriguez et al., "DNA immunization: ubiquitination of a viral protein enhances cytotoxic T-lymphocyte induction and antiviral protection but abrogates antibody induction" J Virol 71(11):8497-8503 (1997).

Batanova et al., "Cell surface expression of a chimeric protein containing mouse immunoglobulin G1 Fc domain and its immunological property" J Vet Med Sci 68(1):87-90 (2006).

Mallilankaraman et al., "A DNA Vaccine against Chikungunya Virus is Protective in Mice and Induces Neutralizing Antibodies in Mice and Nonhuman Primates," 2011, PLoS Negl Trop Dis 5(1):e928.

Yan et al., "Immunogenicity of a novel engineered HIV-1 clade C synthetic consensus-based envelope DNA vaccine," 2011, Vaccine 29(41):7173-81.

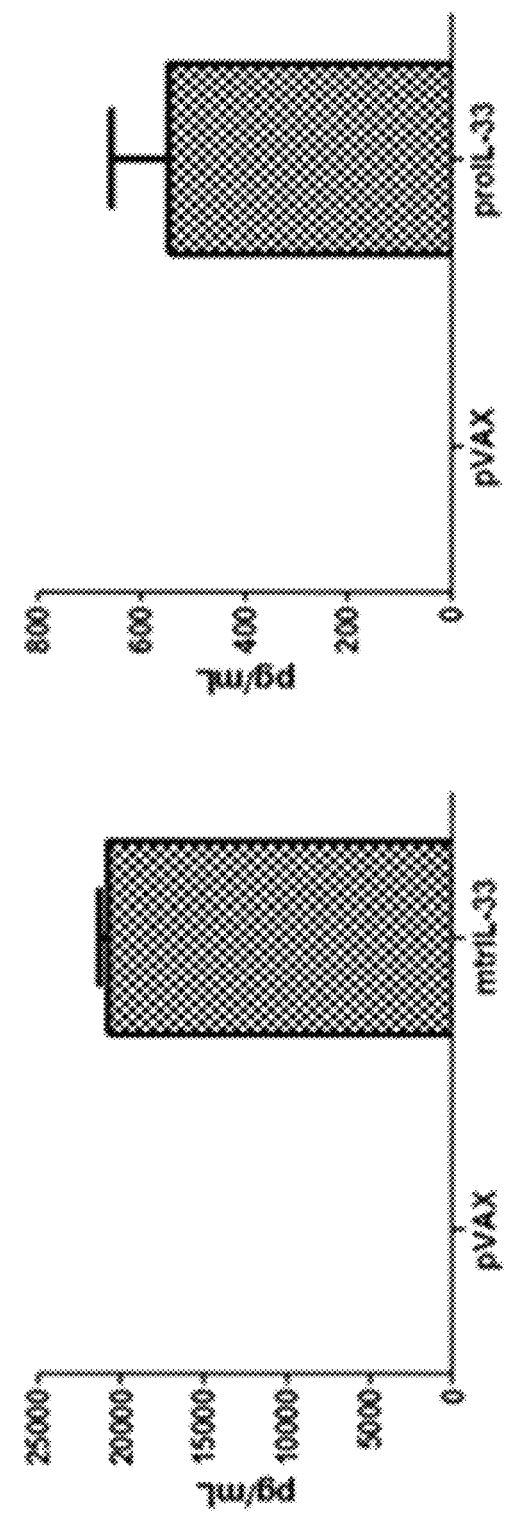
FIG. 1 (con't)

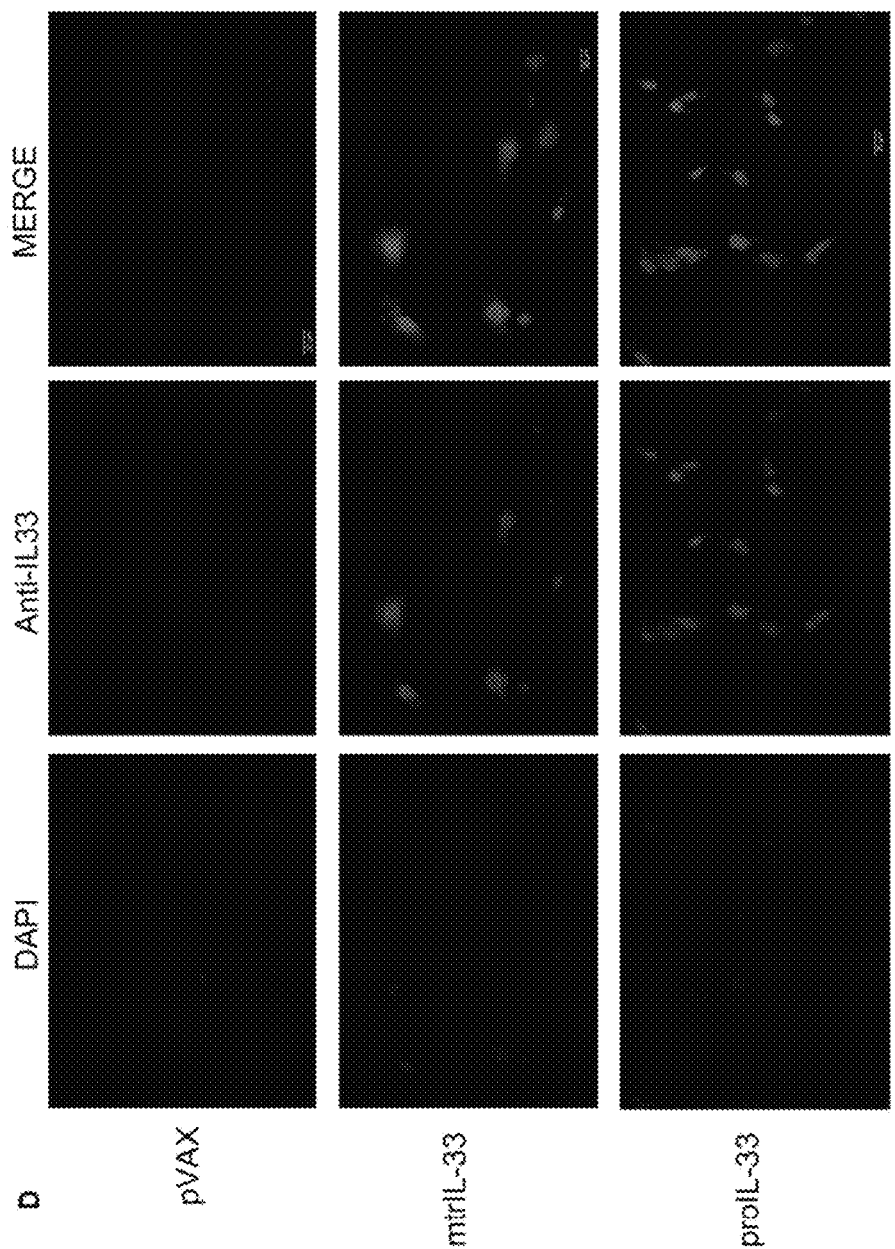
FIG. 1 (con't)

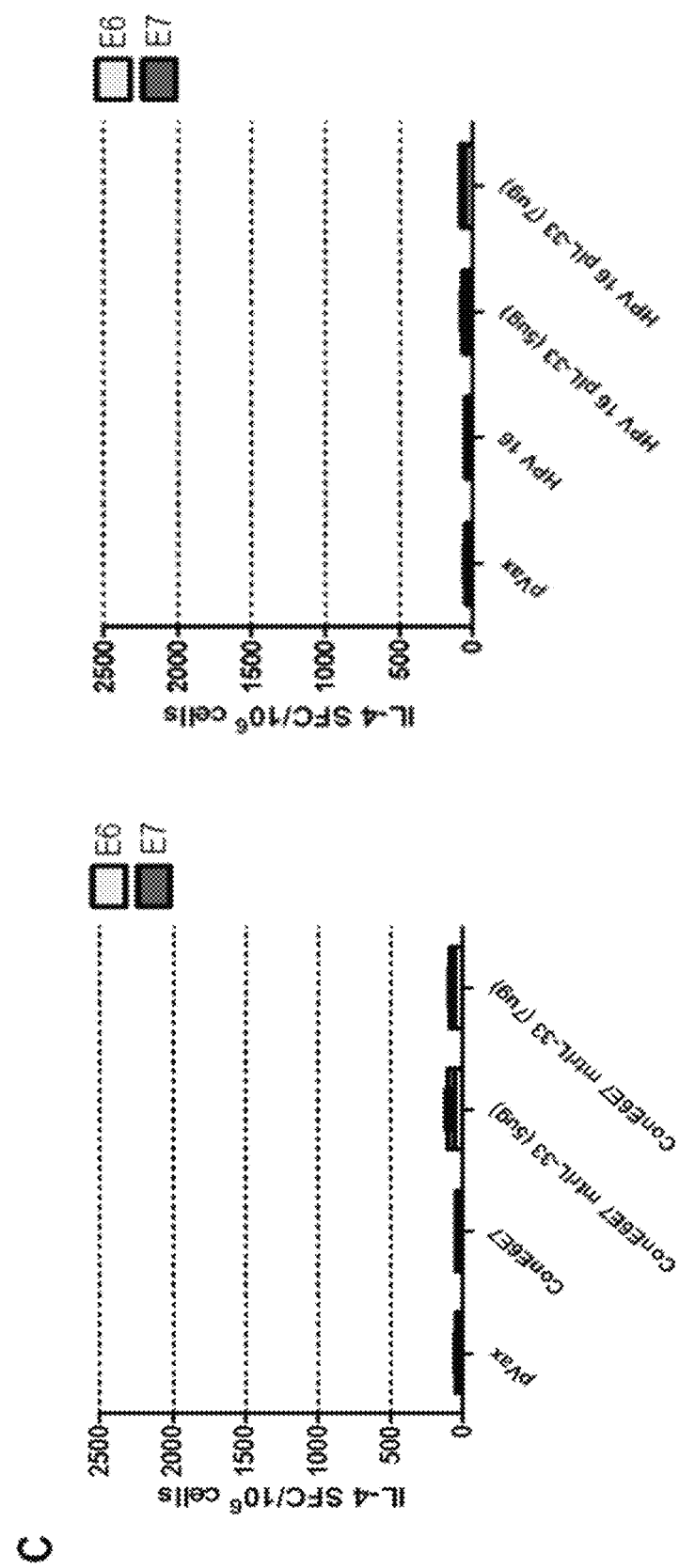
FIG. 2 (con't)

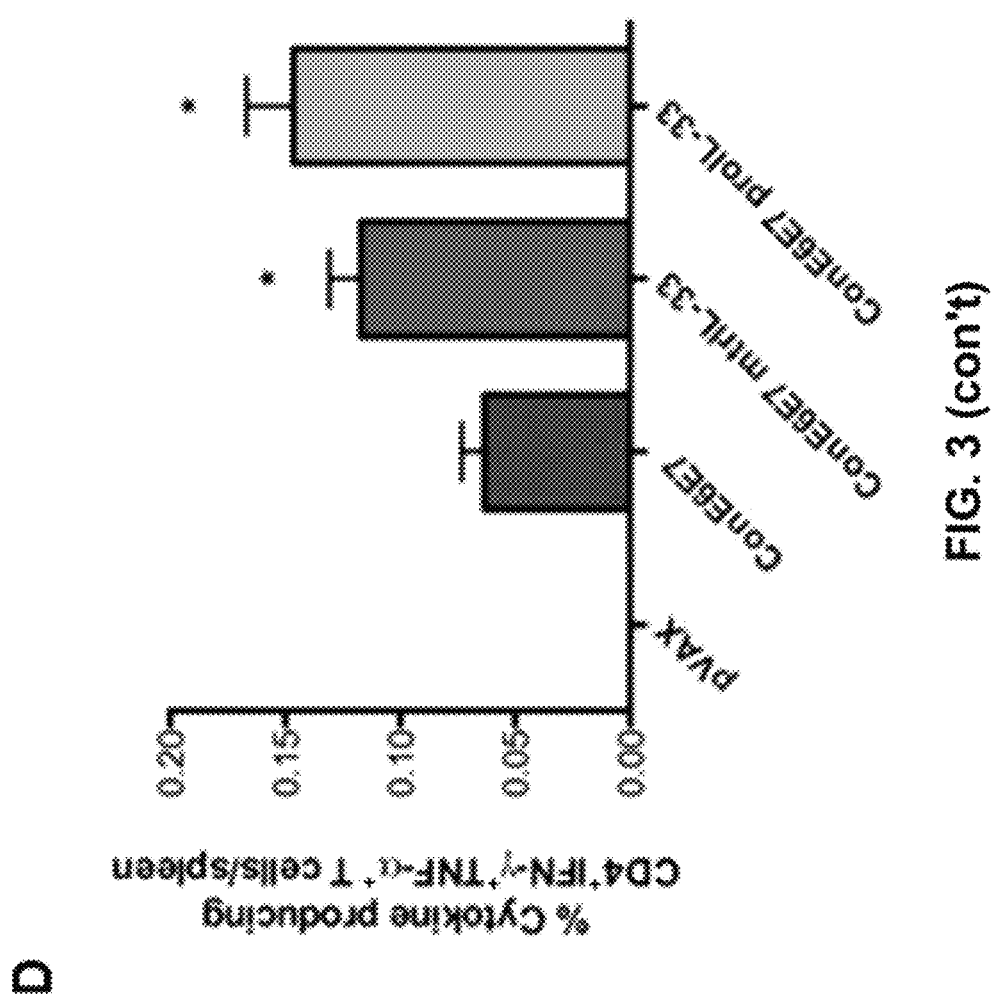
FIG. 3 (con't)

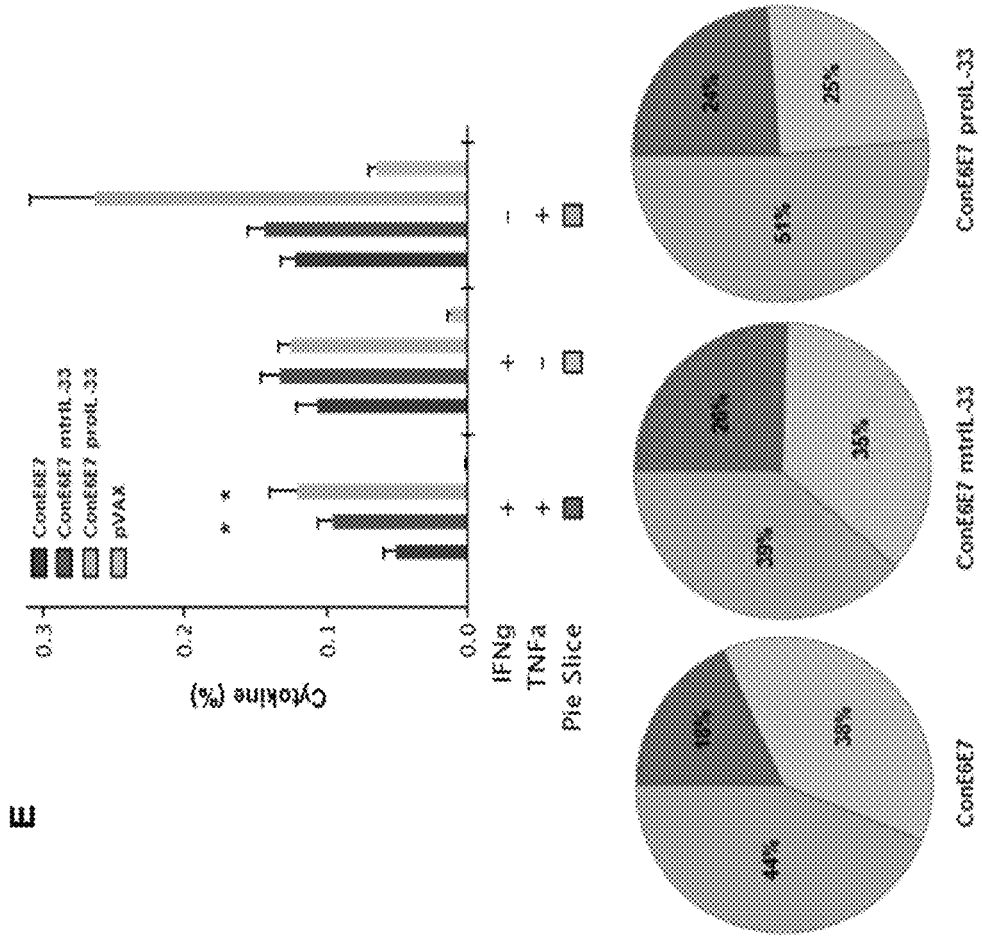
FIG. 3 (con't)

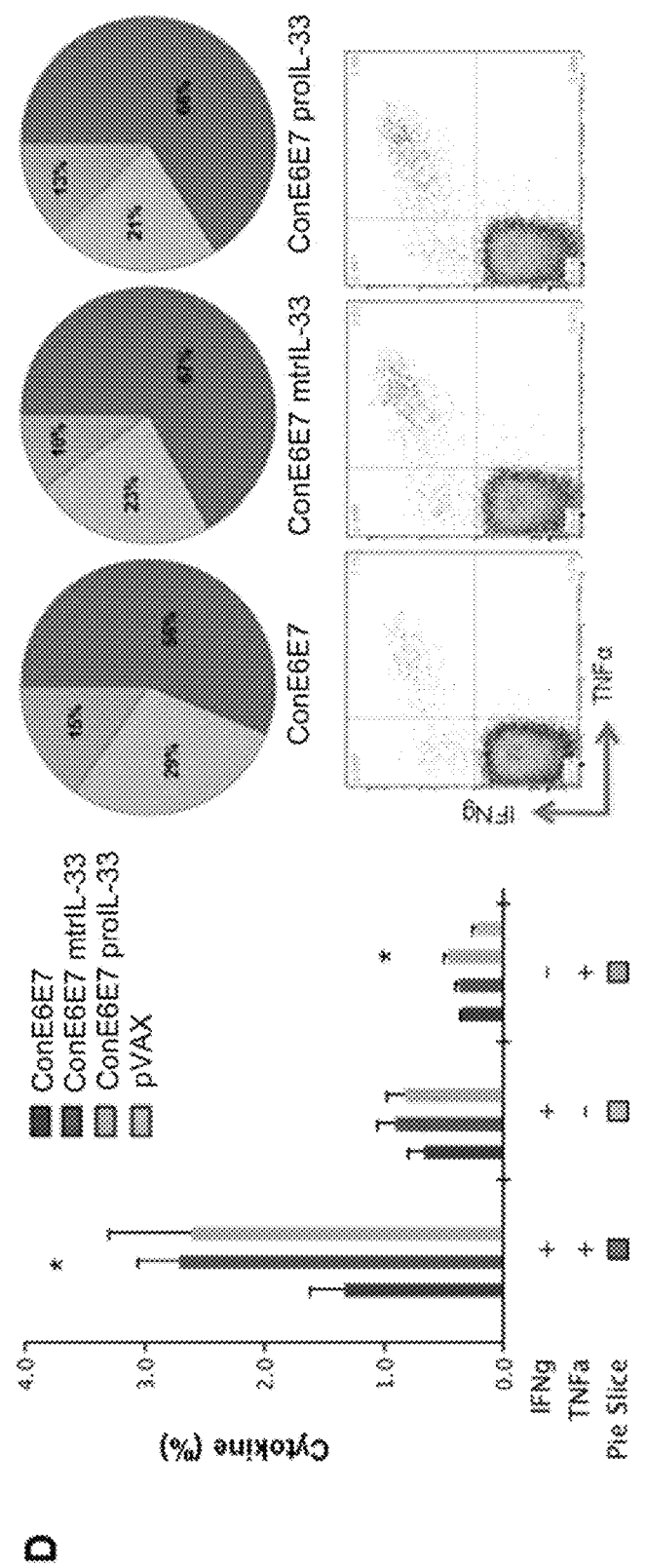
FIG. 4 (con't)

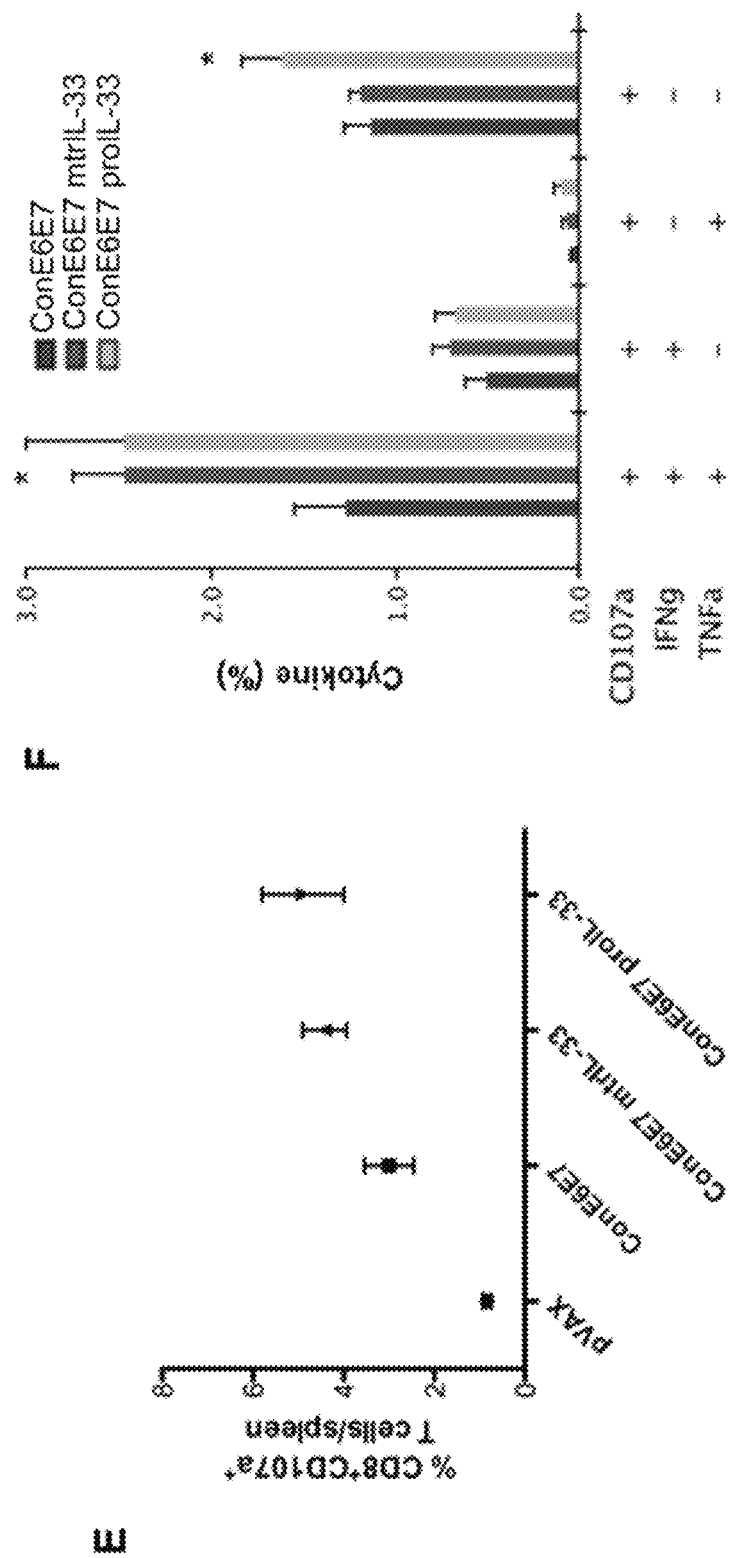
FIG. 4 (con't)

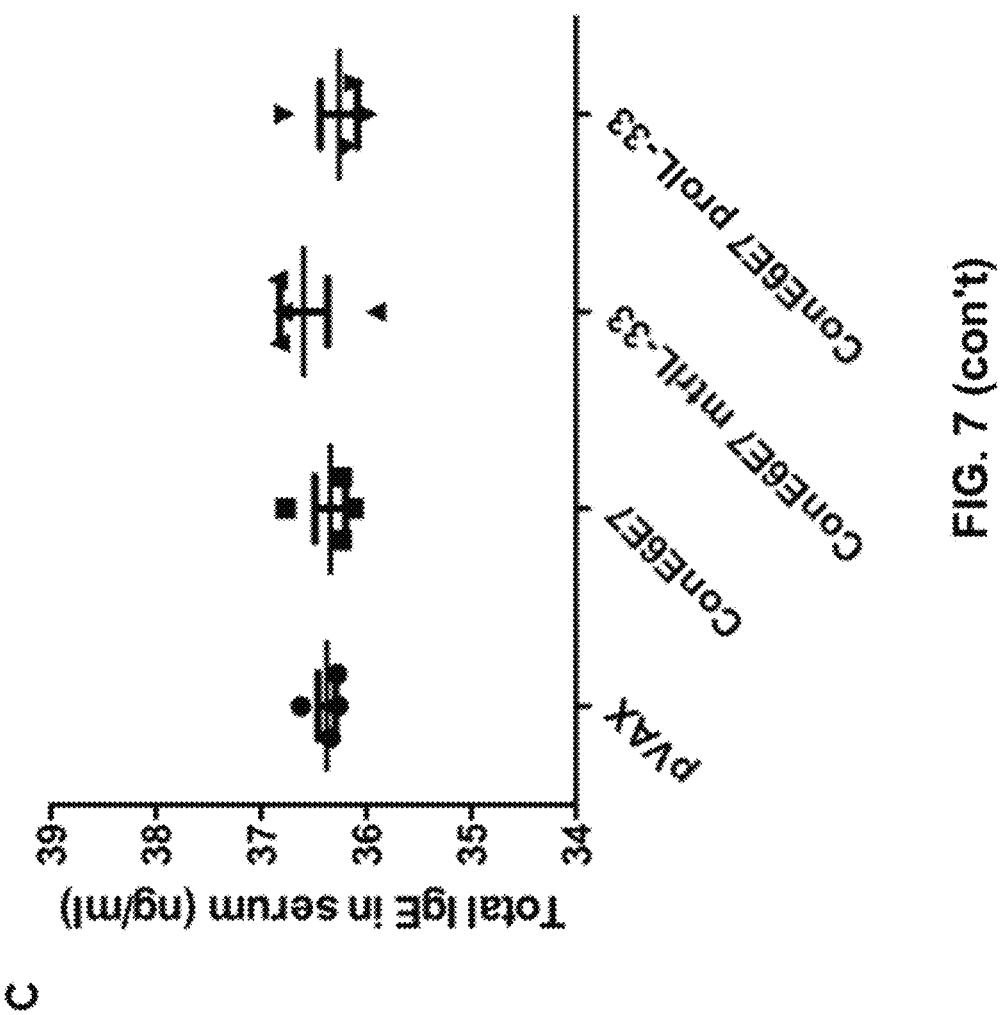
FIG. 7 (con't)

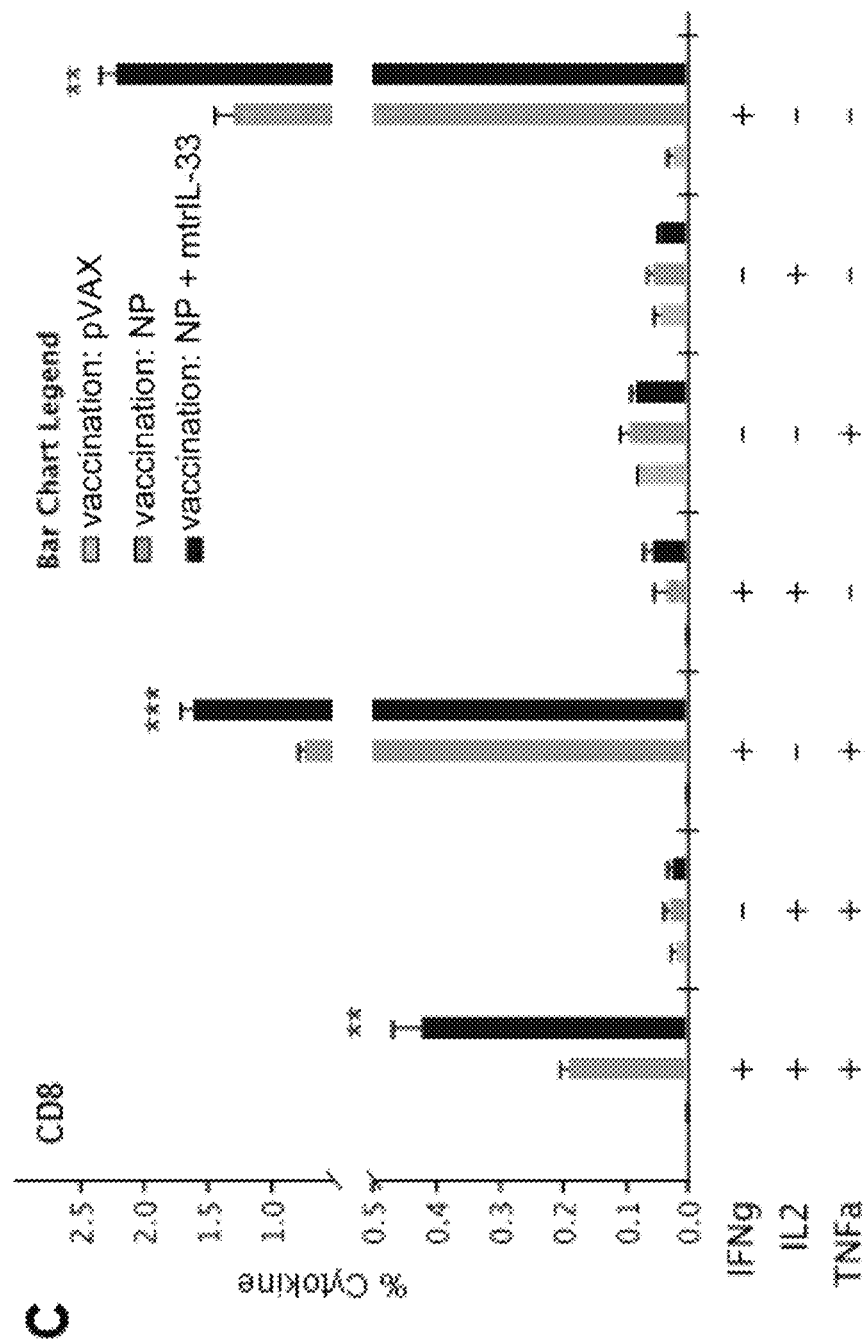
FIG. 12 (con't)

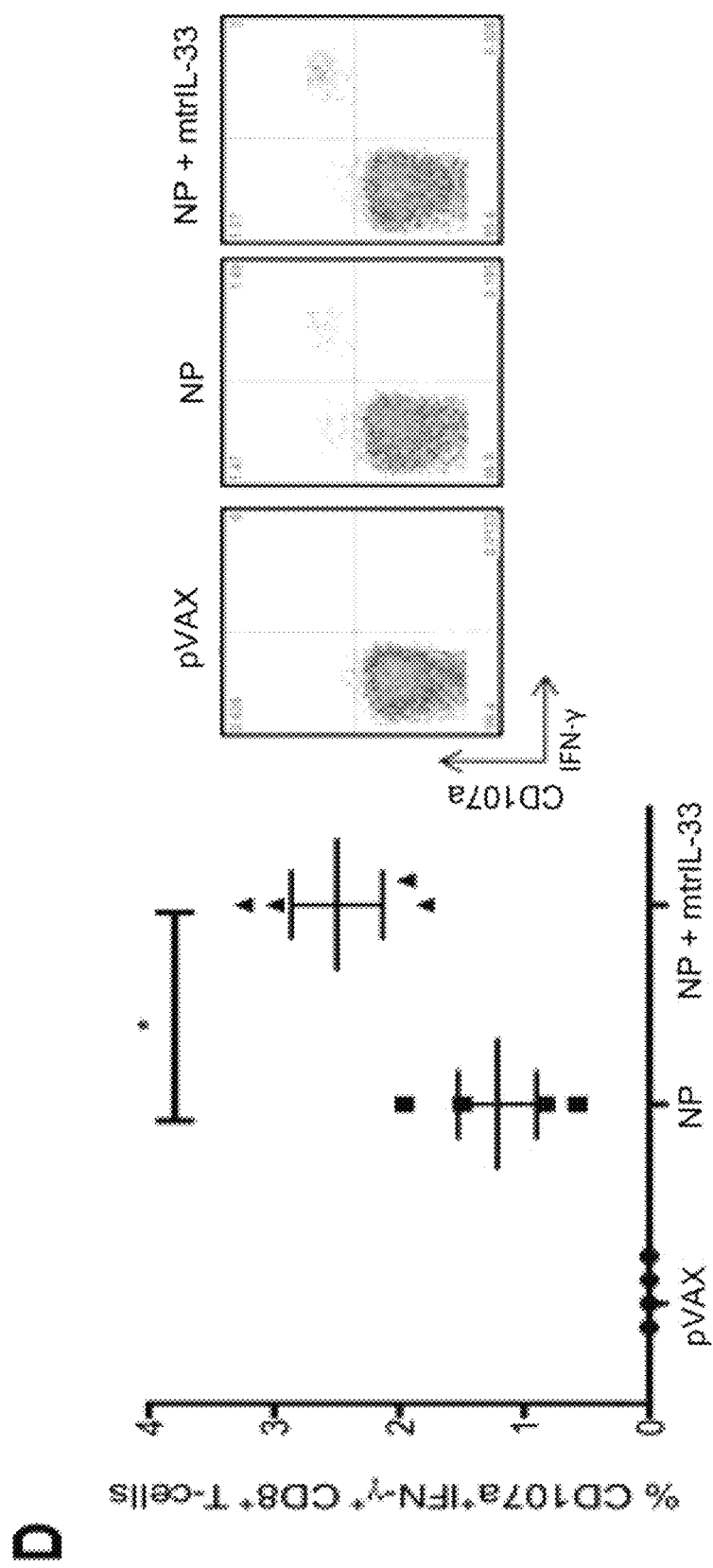
FIG. 12 (con't)

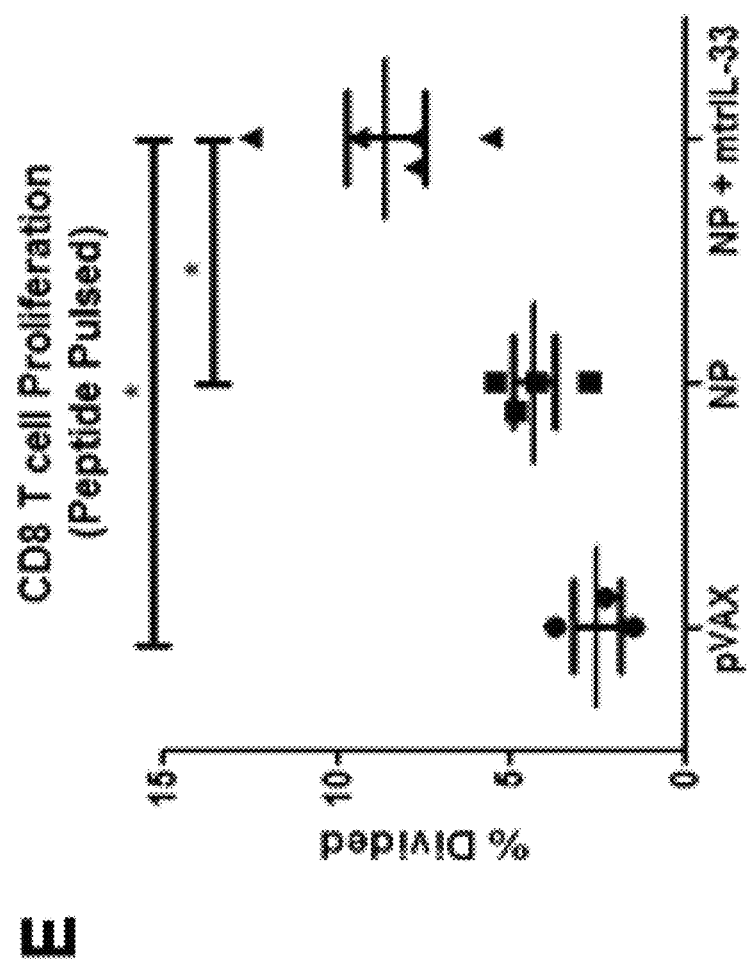
FIG. 12 (con't)

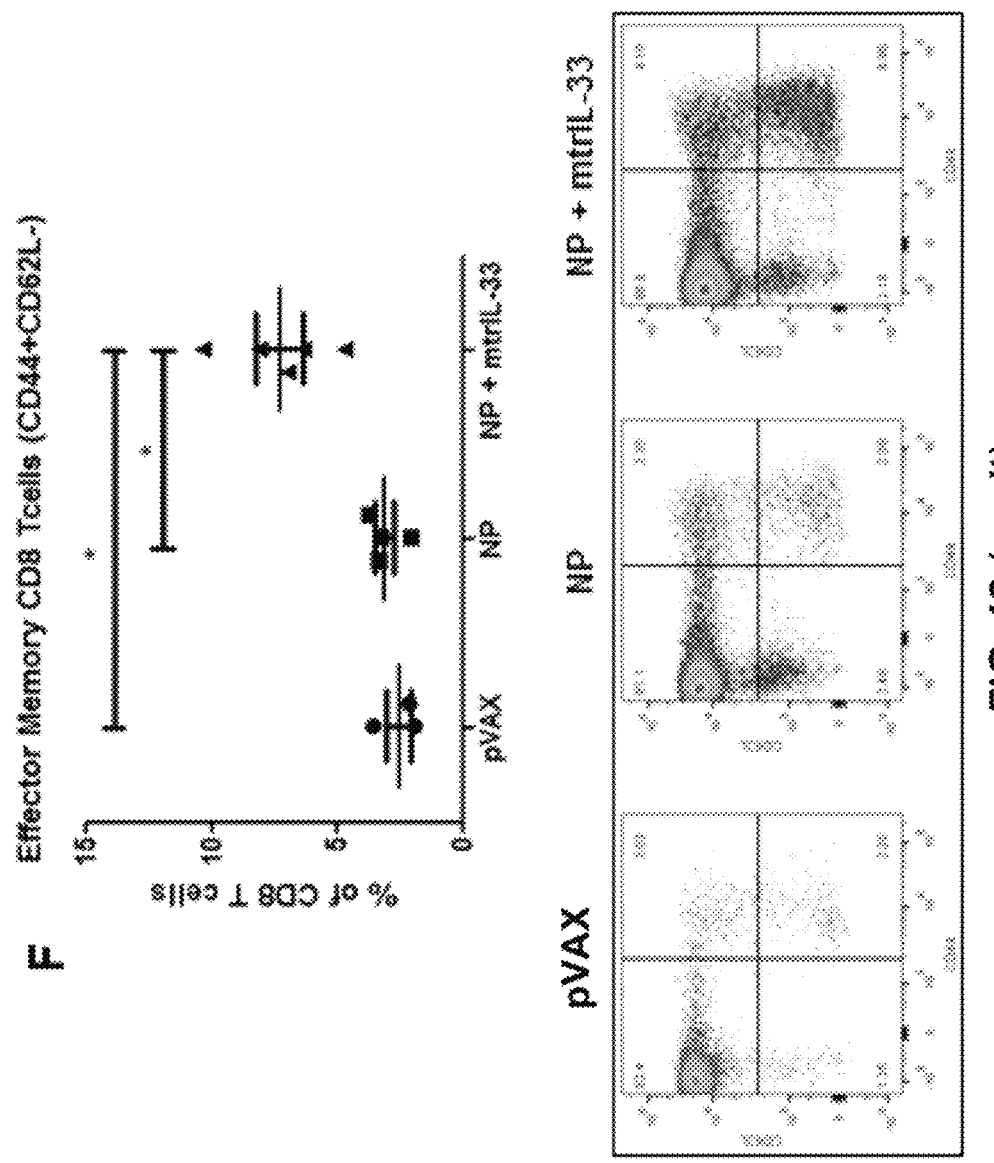
FIG. 12 (con't)

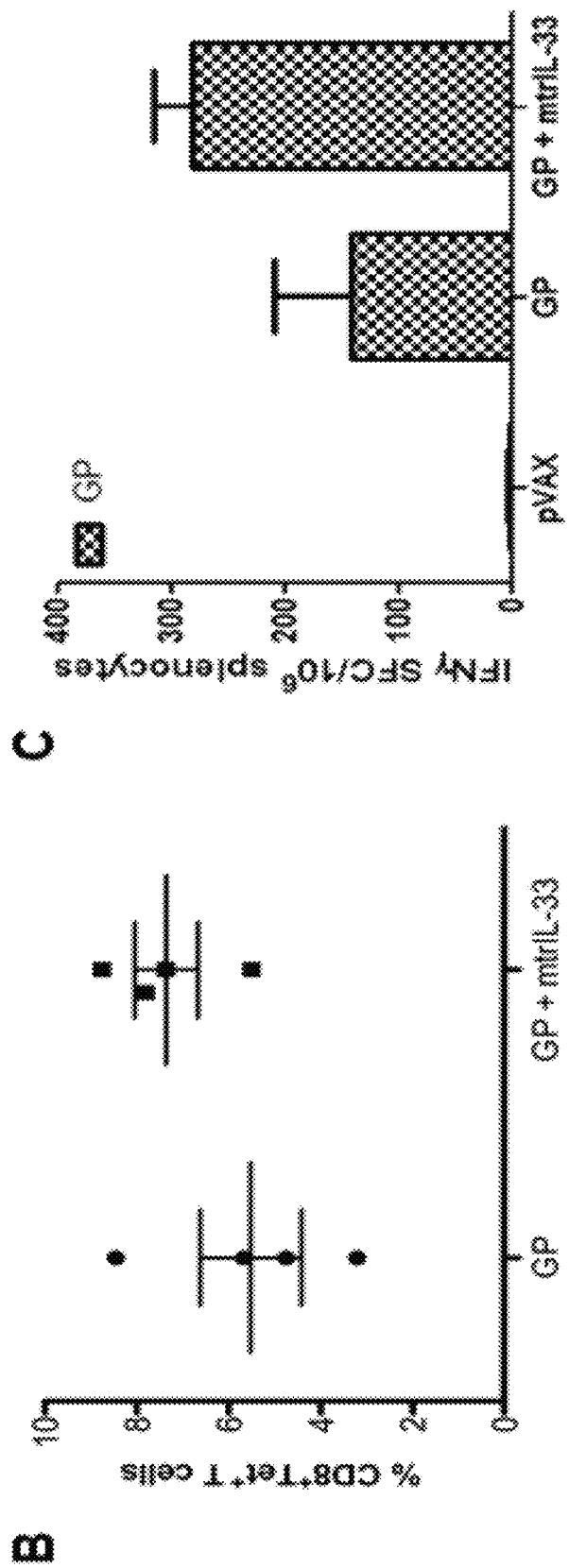
FIG. 13 (con't)

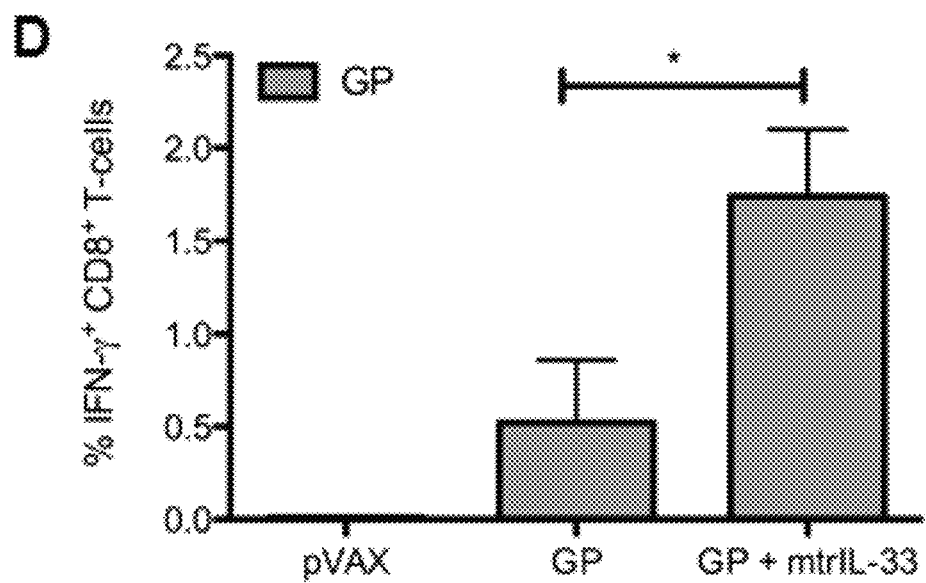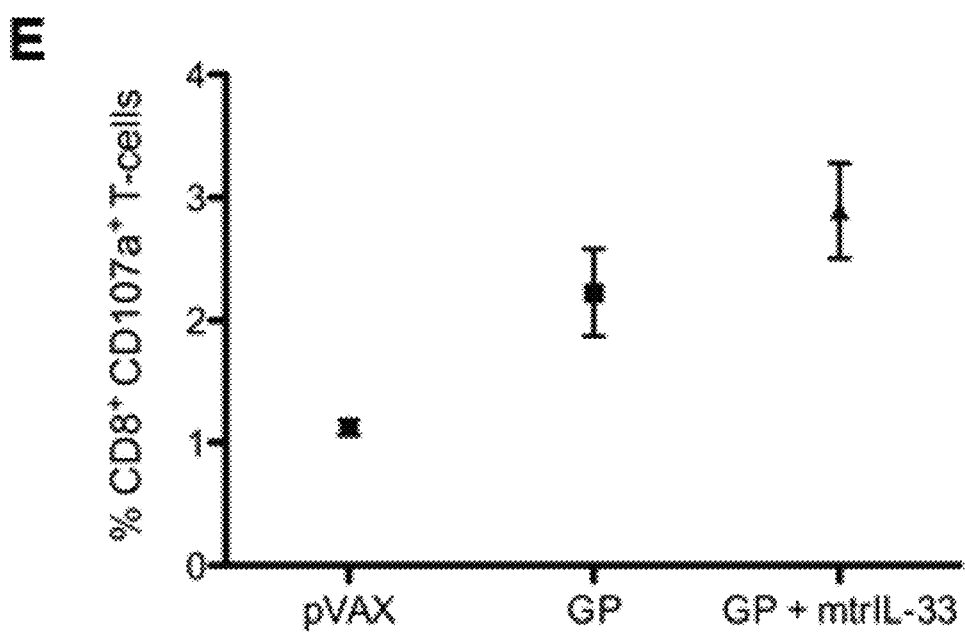
FIG. 13 (con't)

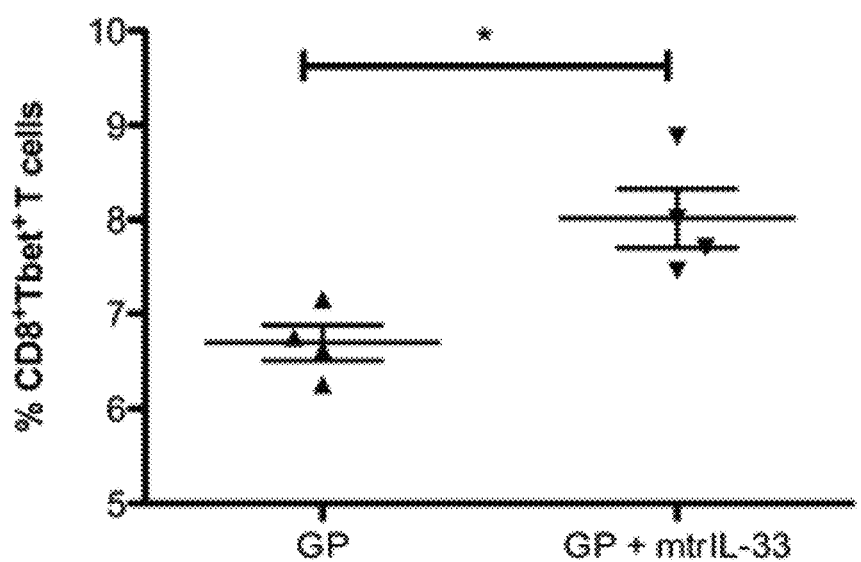
FIG. 13 (con't)

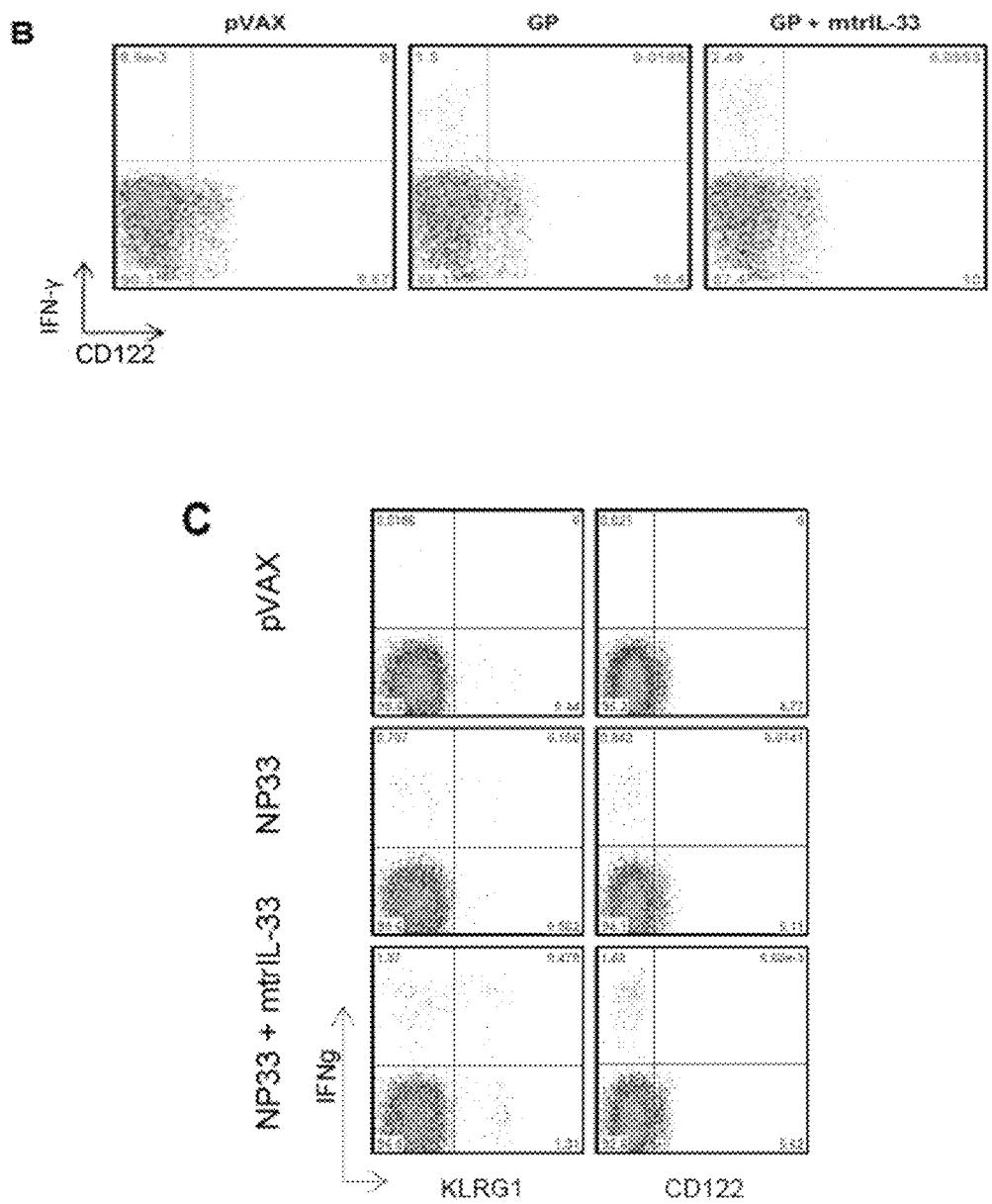
FIG. 15 (con't)

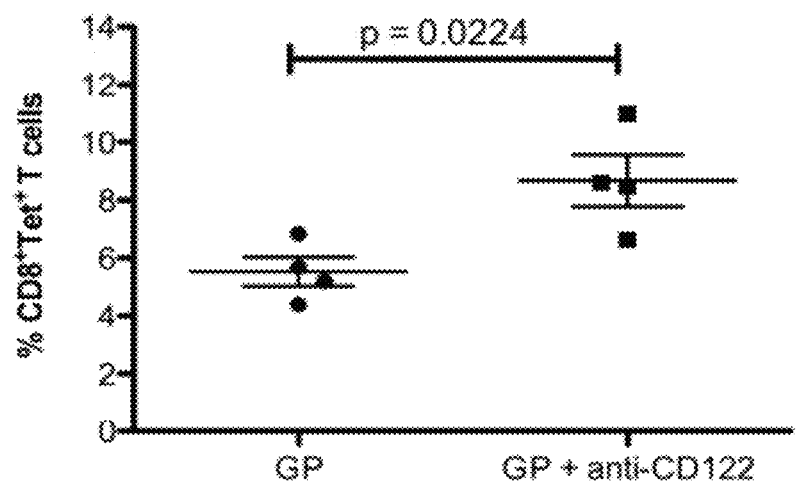
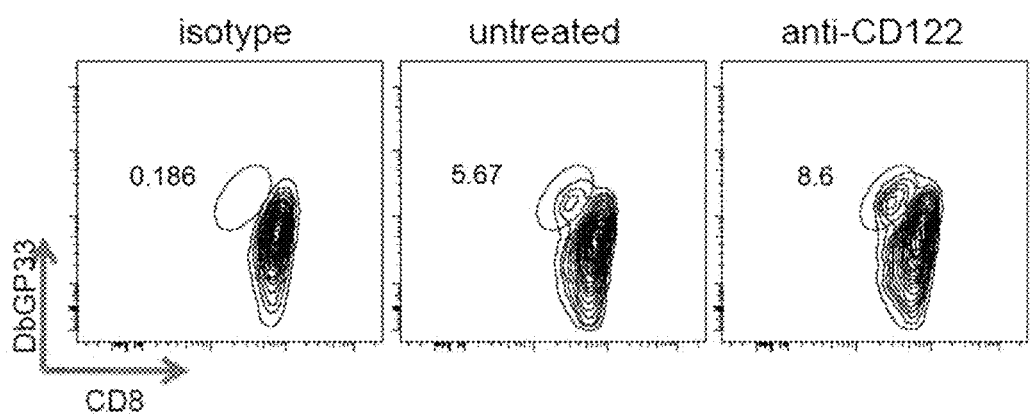
FIG. 16 (con't)

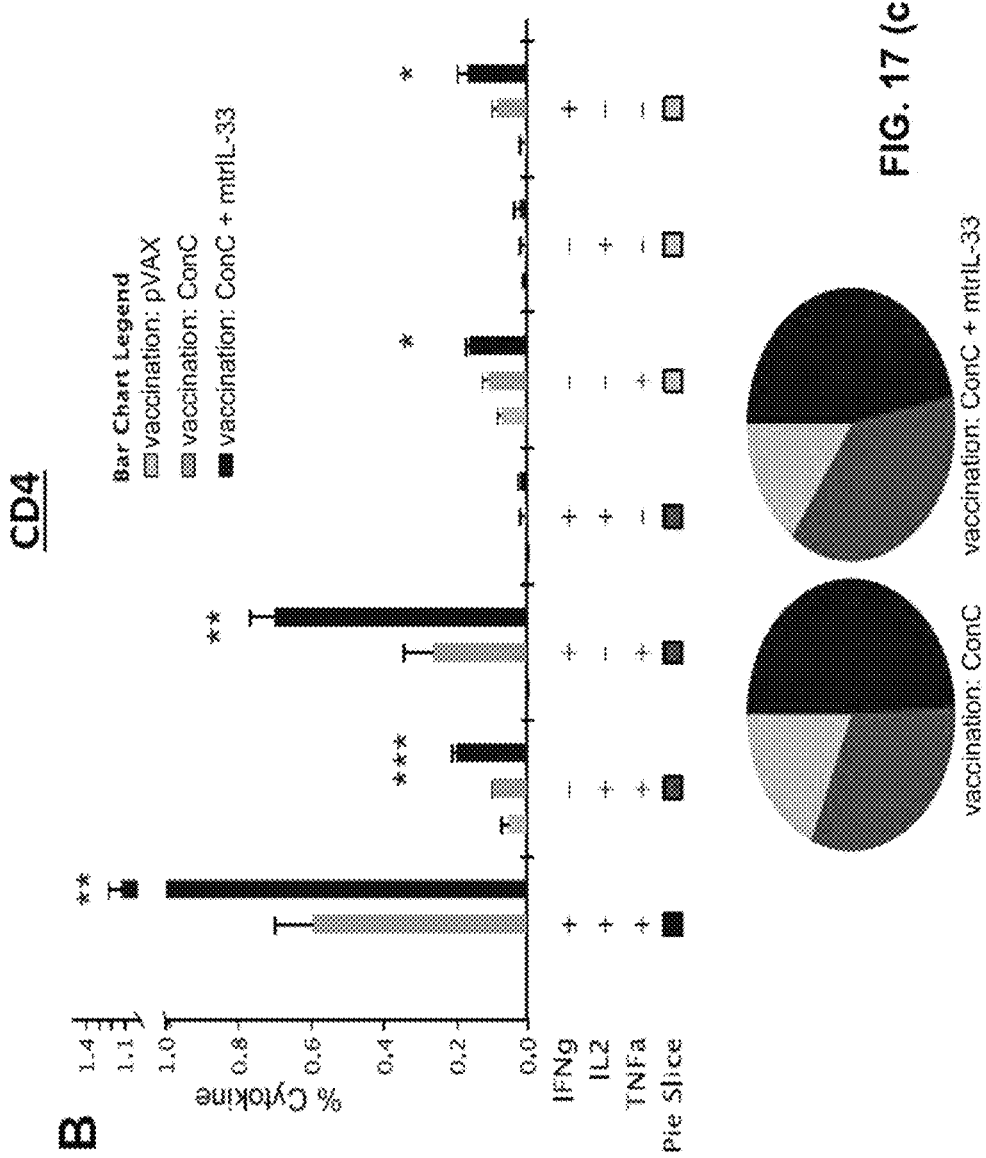
FIG. 17 (con't)

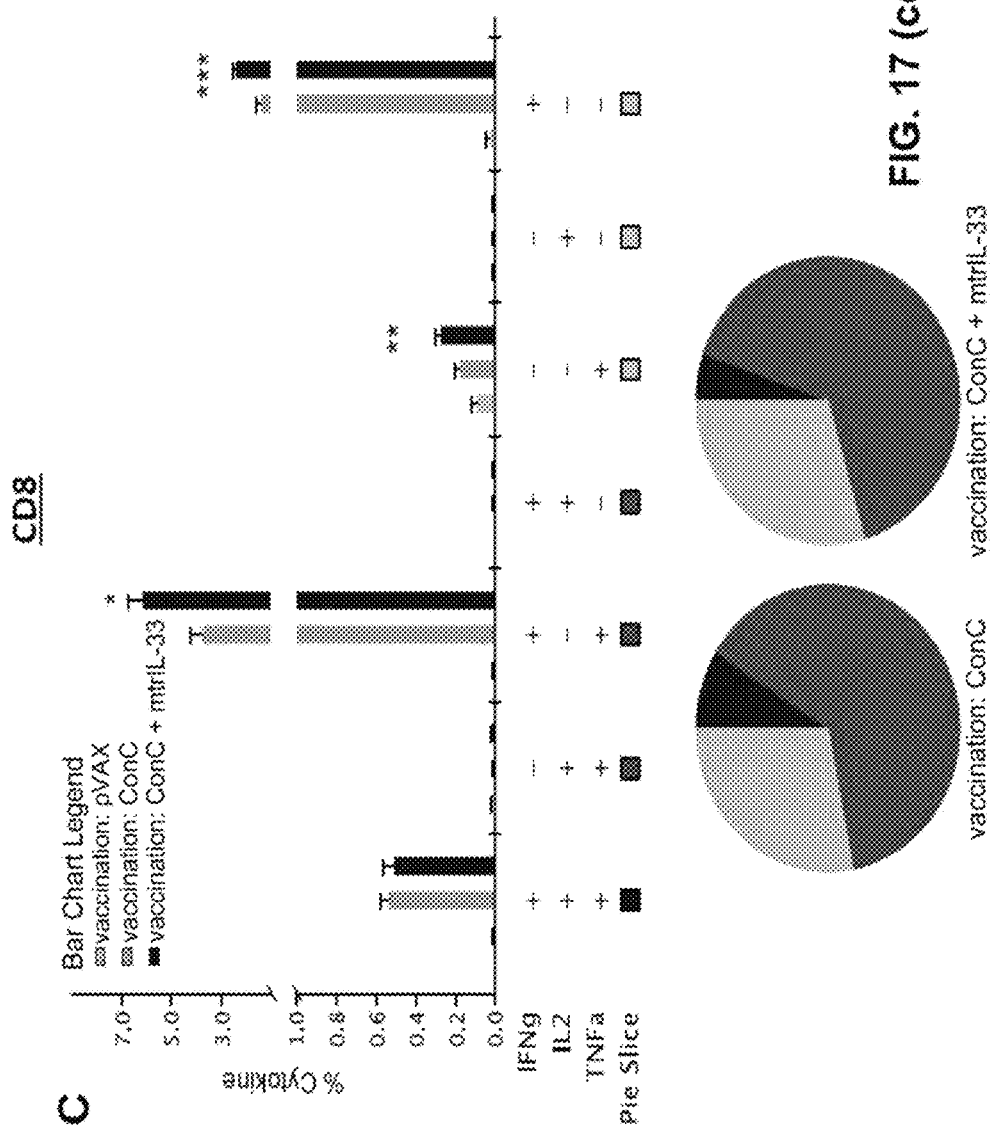

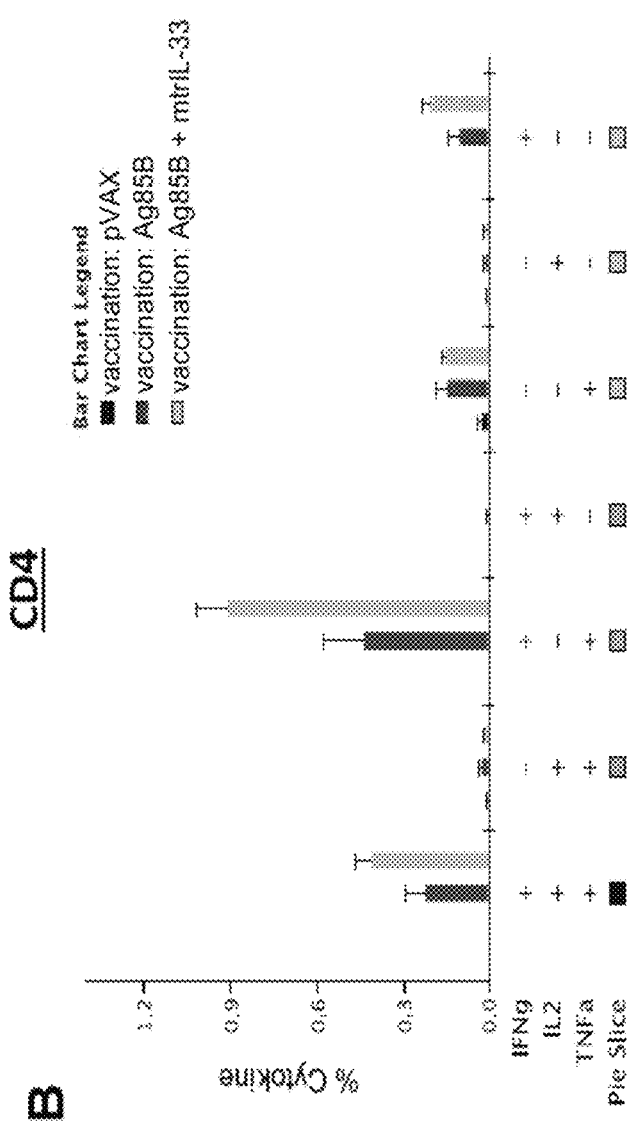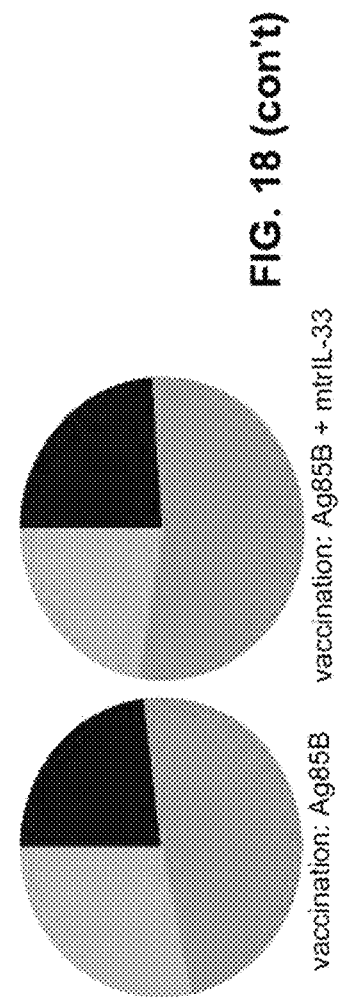
FIG. 18 (con't)

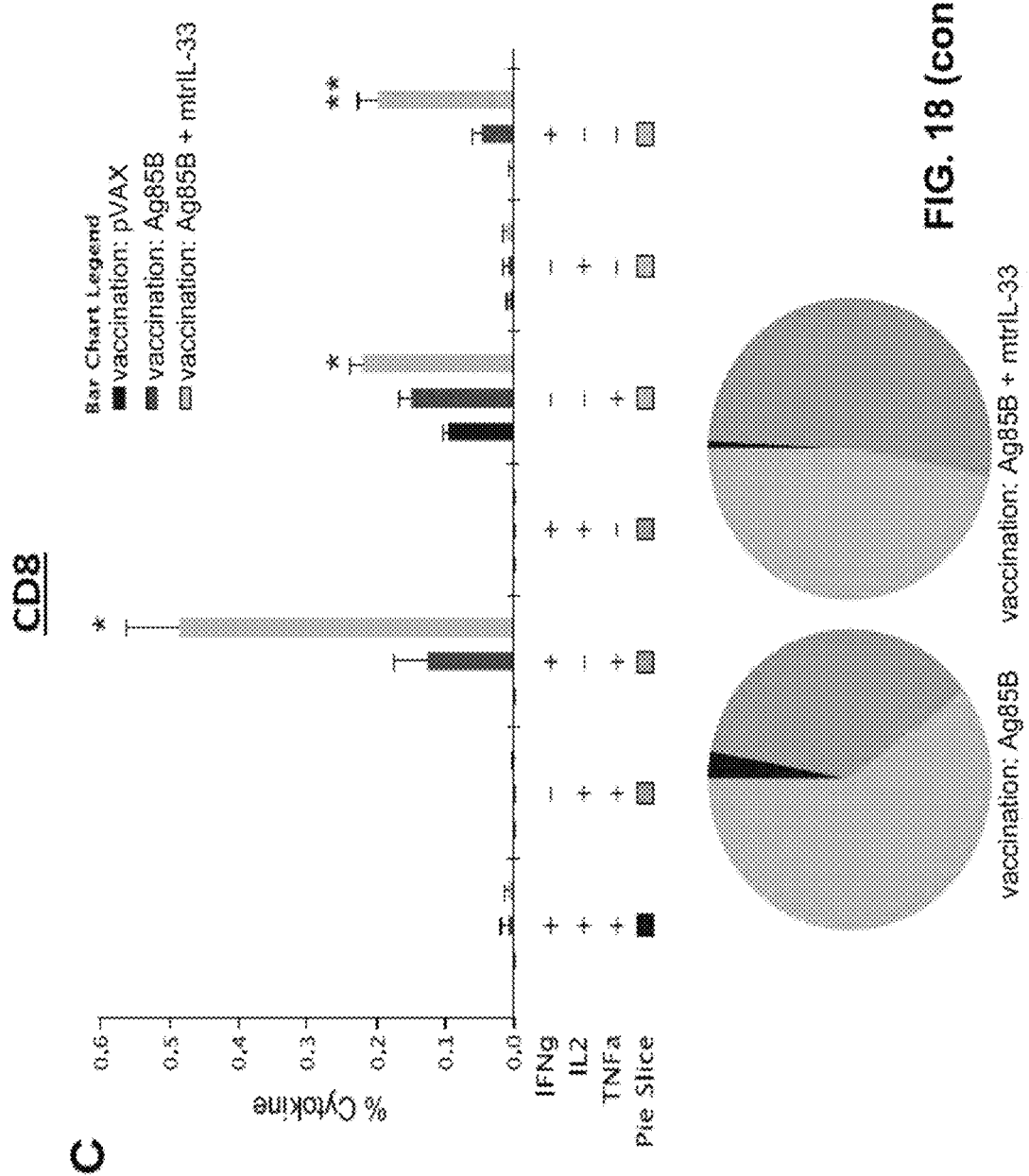
FIG. 18 (con't)

SEQUENCE LISTING

<160> NUMBER OF SEQ ID NOS: 9

<210> SEQ ID NO 1
<211> LENGTH: 531
<212> TYPE: DNA
<213> ORGANISM: Artificial Sequence
<220> FEATURE:
<223> OTHER INFORMATION: Optimized HmtrIL-33 DNA sequence

<400> SEQUENCE: 1
atggactgga cctggattct gttcctggtc gccgccgcaa ctagggtgca ctcatcaatc 60
actggcattt cccccatcac tgaatatctg gcctctctga gtacttacaa cgatcagagc 120
atcaccttcg ctctggagga cgaatcctac gagatctacg tggaagacct gaagaaagat 180
gagaagaaag acaaggtcct gctgtcctac tatgagtctc agcacccatc aaatgaaagc 240
ggcgacgggg tggatgggaa aatgctgatg gtcaccctgt ctcccacaaa ggacttttgg 300
ctgcatgcaa acaacaagga gcactccgtg gaactgcata agtgcgagaa acccctgcct 360
gatcaggcct tctttgtgct gcacaacatg catagtaatt gcgtctcatt cgagtgtaag 420
accgatcccg gagtgtttat cggcgtcaag gacaaccacc tggctctgat caaggtggat 480
agctccgaga acctgtgtac agaaaatatc ctgttcaagc tgagcgagac t 531

<210> SEQ ID NO 2
<211> LENGTH: 177
<212> TYPE: PRT
<213> ORGANISM: Artificial Sequence
<220> FEATURE:
<223> OTHER INFORMATION: Optimized HmtrIL-33 Protein sequence

<400> SEQUENCE: 2

Met Asp Trp Thr Trp Ile Leu Phe Leu Val Ala Ala Ala Thr Arg Val
1 5 10 15

His Ser Ser Ile Thr Gly Ile Ser Pro Ile Thr Glu Tyr Leu Ala Ser
20 25 30

Leu Ser Thr Tyr Asn Asp Gln Ser Ile Thr Phe Ala Leu Glu Asp Glu
35 40 45

Ser Tyr Glu Ile Tyr Val Glu Asp Leu Lys Lys Asp Glu Lys Lys Asp
50 55 60

Lys Val Leu Leu Ser Tyr Tyr Glu Ser Gln His Pro Ser Asn Glu Ser
65 70 75 80

Gly Asp Gly Val Asp Gly Lys Met Leu Met Val Thr Leu Ser Pro Thr
85 90 95

Lys Asp Phe Trp Leu His Ala Asn Asn Lys Glu His Ser Val Glu Leu
100 105 110

His Lys Cys Glu Lys Pro Leu Pro Asp Gln Ala Phe Phe Val Leu His
115 120 125

Asn Met His Ser Asn Cys Val Ser Phe Glu Cys Lys Thr Asp Pro Gly
130 135 140

Val Phe Ile Gly Val Lys Asp Asn His Leu Ala Leu Ile Lys Val Asp
145 150 155 160

Ser Ser Glu Asn Leu Cys Thr Glu Asn Ile Leu Phe Lys Leu Ser Glu
165 170 175

Thr

<210> SEQ ID NO 3
<211> LENGTH: 861
<212> TYPE: DNA

<213> ORGANISM: Artificial Sequence
<220> FEATURE:
<223> OTHER INFORMATION: Optimized hproIL-33 DNA sequence

<400> SEQUENCE: 3

```
atggactgga catgattct gttcctggtc gccgccgcaa cccgcgtgca ttctaaacct    60
aaaatgaaat actcaactaa taagatttct accgctaagt ggaaaaacac tgccagtaag   120
gccctgtgct tcaagctggg caaaagccag cagaaggcaa agaagtgtg tcctatgtac    180
ttcatgaaac tgcgatccgg gctgatgatt aagaaagagg cctgctattt cggagagaa    240
accacaaaga gaccatctct gaaaactgga aggaagcaca aacgccatct ggtgctggcc   300
gcttgccagc agcagtccac cgtcgagtgt ttcgcttttg aatctctgg cgtgcagaag    360
tacacacggg cactgcacga cagctccatc accggcatta gccccatcac agaatacctg   420
gcctcactga gcacttataa cgatcagtca attaccttcg ctctggagga cgaaagctac   480
gagatctatg tcgaagacct gaagaaagat gagaagaaag acaaggtgct gctgagttac   540
tatgagtcac agcacccatc caatgaatct ggcgacgggg tggatgggaa aatgctgatg   600
gtcactctga gtcccaccaa ggacttttgg ctgcatgcaa acaacaagga gcacagcgtg   660
gaactgcata agtgcgagaa acccctgcct gatcaggcct ctttgtgct gcacaacatg    720
catagcaatt gcgtctcctt cgagtgtaag acagatcctg gggtgtttat tggagtcaag   780
gacaatcatc tggctctgat caaagtggat tctagtgaga acctgtgtac agaaaatatt   840
ctgtttaagc tgagcgagac t                                            861
```

<210> SEQ ID NO 4
<211> LENGTH: 287
<212> TYPE: PRT
<213> ORGANISM: Artificial Sequence
<220> FEATURE:
<223> OTHER INFORMATION: Optimized hproIL-33 protein sequence

<400> SEQUENCE: 4

```
Met Asp Trp Thr Trp Ile Leu Phe Leu Val Ala Ala Ala Thr Arg Val
 1               5                  10                  15

His Ser Lys Pro Lys Met Lys Tyr Ser Thr Asn Lys Ile Ser Thr Ala
            20                  25                  30

Lys Trp Lys Asn Thr Ala Ser Lys Ala Leu Cys Phe Lys Leu Gly Lys
        35                  40                  45

Ser Gln Gln Lys Ala Lys Glu Val Cys Pro Met Tyr Phe Met Lys Leu
    50                  55                  60

Arg Ser Gly Leu Met Ile Lys Lys Glu Ala Cys Tyr Phe Arg Arg Glu
65                  70                  75                  80

Thr Thr Lys Arg Pro Ser Leu Lys Thr Gly Arg Lys His Lys Arg His
                85                  90                  95

Leu Val Leu Ala Ala Cys Gln Gln Gln Ser Thr Val Glu Cys Phe Ala
            100                 105                 110

Phe Gly Ile Ser Gly Val Gln Lys Tyr Thr Arg Ala Leu His Asp Ser
        115                 120                 125

Ser Ile Thr Gly Ile Ser Pro Ile Thr Glu Tyr Leu Ala Ser Leu Ser
    130                 135                 140

Thr Tyr Asn Asp Gln Ser Ile Thr Phe Ala Leu Glu Asp Glu Ser Tyr
145                 150                 155                 160

Glu Ile Tyr Val Glu Asp Leu Lys Lys Asp Glu Lys Lys Asp Lys Val
                165                 170                 175
```

```
Leu Leu Ser Tyr Tyr Glu Ser Gln His Pro Ser Asn Glu Ser Gly Asp
            180                 185                 190

Gly Val Asp Gly Lys Met Leu Met Val Thr Leu Ser Pro Thr Lys Asp
        195                 200                 205

Phe Trp Leu His Ala Asn Asn Lys Glu His Ser Val Glu Leu His Lys
    210                 215                 220

Cys Glu Lys Pro Leu Pro Asp Gln Ala Phe Phe Val Leu His Asn Met
225                 230                 235                 240

His Ser Asn Cys Val Ser Phe Glu Cys Lys Thr Asp Pro Gly Val Phe
                245                 250                 255

Ile Gly Val Lys Asp Asn His Leu Ala Leu Ile Lys Val Asp Ser Ser
            260                 265                 270

Glu Asn Leu Cys Thr Glu Asn Ile Leu Phe Lys Leu Ser Glu Thr
        275                 280                 285

<210> SEQ ID NO 5
<211> LENGTH: 852
<212> TYPE: DNA
<213> ORGANISM: Artificial Sequence
<220> FEATURE:
<223> OTHER INFORMATION: Optimized mouse proIL-33 DNA sequence

<400> SEQUENCE: 5
atggactgga cctggattct cttcctggtg gccgccgcaa cccgcgtgca tagcagacct      60
cgcatgaaat actcaaactc aaaaatttcc cctgctaagt tcagctccac cgcaggagag     120
gccctggtgc ccccttgcaa aatcaggaga agccagcaga agacaaaaga gttctgccac     180
gtctactgta tgcggctgcg ctcaggcctc actattcgca aggagaccag ctactttaga     240
aaggaaccca aaaacggta tagcctgaag tccggaacta acatgaggga aaacttctcc     300
gcttatccca gggacagcag gaagaggagt ctgctcgggt caatccaggc atttgccgct     360
agcgtggata ctctgtccat tcagggcacc agcctgctca cacagagtcc agcatcactg     420
agcacctaca atgaccagag cgtgagcttc gtgctggaga acggctgcta tgtgatcaac     480
gtggacgata gtggaaagga ccaggagcag gatcaggtgc tgctccggta ctatgaaagc     540
ccttgtccag ccagtcagtc aggcgacgga gtggatggga agaaactgat ggtcaacatg     600
agcccaatca aggacacaga tatttggctg cacgccaatg acaaagatta ctccgtggag     660
ctccagaggg gcgacgtgag ccctcccgaa caggctttct tgtgctgca taagaaatct      720 agtgatttcg tcagctttga gtgtaagaac ctgcccggga cctatattgg tgtgaaagat     780
aatcagctcg ccctggtgga agaaaaagac gaatcctgta taatatcat gttcaagctg      840 tcaaaaatct aa                                                         852

<210> SEQ ID NO 6
<211> LENGTH: 283
<212> TYPE: PRT
<213> ORGANISM: Artificial Sequence
<220> FEATURE:
<223> OTHER INFORMATION: Optimized mouse proIL-33 protein sequence

<400> SEQUENCE: 6

Met Asp Trp Thr Trp Ile Leu Phe Leu Val Ala Ala Ala Thr Arg Val
1               5                   10                  15

His Ser Arg Pro Arg Met Lys Tyr Ser Asn Ser Lys Ile Ser Pro Ala
            20                  25                  30

Lys Phe Ser Ser Thr Ala Gly Glu Ala Leu Val Pro Pro Cys Lys Ile
        35                  40                  45
```

Arg Arg Ser Gln Gln Lys Thr Lys Glu Phe Cys His Val Tyr Cys Met
    50                  55                  60

Arg Leu Arg Ser Gly Leu Thr Ile Arg Lys Glu Thr Ser Tyr Phe Arg
65                  70                  75                  80

Lys Glu Pro Thr Lys Arg Tyr Ser Leu Lys Ser Gly Thr Lys His Glu
                85                  90                  95

Glu Asn Phe Ser Ala Tyr Pro Arg Asp Ser Arg Lys Arg Ser Leu Leu
            100                 105                 110

Gly Ser Ile Gln Ala Phe Ala Ala Ser Val Asp Thr Leu Ser Ile Gln
        115                 120                 125

Gly Thr Ser Leu Leu Thr Gln Ser Pro Ala Ser Leu Ser Thr Tyr Asn
    130                 135                 140

Asp Gln Ser Val Ser Phe Val Leu Glu Asn Gly Cys Tyr Val Ile Asn
145                 150                 155                 160

Val Asp Asp Ser Gly Lys Asp Gln Glu Gln Asp Gln Val Leu Leu Arg
                165                 170                 175

Tyr Tyr Glu Ser Pro Cys Pro Ala Ser Gln Ser Gly Asp Gly Val Asp
            180                 185                 190

Gly Lys Lys Leu Met Val Asn Met Ser Pro Ile Lys Asp Thr Asp Ile
        195                 200                 205

Trp Leu His Ala Asn Asp Lys Asp Tyr Ser Val Glu Leu Gln Arg Gly
    210                 215                 220

Asp Val Ser Pro Pro Glu Gln Ala Phe Phe Val Leu His Lys Lys Ser
225                 230                 235                 240

Ser Asp Phe Val Ser Phe Glu Cys Lys Asn Leu Pro Gly Thr Tyr Ile
                245                 250                 255

Gly Val Lys Asp Asn Gln Leu Ala Leu Val Glu Glu Lys Asp Glu Ser
            260                 265                 270

Cys Asn Asn Ile Met Phe Lys Leu Ser Lys Ile
        275                 280

<210> SEQ ID NO 7
<211> LENGTH: 528
<212> TYPE: DNA
<213> ORGANISM: Artificial Sequence
<220> FEATURE:
<223> OTHER INFORMATION: Optimized mouse mtrIL-33 DNA sequence

<400> SEQUENCE: 7
atggactgga cctggattct gttcctcgtc gccgccgcaa cacgggtgca ttcttcaatt      60
caggggacct cactgctcac acagagtccc gcatctctga gtacctacaa cgaccagagc     120
gtgagcttcg tgctggagaa cggctgctat gtgatcaacg tggacgatag cggaaaggac     180
caggagcagg atcaggtgct gctcaggtac tatgaatccc catgtccagc atcccagtct     240
ggcgacggag tggatgggaa gaaactgatg gtcaacatgt ctcctatcaa ggacaccgat     300
atttggctgc acgccaatga caaagattac agtgtggagc tccagagggg cgacgtgagc     360
cctcccgaac aggctttctt tgtgctgcat aagaaaagct ccgatttcgt ctcctttgaa     420
tgcaagaacc tgccagggac atatattggt gtgaaagata tcagctcgc tctggtggaa      480 gaaaaagacg aatcctgtaa taatatcatg ttcaagctct caaaaatc                  528

<210> SEQ ID NO 8
<211> LENGTH: 176
<212> TYPE: PRT
<213> ORGANISM: Artificial Sequence
<220> FEATURE:
<223> OTHER INFORMATION: Optimized mouse mtrIL-33 protein sequence

<400> SEQUENCE: 8

```
Met Asp Trp Thr Trp Ile Leu Phe Leu Val Ala Ala Ala Thr Arg Val
1               5                   10                  15

His Ser Ser Ile Gln Gly Thr Ser Leu Leu Thr Gln Ser Pro Ala Ser
            20                  25                  30

Leu Ser Thr Tyr Asn Asp Gln Ser Val Ser Phe Val Leu Glu Asn Gly
        35                  40                  45

Cys Tyr Val Ile Asn Val Asp Asp Ser Gly Lys Asp Gln Glu Gln Asp
    50                  55                  60

Gln Val Leu Leu Arg Tyr Tyr Glu Ser Pro Cys Pro Ala Ser Gln Ser
65                  70                  75                  80

Gly Asp Gly Val Asp Gly Lys Lys Leu Met Val Asn Met Ser Pro Ile
                85                  90                  95

Lys Asp Thr Asp Ile Trp Leu His Ala Asn Asp Lys Asp Tyr Ser Val
                100                 105                 110

Glu Leu Gln Arg Gly Asp Val Ser Pro Pro Glu Gln Ala Phe Phe Val
            115                 120                 125

Leu His Lys Lys Ser Ser Asp Phe Val Ser Phe Glu Cys Lys Asn Leu
        130                 135                 140

Pro Gly Thr Tyr Ile Gly Val Lys Asp Asn Gln Leu Ala Leu Val Glu
145                 150                 155                 160

Glu Lys Asp Glu Ser Cys Asn Asn Ile Met Phe Lys Leu Ser Lys Ile
                165                 170                 175
```

<210> SEQ ID NO 9
<211> LENGTH: 9
<212> TYPE: PRT
<213> ORGANISM: Artificial Sequence
<220> FEATURE:
<223> OTHER INFORMATION: LCMV-GP33 protein

<400> SEQUENCE: 9

```
Lys Ala Val Tyr Asn Phe Ala Thr Cys
1               5
```

VACCINES WITH INTERLEUKIN-33 AS AN ADJUVANT

CROSS-REFERENCE TO RELATED APPLICATIONS

This application is the U.S. national stage application filed under 35 U.S.C. § 371 claiming benefit to International Patent Application No. PCT/US14/58727, filed Oct. 2, 2014, which is entitled to priority under 35 U.S.C. § 119(e) to U.S. Provisional Application Nos. 61/887,502, filed Oct. 7, 2013 and 61/895,673, filed Oct. 25, 2013, each of which is hereby incorporated by reference in their entirety.

TECHNICAL FIELD

The present invention relates to vaccines comprising an antigen and IL-33, and methods of administering such vaccines.

BACKGROUND

Vaccines are used to stimulate an immune response in an individual to provide protection against and/or treatment for a particular disease. Some vaccines include an antigen to induce the immune response. Some antigens elicit a strong immune response while other antigens elicit a weak immune response. A weak immune response to an antigen can be strengthened by including an adjuvant in the vaccine. Adjuvants come in many different forms, for example, aluminum salts, oil emulsions, sterile constituents of bacteria or other pathogens, cytokines, and so forth.

Cytokines are proteins made by cells that affect the behavior of other cells, and unlike many adjuvants, can modulate specific immune responses. One such cytokine is Interleukin-33 (IL-33). IL-33 is an endogenous signal or alarmin that alerts the immune system upon tissue injury or infection. In particular, full-length IL-33 is released into the extracellular space and activates its receptor ST2. Activation of ST2 leads to inflammatory and type 2 immune responses.

Vaccines are also administered in many different ways (e.g., injection, orally, etc.) into many different tissues (e.g., intramuscular, nasal, etc.). Not all delivery methods, however, are equal. Some delivery methods allow for greater compliance within a population of individuals while other delivery methods may affect immunogenicity and/or safety of the vaccine. Accordingly, a need remains in the art for the development of safe and more effective adjuvants that increase immune responses to the antigen.

SUMMARY

The present invention is directed to a vaccine comprising an antigen and IL-33. IL-33 can be encoded by a nucleotide sequence selected from the group consisting of: a nucleotide sequence having at least about 95% identity to a nucleotide sequence as set forth in SEQ ID NO:1, a nucleotide sequence as set forth in SEQ ID NO:1, a nucleotide sequence having at least about 95% identity to a nucleotide sequence as set forth in SEQ ID NO:3, and a nucleotide sequence as set forth in SEQ ID NO:3. IL-33 can be encoded by the nucleotide sequence as set forth in SEQ ID NO:1. IL-33 can be encoded by the nucleotide sequence as set forth in SEQ ID NO:3.

The antigen can be encoded by a first nucleic acid and IL-33 can be encoded by a second nucleic acid. The second nucleic acid can further comprise an expression vector. The vaccine can further comprise an antigen peptide with the same encoded nucleic acid sequence as the above antigen and an IL-33 peptide with the same encoded nucleic acid sequence as the above IL-33.

IL-33 can be selected from the group consisting of: proIL-33 and mtrIL-33. IL-33 can be proIL-33. ProIL-33 can be encoded by a nucleotide sequence as set forth in SEQ ID NO:3. IL-33 can be mtrIL-33. MtrIL-33 can be encoded by a nucleotide sequence as set forth in SEQ ID NO:1.

The antigen can be selected from the group consisting of: a human papilloma virus (HPV) antigen, an Human Immunodeficiency Virus (HIV) antigen, an influenza antigen, a *Plasmodium falciparum* antigen, a *Mycobacterium tuberculosis* antigen, a lymphocytic choriomeningitis (LCMV) antigen, and a fragment thereof. The HPV antigen can be selected from the group consisting of: HPV16 E6 antigen, HPV16 E7 antigen, and a combination thereof. The HIV antigen can be selected from the group consisting of: Env A, Env B, Env C, Env D, B Nef-Rev, Gag, and any combination thereof. The influenza antigen can be selected from the group consisting of: H1 HA, H2 HA, H3 HA, H5 HA, BHA antigen, and any combination thereof. The *Plasmodium falciparum* antigen can include a circumsporozoite (CS) antigen. The *Mycobacterium tuberculosis* antigen can be selected from the group consisting of: Ag85A, Ag85B, EsxA, EsxB, EsxC, EsxD, EsxE, EsxF, EsxH, EsxO, EsxQ, EsxR, EsxS, EsxT, EsxU, EsxV, EsxW, and any combination thereof. The LCMV antigen can be selected from the group consisting of: nucleoprotein (NP), glycoprotein (GP), and a combination thereof.

The vaccine can further comprise a pharmaceutically acceptable excipient.

The present invention is also directed to a method for increasing an immune response in a subject in need thereof. The method can comprise administering a vaccine comprising an antigen and IL-33 to the subject. IL-33 can be encoded by a nucleotide sequence selected from the group consisting of: a nucleotide sequence having at least about 95% identity to a nucleotide sequence as set forth in SEQ ID NO:1, a nucleotide sequence as set forth in SEQ ID NO:1, a nucleotide sequence having at least about 95% identity to a nucleotide sequence as set forth in SEQ ID NO:3, and a nucleotide sequence as set forth in SEQ ID NO:3. IL-33 can be encoded by the nucleotide sequence as set forth in SEQ ID NO:1. IL-33 can be encoded by the nucleotide sequence as set forth in SEQ ID NO:3.

Administering the vaccine can include electroporation. The immune response in the subject can be increased by at least about 2-fold. The immune response in the subject can be increased by at least about 4-fold. Increasing the immune response in the subject can include increasing a cellular immune response in the subject.

The present invention is further directed to a method for treating cancer in a subject in need thereof. The method can comprise administering a vaccine comprising an antigen and IL-33 to the subject. IL-33 can be encoded by a nucleotide sequence selected from the group consisting of: a nucleotide sequence having at least about 95% identity to a nucleotide sequence as set forth in SEQ ID NO:1, a nucleotide sequence as set forth in SEQ ID NO:1, a nucleotide sequence having at least about 95% identity to a nucleotide sequence as set forth in SEQ ID NO:3, and a nucleotide sequence as set forth in SEQ ID NO:3. IL-33 can be encoded by the nucleotide sequence as set forth in SEQ ID NO:1. IL-33 can be encoded by the nucleotide sequence as set forth in SEQ ID NO:3.

The method for treating cancer can further comprise reducing tumor size in the subject. The method for treating cancer can further comprise increasing tumor regression in the subject. The cancer can be selected from the group consisting of: an HPV-associated cancer, an HBV-associated cancer, an ovarian cancer, a prostate cancer, a breast cancer, a brain cancer, a head and neck cancer, a throat cancer, a lung cancer, a liver cancer, a cancer of the pancreas, a kidney cancer, a bone cancer, a melanoma, a metastatic cancer, an hTERT-associated cancer, a FAP-antigen associated cancer, a non-small cell lung cancer, a blood cancer, an esophageal squamous cell carcinoma, a cervical cancer, a bladder cancer, a colorectal cancer, a gastric cancer, an anal cancer, a synovial carcinoma, a testicular cancer, a recurrent respiratory papillomatosis, a skin cancer, a glioblastoma, an hepatocarcinoma, a stomach cancer, an acute myeloid leukemia, a triple-negative breast cancer, and primary cutaneous T cell lymphoma. The cancer can be the HPV-associated cancer.

The present invention is further directed to a nucleic acid molecule comprising one or more nucleotide sequences selected from the group consisting of: SEQ ID NO:1, SEQ ID NO:3, a nucleotide sequence that is 95% identical or greater to SEQ ID NO:1, a nucleotide sequence that is 95% identical or greater to SEQ ID NO:3, and any combination thereof. The nucleic acid molecule can be a plasmid. The nucleic acid molecule can be one or more plasmids.

DETAILED DESCRIPTION

Figure 1:
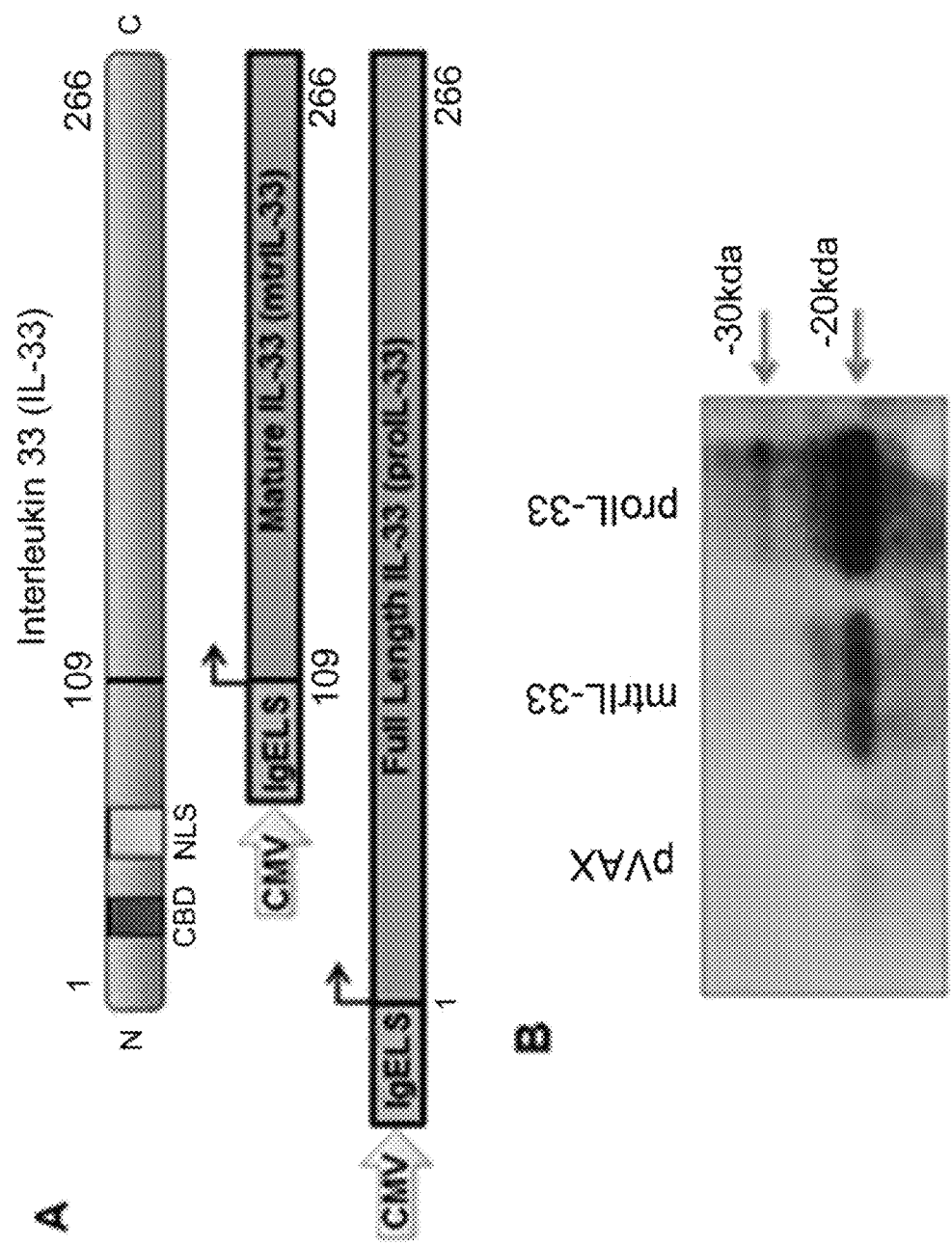
FIG. 1 shows in (A) a schematic representation of the mouse proIL-33 and mouse mtrIL-33 constructs; (B) western blot detection of proIL-33 and mtrIL-33; (C) ELISA detection of secreted proIL-33 and mtrIL-33; and (D) cellular localization of proIL-33 and mtrIL-33.

The present invention relates to a vaccine that can be used to increase an immune response to an antigen in a subject by using IL-33 as an adjuvant. When used as an adjuvant, IL-33 unexpectedly increases T helper 1 (Th1), and not T helper 2 (Th2) immune responses. This is in stark contrast to IL-33's biological function in activating the innate and Th2 immune responses. In some instances, IL-33 can increase the levels of the anti-viral cytokines Interferon-gamma (IFN-γ) and tumor necrosis factor alpha (TNF-α). IL-33 can also increase the level of the cytokine IL-2. Accordingly, IL-33 can increase subpopulations of polyfunctional CD4$^+$ T cells and CD8$^+$ T cells to promote the cellular immune response.

IL-33 can further induce expansion and differentiation of effector-memory T cells to promote the cellular immune response. CD122$^+$CD8$^+$ regulatory T cells may reduce the effectiveness of a vaccine and thus, suppression of these cells by IL-33 can further promote the cellular immune response induced by the vaccine.

IL-33 can augment the cellular immune response to antigens such as viral and bacterial antigens, for example, a human papilloma virus (HPV) antigen, an human immunodeficiency virus (HIV) antigen, a *Mycobacterium tuberculosis* antigen, and a lymphocytic choriomeningitis virus (LCMV) antigen. As such, IL-33 can promote significant protection against such pathogens.

The vaccine of the present invention can prevent cancer or tumor formation. The vaccine can also cause regression of established cancer or tumors. The regression can be 90% or greater regression. The regression of the cancer can be complete. The vaccine can further prevent and cause regression of virus-associated cancers, for example, HPV-associated cancer. Accordingly, also provided herein is a method for the treatment of cancer by administering the vaccine to a subject in need thereof.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Adjuvant" as used herein means any molecule added to the vaccine described herein to enhance the immunogenicity of the antigens.

"Fragment" as used herein means a nucleic acid sequence or a portion thereof, that encodes a polypeptide capable of eliciting an immune response in a mammal. The fragments can be DNA fragments selected from at least one of the various nucleotide sequences that encode protein fragments set forth below.

"Immune response" as used herein means the activation of a host's immune system, e.g., that of a mammal, in response to the introduction of antigen. The immune response can be in the form of a cellular or humoral response, or both.

"Nucleic acids" as used herein can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Treatment" or "treating," as used herein can mean protection of an animal from a disease through means of preventing, suppressing, repressing, or completely eliminating the disease. Preventing the disease involves administering a vaccine of the present invention to an animal prior to onset of the disease. Suppressing the disease involves administering a vaccine of the present invention to an animal after induction of the disease, but before its clinical appearance. Repressing the disease involves administering a vaccine of the present invention to an animal after clinical appearance of the disease.

"Subject" as used herein can mean a mammal that wants to or is in need of being immunized with the herein described vaccine. The mammal can be a human, chimpanzee, dog, cat, horse, cow, mouse, or rat.

"Variant" as used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

Variant can further be defined as a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. Substitution of amino acids having similar hydrophilicity values can result in peptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly, the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and preferably, is a DNA plasmid.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. VACCINE

Provided herein is a vaccine comprising an antigen and an adjuvant. The vaccine can increase antigen presentation and the overall immune response to the antigen in a subject. The combination of antigen and adjuvant induces the immune system more efficiently than a vaccine comprising the antigen alone. This more efficient immune response provides increased efficacy in the treatment and/or prevention of any disease, pathogen, or virus, including cancer as described in more detail below.

The vaccine of the present invention can have features required of effective vaccines such as being safe so that the vaccine itself does not cause illness or death; being protective against illness resulting from exposure to live pathogens such as viruses or bacteria; inducing neutralizing antibody to prevent infection of cells; inducing protective T cell response against intracellular pathogens; and providing ease of administration, few side effects, biological stability, and low cost per dose. The vaccine can accomplish some or all of these features by combining the antigen with the adjuvant as discussed below.

The vaccine can further modify epitope presentation within the antigen to induce greater immune response to the antigen than a vaccine comprising the antigen alone. The vaccine can further induce an immune response when administered to different tissues such as the muscle or the skin.

a. Adjuvant

The vaccine can comprise an adjuvant. The adjuvant can be a nucleic acid sequence, an amino acid sequence, or a combination thereof. The nucleic acid sequence can be DNA, RNA, cDNA, a variant thereof, a fragment thereof, or a combination thereof. The nucleic acid sequence can also include additional sequences that encode linker or tag sequences that are linked to the adjuvant by a peptide bond. The amino acid sequence can be a protein, a peptide, a variant thereof, a fragment thereof, or a combination thereof.

(1) IL-33

The adjuvant can be interleukin-33 (IL-33), fragments thereof, variants thereof, or combinations thereof. IL-33 is a member of the Interleukin-1 (IL-1) family of cytokines, which are involved in early immune and inflammatory responses following tissue injury or infection. IL-1 family members also coordinate later adaptive immune responses, namely T helper 2 (Th2) immune responses. Dysregulation of this family has been implicated in many diseases, for example, asthma, rheumatoid arthritis, Crohn's disease, periodontitis, and sepsis. In particular, IL-33 levels are elevated in the inflammatory diseases asthma and rheumatoid arthritis, and IL-33 promotes the pathogenesis of Th2-related diseases such as asthma, atopic dermatitis, and anaphylaxis. In contrast, IL-33 has protective effects in cardiovascular diseases such as atherosclerosis, obesity, type 2 diabetes, and cardiac remodeling, and contributes to host defense against parasitic and bacterial infections.

Full-length IL-33 is constitutively expressed in the nucleus of endothelial and epithelial cells, where it is associated with heterochromatin and mitotic chromatin. The amino terminus of full-length IL-33 includes a chromatin binding domain or motif (CBD) and nuclear localization signal (NLS). In particular, the CBD is a homeodomain-like helix-turn-helix motif, which acts as a transcriptional repressor.

Full-length IL-33, however, is also released into the extracellular space upon tissue injury or infection as an alarmin. Extracellular IL-33 binds the cell surface receptor ST2 to activate cells of the innate immune system, for example, mast cells and eosinophils, to signal danger (i.e., injury or infection) and induce an inflammatory response. Induced pro-inflammatory mediators include tumor necrosis factor (TNF), IL-1β, and Interferon-gamma (IFN-γ). IL-33 also induces more recently discovered innate immune cells, namely innate lymphoid cells type 2 (ILC2). ILC2 are non-B non-T cells and produce Th2 type cytokines, for example, Interleukin-4, -5, and -13 (IL-4, IL-5, and IL-13, respectively).

Additionally, extracellular IL-33 is cleaved by proteases, in which the resulting fragments bind ST2 and amplify the initial "danger" signal. ST2 is also expressed in many other cell types (though mostly hematopoietic), for example, different subsets of $CD4^+$ T cells, basophils, monocytes, macrophages, natural killer cells, invariant natural killer T cells, and activated neutrophils, thereby allowing IL-33 to induce production of various cytokines and chemokines, and cell activation, differentiation, polarization, or chemotaxis. ST2 is a selective marker for Th2 type cells and exists as a membrane bound form and a soluble form. The membrane bound form of ST2 when bound by IL-33 triggers nuclear factor (NF)-κB and mitogen-activated protein kinase pathways (e.g., p38, JNK, ERK1, and ERK2) to initiate cell signaling. Soluble ST2 also binds IL-33, but is a decoy molecule, thereby inhibiting IL-33.

Furthermore, IL-33 can exist in a mature or truncated form that lacks the CBD and NLS. Mature IL-33 can act as a proinflammatory cytokine to modulate immune responses.

IL-33 can increase or boost the immune response to the antigen in the subject. The antigen is discussed in more detail below. In some instances, IL-33 can increase the immune response to the antigen by about 75% to about 200%. Alternatively, IL-33 can increase the immune response to the antigen by about 90% to about 130%. In still other alternative embodiments, IL-33 can increase the immune response to the antigen by about 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, or 130%.

In other embodiments, IL-33 can increase or boost the immune response to the antigen by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, or at least about 10.0-fold.

When IL-33 increases or boosts the immune response to the antigen in the subject, Interleukin-4 (IL-4) levels (secretion) and Immunoglobin E (IgE) levels are not increased in the subject. Unexpectedly, IL-33 as an adjuvant does not increase or boost the Th2 immune response to the antigen in the subject. IL-33 as an adjuvant, instead, can increase or boost the Th1 or cellular immune response to the antigen in the subject.

The Th1 immune response involves the activation of T cell responses. These T cell responses may include $CD4^+$ and $CD8^+$ T cell responses and the secretion of interferon-gamma, tumor necrosis factor alpha, and/or interleuking (IL-2). Interferon-gamma and tumor necrosis factor alpha have antiviral, immunoregulatory, and anti-tumor properties and can alter transcription in multiple genes to produce a variety of physiological and cellular responses. Some effects by interferon-gamma include promoting natural killer cell (NK cells) activity, causing normal cells to increase expression of class I MHC molecules, increasing antigen presentation and lysosome activity in macrophages, inducing nitric oxide synthase (iNOS), and promoting Th1 differentiation in cellular immunity with regards to cytotoxic $CD8^+$ T cells while suppressing Th2 differentiation in humoral (antibody) immunity.

Cytotoxic $CD8^+$ T cells (cytotoxic T lymphocytes (CTLs)) are a subgroup of T cells that induce the death of cells infected with viruses and other pathogens. Upon activation, CTLs undergo clonal expansion to produce effector cells that are antigen-specific. Effector CTLs release through a process of directed exocytosis (i.e., degranulation) molecules that kill infected or target cells, for example, perforin, granulysin, and granzyme. When no longer needed, many effector CTLs die, but some effector cells are retained as memory cells such that when the antigen is encountered again, the memory cells differentiate into effector cells to more quickly mount an immune response.

When IL-33 increases or boosts the Th1 or cellular immune response, Interferon-gamma (IFN-γ) levels (secretion) are increased. In some instances, IL-33 can increase the Th1 or cellular immune response to the antigen by about 1.5-fold to about 10.0-fold, about 1.5-fold to about 8.0-fold, about 1.5-fold to about 6.0-fold, about 1.5-fold to about 4.0-fold, about 2.0-fold to about 10.0-fold, about 2.0-fold to about 8.0-fold, about 2.0-fold to about 6.0-fold, about 2.0-fold to about 4.0-fold, about 2.5-fold to about 4.0-fold, about 4.0-fold to about 10.0-fold, about 6.0-fold to about 10.0-fold, or about 8.0-fold to about 10.0-fold. IL-33 can also increase the Th1 or cellular immune response to the antigen by at least about 2.5-fold, at least about 2.6-fold, at least about 2.7-fold, at least about 2.8-fold, at least about 2.9-fold, at least about 3.0-fold, at least about 3.1-fold, at least about 3.2-fold, at least about 3.3-fold, at least about 3.4-fold, at least about 3.5-fold, at least about 3.6-fold, at least about 3.7-fold, at least about 3.8-fold, at least about 3.9-fold, at least about 4.0-fold, at least about 4.1-fold, at least about 4.2-fold, at least about 4.3-fold, at least about 4.4-fold, at least about 4.5-fold, at least about 4.6-fold, at least about 4.7-fold, at least about 4.8-fold, at least about 4.9-fold, at least about 5.0-fold, at least about 6.0-fold, at least about 7.0-fold, at least about 8.0-fold, at least about 9.0-fold, or at least about 10.0-fold. IL-33 can further increase the Th1 or cellular immune response by about 3.5-fold or 4.0-fold.

The increased or boosted immune response to the antigen can also include an increased $CD4^+$ T cell response. The increased $CD4^+$ T cell response can include increasing in the subject the population or frequency of $CD4^+$ T cells that secrete IFN-γ, tumor necrosis factor alpha (TNF-α), IL-2, or both IFN-γ and TNF-α, or some combination of IFN-γ, TNF-α, and IL-2 (e.g., triple-positive cells expressing IFN-γ, TNF-α, and IL-2). Accordingly, the increased $CD4^+$ T cell response can include increasing subpopulations of polyfunctional $CD4^+$ T cells.

The increased or boosted immune response to the antigen can further include an increased $CD8^+$ T cell response. The increased $CD8^+$ T cell response can include increasing in the subject the population or frequency of $CD8^+$ T cells that secrete IFN-γ, TNF-α, IL-2, or both IFN-γ and TNF-α, or some combination of IFN-γ, TNF-α, and IL-2 (e.g., triple-positive cells expressing IFN-γ, TNF-α, and IL-2). Accordingly, the increased $CD8^+$ T cell response can include increasing subpopulations of polyfunctional $CD8^+$ T cells.

The increased $CD8^+$ T cell response can also include an increased cytotoxic CD8+ T lymphocyte (CTL) response. The increased CTL response can include increasing in the subject the population or frequency of $CD8^+$ T cells undergoing degranulation. The increased CTL response can further include increasing in the subject the population or frequency of CD8+ T cells expressing CD107a. The increased CTL response can further include increasing in the subject the population or frequency of $CD8^+$ T cells co-expressing CD107a, IFN-γ, and TNF-α.

The increased or boosted immune response to the antigen can further include the expansion and differentiation of $CD8^+$ T cells in the subject. Such expansion can occur in the periphery. Additionally, recall of established memory $CD8^+$ T cells is increased in the subject. As such, IL-33 can increase the cellular immune response by expanding both effector and effector-memory $CD8^+$ T cell populations that are specific to the antigen. The expanded effector and effector-memory $CD8^+$ T cell populations can have an increased frequency of cells that express KLRG1.

The increased or boosted immune response to the antigen can further include the suppression of $CD122^+CD8^+$ regulatory T cells, for example, by preventing expansion of these cells. $CD122^+CD8^+$ regulatory T cells may suppress the immune response induced by a vaccine and thus, the effectiveness of a vaccine. By suppressing $CD122^+CD8^+$ regulatory T cells, IL-33 increases the immune response to the antigen, and thus, the effectiveness (i.e., protection) provided by the vaccine.

The increased or boosted immune response to the antigen can further include protection against disease associated with the antigen. In some embodiments, the increased or boosted immune response to the antigen can include complete protection against disease associated with the antigen. In other embodiments, the increased or boosted immune response to the antigen can include at least about a 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% survival rate against disease associated with the antigen.

(a) ProIL-33

IL-33 can be a proIL-33, fragments thereof, or variants thereof. ProIL-33 is full-length or uncleaved IL-33. Accordingly, proIL-33 includes both the chromatin binding domain or motif (CBD) and a nuclear localization signal (NLS). ProIL-33 can be localized in both the nucleus and cytoplasm. In particular, proIL-33 can be substantially localized in the nucleus.

As described above for IL-33, proIL-33 does not increase the levels of IgE when increasing the immune response. ProIL-33, unlike mtrIL-33 which is described below, can increase in the subject the levels of Immunoglobulin G (IgG) specific to the antigen. ProIL-33 can increase the levels of IgG specific to the antigen by about 1.5-fold to about 10.0-fold, about 2.0-fold to about 6.0-fold, or about 2.0-fold to about 4.0-fold. ProIL-33 can also increase the levels of IgG specific to the antigen by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, or at least about 10.0-fold.

A nucleic acid encoding proIL-33 can be from any number of organisms, for example, mouse (*Mus musculus*) and human (*Homo sapiens*). The nucleic acid encoding proIL-33 can be optimized with regards to codon usage and corresponding RNA transcripts. The nucleic acid encoding proIL-33 can be codon and RNA optimized for expression. In some embodiments, the nucleic acid encoding proIL-33 can include a Kozak sequence (e.g., GCC ACC) to increase the efficiency of translation. The nucleic acid encoding proIL-33 can include multiple stop codons (e.g., TGA TGA) to increase the efficiency of translation termination. The nucleic acid encoding proIL-33 can also include a nucleotide sequence encoding an Immunoglobulin E (IgE) leader sequence. The IgE leader sequence can be located 5' to proIL-33 in the nucleic acid. In some embodiments, the nucleic acid encoding proIL-33 is free of or does not contain a nucleotide sequence encoding the IgE leader sequence.

The mouse proIL-33 can be the optimized nucleic acid sequence SEQ ID NO:5, which encodes SEQ ID NO:6. In some embodiments, the mouse proIL-33 can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:5. In other embodiments, the mouse proIL-33 can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence as set forth in SEQ ID NO:6. The mouse proIL-33 can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence as set forth in SEQ ID NO:6.

The human proIL-33 can be the optimized nucleic acid sequence SEQ ID NO:3, which encodes SEQ ID NO:4. In some embodiments, the human proIL-33 can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:3. In other embodiments, the human proIL-33 can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence as set forth in SEQ ID NO:4. The human proIL-33 can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence as set forth in SEQ ID NO:4.

Some embodiments relate to fragments of SEQ ID NO:3 and/or SEQ ID NO:5. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:3 and/or SEQ ID NO:5. In some embodiments, fragments can include sequences that encode a leader sequence, for example, an immunoglobulin leader sequence, such as the IgE leader sequence. In some embodiments, fragments are free of coding sequences that encode a leader sequence.

Fragments of nucleic acids with nucleotide sequences having identity to fragments of SEQ ID NO:3 and/or SEQ ID NO:5 can be provided. Such fragments can comprise at least 60%, at least 65%, at least 70%, at least 75%, at least 80%, at least 85%, at least 90%, at least 95%, at least 96%, at least 97%, at least 98%, or at least 99% of nucleic acids having 95% or greater identity to SEQ ID NO:3 and/or SEQ ID NO:5. Some embodiments relate to fragments that have 96% or greater identity to the fragments of proIL-33 nucleic acid sequences herein. Some embodiments relate to fragments that have 97% or greater identity to the fragments of proIL-33 nucleic acid sequences herein. Some embodiments relate to fragments that have 98% or greater identity to the fragments of proIL-33 nucleic acid sequences herein. Some embodiments relate to fragments that have 99% or greater identity to the fragments of proIL-33 nucleic acid sequences herein. In some embodiments, fragments include sequences that encode a leader sequence, for example, an immunoglobulin leader sequence such as the IgE leader sequence. In some embodiments, fragments are free of coding sequences that encode a leader sequence.

Fragments of SEQ ID NO:4 and/or SEQ ID NO:6 can be provided. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:4 and/or SEQ ID NO:6. In some embodiments, fragments include a leader sequence, for example, an immunoglobulin leader sequence such as the IgE leader sequence. In some embodiments, fragments are free of a leader sequence.

Fragments of proteins with amino acid sequences having identity to fragments of SEQ ID NO:4 and/or SEQ ID NO:6 can be provided. Such fragments can comprise at least 60%, at least 65%, at least 70%, at least 75%, at least 80%, at least 85%, at least 90%, at least 95%, at least 96%, at least 97%, at least 98%, or at least 99% of proteins having 95% or greater identity to SEQ ID NO:4 and/or SEQ ID NO:6. Some embodiments relate to fragments having 96% or greater identity to the fragments of proIL-33 protein sequences herein. Some embodiments relate to fragments having 97% or greater identity to the fragments of proIL-33 protein sequences herein. Some embodiments relate to fragments having 98% or greater identity to the fragments of proIL-33 protein sequences herein. Some embodiments relate to fragments having 99% or greater identity to the fragments of proIL-33 protein sequences herein. In some embodiments, fragments include a leader sequence, for example, an immunoglobulin leader sequence such as the IgE leader sequence. In some embodiments, the fragments are free of a leader sequence.

(b) MtrIL-33

IL-33 can be mtrIL-33, fragments thereof, or variants thereof. MtrIL-33 is mature or truncated IL-33 and lacks the CBD and NLS. MtrIL-33 is localized in the cytosol.

MtrIL-33 can increase or boost the immune response as described above for IL-33. MtrIL-33 can also increase or boost the cellular immune response to the antigen in the subject as described above for IL-33.

A nucleic acid encoding mtrIL-33 can be from any number of organism, for example, mouse (*Mus musculus*) and human (*Homo sapiens*). The nucleic acid encoding mtrIL-33 can be optimized with regards to codon usage and corresponding RNA transcripts. The nucleic acid encoding mtrIL-33 can also be codon and RNA optimized for expression. In some embodiments, the nucleic acid encoding mtrIL-33 can include a Kozak sequence (e.g., GCC ACC) to increase the efficiency of translation. The nucleic acid encoding mtrIL-33 can include multiple stop codons (e.g., TGA TGA) to increase the efficiency of translation termination. The nucleic acid encoding mtrIL-33 can also include a nucleotide sequence encoding an IgE leader sequence. The IgE leader sequence can be located 5' to mtrIL-33 in the nucleic acid. In some embodiments, the nucleic acid encoding mtrIL-33 is free of or does not contain a nucleotide sequence encoding the IgE leader sequence.

The mouse mtrIL-33 can be the optimized nucleic acid sequence SEQ ID NO:7, which encodes SEQ ID NO:8. In some embodiments, the mouse mtrIL-33 can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:7. In other embodiments, the mouse mtrIL-33 can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:8. The mouse mtrIL-33 can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:8.

The human mtrIL-33 can be the optimized nucleic acid sequence SEQ ID NO:1, which encodes SEQ ID NO:2. In some embodiments, the human mtrIL-33 can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:1. In other embodiments, the human mtrIL-33 can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2. The human mtrIL-33 can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2.

Some embodiments relate to fragments of SEQ ID NO:1 and/or SEQ ID NO:7. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:1 and/or SEQ ID NO:7. In some embodiments, fragments can include sequences that encode a leader sequence, for example, an immunoglobulin leader sequence, such as the IgE leader sequence. In some embodiments, fragments are free of coding sequences that encode a leader sequence.

Fragments of nucleic acids with nucleotide sequences having identity to fragments of SEQ ID NO:1 and/or SEQ ID NO:7 can be provided. Such fragments can comprise at least 60%, at least 65%, at least 70%, at least 75%, at least 80%, at least 85%, at least 90%, at least 95%, at least 96%, at least 97%, at least 98%, or at least 99% of nucleic acids having 95% or greater identity to SEQ ID NO:1 and/or SEQ ID NO:7. Some embodiments relate to fragments that have 96% or greater identity to the fragments of mtrIL-33 nucleic acid sequences herein. Some embodiments relate to fragments that have 97% or greater identity to the fragments of mtrIL-33 nucleic acid sequences herein. Some embodiments relate to fragments that have 98% or greater identity to the fragments of mtrIL-33 nucleic acid sequences herein. Some embodiments relate to fragments that have 99% or greater identity to the fragments of mtrIL-33 nucleic acid sequences herein. In some embodiments, fragments include sequences that encode a leader sequence, for example, an immunoglobulin leader sequence such as the IgE leader sequence. In some embodiments, fragments are free of coding sequences that encode a leader sequence.

Fragments of SEQ ID NO:2 and/or SEQ ID NO:8 can be provided. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:2 and/or SEQ ID NO:8. In some embodiments, fragments include a leader sequence, for example, an immunoglobulin leader sequence such as the IgE leader sequence. In some embodiments, fragments are free of a leader sequence.

Fragments of proteins with amino acid sequences having identity to fragments of SEQ ID NO:2 and/or SEQ ID NO:8 can be provided. Such fragments can comprise at least 60%, at least 65%, at least 70%, at least 75%, at least 80%, at least 85%, at least 90%, at least 95%, at least 96%, at least 97%, at least 98%, or at least 99% of proteins having 95% or greater identity to SEQ ID NO:2 and/or SEQ ID NO:8. Some embodiments relate to fragments having 96% or greater identity to the fragments of mtrIL-33 protein sequences herein. Some embodiments relate to fragments having 97% or greater identity to the fragments of mtrIL-33 protein sequences herein. Some embodiments relate to fragments having 98% or greater identity to the fragments of mtrIL-33 protein sequences herein. Some embodiments relate to fragments having 99% or greater identity to the fragments of mtrIL-33 protein sequences herein. In some embodiments, fragments include a leader sequence, for example, an immunoglobulin leader sequence such as the IgE leader sequence. In some embodiments, the fragments are free of a leader sequence.

b. Antigen

The vaccine can also comprise an antigen or fragment or variant thereof and the adjuvant as discussed above. The antigen can be anything that induces an immune response in a subject. Purified antigens are not usually strongly immunogenic on their own and are therefore combined with the adjuvant as described above. The immune response induced by the antigen can be boosted or increased when combined with the adjuvant. Such an immune response can be a humoral immune response and/or a cellular immune response. In some embodiments, the combination of the adjuvant and the antigen can boost or increase a cellular immune response in the subject.

The antigen can be a nucleic acid sequence, an amino acid sequence, or a combination thereof. The nucleic acid sequence can be DNA, RNA, cDNA, a variant thereof, a fragment thereof, or a combination thereof. The nucleic acid sequence can also include additional sequences that encode linker or tag sequences that are linked to the antigen by a peptide bond. The amino acid sequence can be a protein, a peptide, a variant thereof, a fragment thereof, or a combination thereof.

The antigen can be contained in a protein, a nucleic acid, or a fragment thereof, or a variant thereof, or a combination thereof from any number of organisms, for example, a virus, a parasite, a bacterium, a fungus, or a mammal. The antigen can be associated with an autoimmune disease, allergy, or asthma. In other embodiments, the antigen can be associated with cancer, herpes, influenza, hepatitis B, hepatitis C, human papilloma virus (HPV), or human immunodeficiency virus (HIV). Preferably, the antigen can be associated with influenza or HIV.

Some antigens can induce a strong immune response. Other antigens can induce a weak immune response. The antigen can elicit a greater immune response when combined with the adjuvant as described above.

(1) Viral Antigens

The antigen can be a viral antigen, or fragment thereof, or variant thereof. The viral antigen can be from a virus from one of the following families: Adenoviridae, Arenaviridae, Bunyaviridae, Caliciviridae, Coronaviridae, Filoviridae, Hepadnaviridae, Herpesviridae, Orthomyxoviridae, Papovaviridae, Paramyxoviridae, Parvoviridae, Picornaviridae, Poxviridae, Reoviridae, Retroviridae, Rhabdoviridae, or Togaviridae. The viral antigen can be from papilloma viruses, for example, human papillomoa virus (HPV), human immunodeficiency virus (HIV), polio virus, hepatitis B virus, hepatitis C virus, smallpox virus (Variola major and minor), vaccinia virus, influenza virus, rhinoviruses, dengue fever virus, equine encephalitis viruses, rubella virus, yellow fever virus, Norwalk virus, hepatitis A virus, human T-cell leukemia virus (HTLV-I), hairy cell leukemia virus (HTLV-II), California encephalitis virus, Hanta virus (hemorrhagic fever), rabies virus, Ebola fever virus, Marburg virus, measles virus, mumps virus, respiratory syncytial virus (RSV), herpes simplex 1 (oral herpes), herpes simplex 2 (genital herpes), herpes zoster (varicella-zoster, a.k.a., chickenpox), cytomegalovirus (CMV), for example human CMV, Epstein-Barr virus (EBV), flavivirus, foot and mouth disease virus, chikungunya virus, lassa virus, arenavirus, lymphocytic choriomeningitis virus (LCMV), or cancer causing virus.

(a) Hepatitis Antigen

IL-33 can be associated or combined with a hepatitis virus antigen (i.e., hepatitis antigen), or fragment thereof, or variant thereof. The hepatitis antigen can be an antigen or immunogen from hepatitis A virus (HAV), hepatitis B virus (HBV), hepatitis C virus (HCV), hepatitis D virus (HDV), and/or hepatitis E virus (HEV). In some embodiments, the hepatitis antigen can be a heterologous nucleic acid molecule(s), such as a plasmid(s), which encodes one or more of the antigens from HAV, HBV, HCV, HDV, and HEV. The hepatitis antigen can be full-length or immunogenic fragments of full-length proteins.

The hepatitis antigen can comprise consensus sequences and/or one or more modifications for improved expression. Genetic modifications, including codon optimization, RNA optimization, and the addition of a highly efficient immunoglobulin leader sequence to increase the immunogenicity of the constructs, can be included in the modified consensus sequences. The consensus hepatitis antigen may comprise a signal peptide such as an immunoglobulin signal peptide such as an IgE or IgG signal peptide, and in some embodiments, may comprise an HA tag. The immunogens can be designed to elicit stronger and broader cellular immune responses than corresponding codon optimized immunogens.

The hepatitis antigen can be an antigen from HAV. The hepatitis antigen can be a HAV capsid protein, a HAV non-structural protein, a fragment thereof, a variant thereof, or a combination thereof.

The hepatitis antigen can be an antigen from HCV. The hepatitis antigen can be a HCV nucleocapsid protein (i.e., core protein), a HCV envelope protein (e.g., E1 and E2), a HCV non-structural protein (e.g., NS1, NS2, NS3, NS4a, NS4b, NS5a, and NS5b), a fragment thereof, a variant thereof, or a combination thereof.

The hepatitis antigen can be an antigen from HDV. The hepatitis antigen can be a HDV delta antigen, fragment thereof, or variant thereof.

The hepatitis antigen can be an antigen from HEV. The hepatitis antigen can be a HEV capsid protein, fragment thereof, or variant thereof.

The hepatitis antigen can be an antigen from HBV. The hepatitis antigen can be a HBV core protein, a HBV surface protein, a HBV DNA polymerase, a HBV protein encoded by gene X, fragment thereof, variant thereof, or combination thereof. The hepatitis antigen can be a HBV genotype A core protein, a HBV genotype B core protein, a HBV genotype C core protein, a HBV genotype D core protein, a HBV genotype E core protein, a HBV genotype F core protein, a HBV genotype G core protein, a HBV genotype H core protein, a HBV genotype A surface protein, a HBV genotype B surface protein, a HBV genotype C surface protein, a HBV genotype D surface protein, a HBV genotype E surface protein, a HBV genotype F surface protein, a HBV genotype G surface protein, a HBV genotype H surface protein, fragment thereof, variant thereof, or combination thereof. The hepatitis antigen can be a consensus HBV core protein, or a consensus HBV surface protein.

In some embodiments, the hepatitis antigen can be a HBV genotype A consensus core DNA sequence construct, an IgE leader sequence linked to a consensus sequence for HBV genotype A core protein, or a HBV genotype A consensus core protein sequence.

In other embodiments, the hepatitis antigen can be a HBV genotype B consensus core DNA sequence construct, an IgE leader sequence linked to a consensus sequence for HBV genotype B core protein, or a HBV genotype B consensus core protein sequence.

In still other embodiments, the hepatitis antigen can be a HBV genotype C consensus core DNA sequence construct, an IgE leader sequence linked to a consensus sequence for HBV genotype C core protein, or a HBV genotype C consensus core protein sequence.

In some embodiments, the hepatitis antigen can be a HBV genotype D consensus core DNA sequence construct, an IgE leader sequence linked to a consensus sequence for HBV genotype D core protein, or a HBV genotype D consensus core protein sequence.

In other embodiments, the hepatitis antigen can be a HBV genotype E consensus core DNA sequence construct, an IgE leader sequence linked to a consensus sequence for HBV genotype E core protein, or a HBV genotype E consensus core protein sequence.

In some embodiments, the hepatitis antigen can be a HBV genotype F consensus core DNA sequence construct, an IgE leader sequence linked to a consensus sequence for HBV genotype F core protein, or a HBV genotype F consensus core protein sequence.

In other embodiments, the hepatitis antigen can be a HBV genotype G consensus core DNA sequence construct, an IgE leader sequence linked to a consensus sequence for HBV genotype G core protein, or a HBV genotype G consensus core protein sequence.

In some embodiments, the hepatitis antigen can be a HBV genotype H consensus core DNA sequence construct, an IgE leader sequence linked to a consensus sequence for HBV genotype H core protein, or a HBV genotype H consensus core protein sequence.

In still other embodiments, the hepatitis antigen can be a HBV genotype A consensus surface DNA sequence construct, an IgE leader sequence linked to a consensus sequence for HBV genotype A surface protein, or a HBV genotype A consensus surface protein sequence.

In some embodiments, the hepatitis antigen can be a HBV genotype B consensus surface DNA sequence construct, an IgE leader sequence linked to a consensus sequence for HBV genotype B surface protein, or a HBV genotype B consensus surface protein sequence.

In other embodiments, the hepatitis antigen can be a HBV genotype C consensus surface DNA sequence construct, an IgE leader sequence linked to a consensus sequence for HBV genotype C surface protein, or a HBV genotype C consensus surface protein sequence.

In still other embodiments, the hepatitis antigen can be a HBV genotype D consensus surface DNA sequence construct, an IgE leader sequence linked to a consensus sequence for HBV genotype D surface protein, or a HBV genotype D consensus surface protein sequence.

In some embodiments, the hepatitis antigen can be a HBV genotype E consensus surface DNA sequence construct, an IgE leader sequence linked to a consensus sequence for HBV genotype E surface protein, or a HBV genotype E consensus surface protein sequence.

In other embodiments, the hepatitis antigen can be a HBV genotype F consensus surface DNA sequence construct, an IgE leader sequence linked to a consensus sequence for HBV genotype F surface protein, or a HBV genotype F consensus surface protein sequence.

In still other embodiments, the hepatitis antigen can be a HBV genotype G consensus surface DNA sequence construct, an IgE leader sequence linked to a consensus sequence for HBV genotype G surface protein, or a HBV genotype G consensus surface protein sequence.

In other embodiments, the hepatitis antigen can be a HBV genotype H consensus surface DNA sequence construct, an IgE leader sequence linked to a consensus sequence for HBV genotype H surface protein, or a HBV genotype H consensus surface protein sequence.

(b) Human Papilloma Virus (HPV) Antigen

IL-33 can be associated or combined with a human papilloma virus (HPV) antigen, or fragment thereof, or variant thereof. The HPV antigen can be from HPV types 16, 18, 31, 33, 35, 45, 52, and 58 which cause cervical cancer, rectal cancer, and/or other cancers. The HPV antigen can be from HPV types 6 and 11, which cause genital warts, and are known to be causes of head and neck cancer.

The HPV antigens can be the HPV E6 or E7 domains from each HPV type. For example, for HPV type 16 (HPV16), the HPV16 antigen can include the HPV16 E6 antigen, the HPV16 E7 antigen, fragments, variants, or combinations thereof. Similarly, the HPV antigen can be HPV 6 E6 and/or E7, HPV 11 E6 and/or E7, HPV 18 E6 and/or E7, HPV 31 E6 and/or E7, HPV 33 E6 and/or E7, HPV 52 E6 and/or E7, or HPV 58 E6 and/or E7, fragments, variants, or combinations thereof.

(c) RSV Antigen

IL-33 can also be associated or combined with an RSV antigen or fragment thereof, or variant thereof. The RSV antigen can be a human RSV fusion protein (also referred to herein as "RSV F", "RSV F protein" and "F protein"), or fragment or variant thereof. The human RSV fusion protein can be conserved between RSV subtypes A and B. The RSV antigen can be a RSV F protein, or fragment or variant thereof, from the RSV Long strain (GenBank AAX23994.1). The RSV antigen can be a RSV F protein from the RSV A2 strain (GenBank AAB59858.1), or a fragment or variant thereof. The RSV antigen can be a monomer, a dimer or trimer of the RSV F protein, or a fragment or variant thereof. The RSV antigen can be an optimized amino acid RSV F amino acid sequence, or fragment or variant thereof.

The postfusion form of RSV F elicits high titer neutralizing antibodies in immunized animals and protects the animals from RSV challenge. The present invention utilizes this immunoresponse in the claimed vaccines. According to the invention, the RSV F protein can be in a prefusion form or a postfusion form.

The RSV antigen can also be human RSV attachment glycoprotein (also referred to herein as "RSV G", "RSV G protein" and "G protein"), or fragment or variant thereof. The human RSV G protein differs between RSV subtypes A and B. The antigen can be RSV G protein, or fragment or variant thereof, from the RSV Long strain (GenBank AAX23993). The RSV antigen can be RSV G protein from: the RSV subtype B isolate H5601, the RSV subtype B isolate H1068, the RSV subtype B isolate H5598, the RSV subtype B isolate H1123, or a fragment or variant thereof. The RSV antigen can be an optimized amino acid RSV G amino acid sequence, or fragment or variant thereof.

In other embodiments, the RSV antigen can be human RSV non-structural protein 1 ("NS1 protein"), or fragment or variant thereof. For example, the RSV antigen can be a RSV NS1 protein, or fragment or variant thereof, from the RSV Long strain (GenBank AAX23987.1). The RSV antigen human can also be RSV non-structural protein 2 ("NS2 protein"), or fragment or variant thereof. For example, the RSV antigen can be RSV NS2 protein, or fragment or variant thereof, from the RSV Long strain (GenBank AAX23988.1). The RSV antigen can further be human RSV nucleocapsid ("N") protein, or fragment or variant thereof. For example, the RSV antigen can be RSV N protein, or fragment or variant thereof, from the RSV Long strain (GenBank AAX23989.1). The RSV antigen can be human RSV Phosphoprotein ("P") protein, or fragment or variant thereof. For example, the RSV antigen can be RSV P protein, or fragment or variant thereof, from the RSV Long strain (GenBank AAX23990.1). The RSV antigen also can be human RSV Matrix protein ("M") protein, or fragment or variant thereof. For example, the RSV antigen can be RSV M protein, or fragment or variant thereof, from the RSV Long strain (GenBank AAX23991.1).

In still other embodiments, the RSV antigen can be human RSV small hydrophobic ("SH") protein, or fragment or variant thereof. For example, the RSV antigen can be RSV SH protein, or fragment or variant thereof, from the RSV Long strain (GenBank AAX23992.1). The RSV antigen can also be human RSV Matrix protein2-1 ("M2-1") protein, or fragment or variant thereof. For example, the RSV antigen can be RSV M2-1 protein, or fragment or variant thereof, from the RSV Long strain (GenBank AAX23995.1). The RSV antigen can further be human RSV Matrix protein 2-2 ("M2-2") protein, or fragment or variant thereof. For example, the RSV antigen can be RSV M2-2 protein, or fragment or variant thereof, from the RSV Long strain (GenBank AAX23997.1). The RSV antigen human can be RSV Polymerase L ("L") protein, or fragment or variant thereof. For example, the RSV antigen can be RSV L protein, or fragment or variant thereof, from the RSV Long strain (GenBank AAX23996.1).

In further embodiments, the RSV antigen can have an optimized amino acid sequence of NS1, NS2, N, P, M, SH, M2-1, M2-2, or L protein. The RSV antigen can be a human RSV protein or recombinant antigen, such as any one of the proteins encoded by the human RSV genome.

In other embodiments, the RSV antigen can be, but is not limited to, the RSV F protein from the RSV Long strain, the RSV G protein from the RSV Long strain, the optimized amino acid RSV G amino acid sequence, the human RSV genome of the RSV Long strain, the optimized amino acid RSV F amino acid sequence, the RSV NS1 protein from the RSV Long strain, the RSV NS2 protein from the RSV Long strain, the RSV N protein from the RSV Long strain, the RSV P protein from the RSV Long strain, the RSV M protein from the RSV Long strain, the RSV SH protein from the RSV Long strain, the RSV M2-1 protein from the RSV Long strain, the RSV M2-2 protein from the RSV Long strain, the RSV L protein from the RSV Long strain, the RSV G protein from the RSV subtype B isolate H5601, the RSV G protein from the RSV subtype B isolate H1068, the RSV G protein from the RSV subtype B isolate H5598, the RSV G protein from the RSV subtype B isolate H1123, or fragment thereof, or variant thereof.

(d) Influenza Antigen

IL-33 can be associated or combined with an influenza antigen or fragment thereof, or variant thereof. The influenza antigens are those capable of eliciting an immune response in a mammal against one or more influenza serotypes. The antigen can comprise the full length translation product HA0, subunit HA1, subunit HA2, a variant thereof, a fragment thereof or a combination thereof. The influenza hemagglutinin antigen can be a consensus sequence derived from multiple strains of influenza A serotype H1, a consensus sequence derived from multiple strains of influenza A serotype H2, a hybrid sequence containing portions of two different consensus sequences derived from different sets of multiple strains of influenza A serotype H1 or a consensus sequence derived from multiple strains of influenza B. The influenza hemagglutinin antigen can be from influenza B.

The influenza antigen can also contain at least one antigenic epitope that can be effective against particular influenza immunogens against which an immune response can be induced. The antigen may provide an entire repertoire of immunogenic sites and epitopes present in an intact influenza virus. The antigen may be a consensus hemagglutinin antigen sequence that can be derived from hemagglutinin antigen sequences from a plurality of influenza A virus strains of one serotype such as a plurality of influenza A virus strains of serotype H1 or of serotype H2. The antigen may be a hybrid consensus hemagglutinin antigen sequence that can be derived from combining two different consensus hemagglutinin antigen sequences or portions thereof. Each of two different consensus hemagglutinin antigen sequences may be derived from a different set of a plurality of influenza A virus strains of one serotype such as a plurality of influenza A virus strains of serotype H1. The antigen may be a consensus hemagglutinin antigen sequence that can be derived from hemagglutinin antigen sequences from a plurality of influenza B virus strains.

In some embodiments, the influenza antigen can be H1 HA, H2 HA, H3 HA, H5 HA, or a BHA antigen. Alternatively, the influenza antigen can be a consensus hemagglutinin antigen comprising a consensus H1 amino acid sequence or a consensus H2 amino acid sequence. The consensus hemagglutinin antigen may be a synthetic hybrid consensus H1 sequence comprising portions of two different consensus H1 sequences, which are each derived from a different set of sequences from the other. An example of a consensus HA antigen that is a synthetic hybrid consensus H1 protein is a protein comprising the U2 amino acid sequence. The consensus hemagglutinin antigen may be a consensus hemagglutinin protein derived from hemagglutinin sequences from influenza B strains, such as a protein comprising the consensus BHA amino acid sequence.

The consensus hemagglutinin antigen may further comprise one or more additional amino acid sequence elements. The consensus hemagglutinin antigen may further comprise on its N-terminus an IgE or IgG leader amino acid sequence. The consensus hemagglutinin antigen may further comprise an immunogenic tag which is a unique immunogenic epitope that can be detected by readily available antibodies. An example of such an immunogenic tag is the 9 amino acid influenza HA Tag which may be linked on the consensus hemagglutinin C terminus. In some embodiments, consensus hemagglutinin antigen may further comprise on its N-terminus an IgE or IgG leader amino acid sequence and on its C terminus an HA tag.

The consensus hemagglutinin antigen may be a consensus hemagglutinin protein that consists of consensus influenza amino acid sequences or fragments and variants thereof. The consensus hemagglutinin antigen may be a consensus hemagglutinin protein that comprises non-influenza protein sequences and influenza protein sequences or fragments and variants thereof.

Examples of a consensus H1 protein include those that may consist of the consensus H1 amino acid sequence or those that further comprise additional elements such as an IgE leader sequence, or an HA Tag or both an IgE leader sequence and an HA Tag.

Examples of consensus H2 proteins include those that may consist of the consensus H2 amino acid sequence or those that further comprise an IgE leader sequence, or an HA Tag, or both an IgE leader sequence and an HA Tag.

Examples of hybrid consensus H1 proteins include those that may consist of the consensus U2 amino acid sequence or those that further comprise an IgE leader sequence, or an HA Tag, or both an IgE leader sequence and an HA Tag.

Examples of hybrid consensus influenza B hemagglutinin proteins include those that may consist of the consensus BHA amino acid sequence or it may comprise an IgE leader sequence, or an HA Tag, or both an IgE leader sequence and an HA Tag.

The consensus hemagglutinin protein can be encoded by a consensus hemagglutinin nucleic acid, a variant thereof or a fragment thereof. Unlike the consensus hemagglutinin protein which may be a consensus sequence derived from a plurality of different hemagglutinin sequences from different strains and variants, the consensus hemagglutinin nucleic acid refers to a nucleic acid sequence that encodes a consensus protein sequence and the coding sequences used may differ from those used to encode the particular amino acid sequences in the plurality of different hemagglutinin sequences from which the consensus hemagglutinin protein sequence is derived. The consensus nucleic acid sequence may be codon optimized and/or RNA optimized. The consensus hemagglutinin nucleic acid sequence may comprise a Kozak's sequence in the 5' untranslated region. The consensus hemagglutinin nucleic acid sequence may comprise nucleic acid sequences that encode a leader sequence. The coding sequence of an N terminal leader sequence is 5' of the hemagglutinin coding sequence. The N-terminal leader can facilitate secretion. The N-terminal leader can be an IgE leader or an IgG leader. The consensus hemagglutinin nucleic acid sequence can comprise nucleic acid sequences that encode an immunogenic tag. The immunogenic tag can be on the C terminus of the protein and the sequence encoding it is 3' of the HA coding sequence. The immunogenic tag provides a unique epitope for which there are readily available antibodies so that such antibodies can be used in assays to detect and confirm expression of the protein. The immunogenic tag can be an HA Tag at the C-terminus of the protein.

(e) Human Immunodeficiency Virus (HIV) Antigen

IL-33 can be associated or combined with an HIV antigen or fragment thereof, or variant thereof. HIV antigens can include modified consensus sequences for immunogens. Genetic modifications including codon optimization, RNA optimization, and the addition of a high efficient immunoglobin leader sequence to increase the immunogenicity of constructs can be included in the modified consensus sequences. The novel immunogens can be designed to elicit stronger and broader cellular immune responses than corresponding codon optimized immunogens.

In some embodiments, the HIV antigen can be a subtype A consensus envelope DNA sequence construct, an IgE leader sequence linked to a consensus sequence for Subtype A envelope protein, or a subtype A consensus Envelope protein sequence.

In other embodiments, the HIV antigen can be a subtype B consensus envelope DNA sequence construct, an IgE leader sequence linked to a consensus sequence for Subtype B envelope protein, or an subtype B consensus Envelope protein sequence.

In still other embodiments, the HIV antigen can be a subtype C consensus envelope DNA sequence construct, an IgE leader sequence linked to a consensus sequence for subtype C envelope protein, or a subtype C consensus envelope protein sequence.

In further embodiments, the HIV antigen can be a subtype D consensus envelope DNA sequence construct, an IgE leader sequence linked to a consensus sequence for Subtype D envelope protein, or a subtype D consensus envelope protein sequence.

In some embodiments, the HIV antigen can be a subtype B Nef-Rev consensus envelope DNA sequence construct, an IgE leader sequence linked to a consensus sequence for Subtype B Nef-Rev protein, or a Subtype B Nef-Rev consensus protein sequence.

In other embodiments, the HIV antigen can be a Gag consensus DNA sequence of subtype A, B, C and D DNA sequence construct, an IgE leader sequence linked to a consensus sequence for Gag consensus subtype A, B, C and D protein, or a consensus Gag subtype A, B, C and D protein sequence.

In still other embodiments, the HIV antigen can be a MPol DNA sequence or a MPol protein sequence. The HIV antigen can be nucleic acid or amino acid sequences of Env A, Env B, Env C, Env D, B Nef-Rev, Gag, or any combination thereof.

(f) Lymphocytic Choriomeningitis Virus (LCMV) Antigen

IL-33 can be associated or combined with an LCMV antigen or fragment thereof, or variant thereof. The LCMV antigen can comprise consensus sequences and/or one or more modifications for improved expression. Genetic modifications, including codon optimization, RNA optimization, and the addition of a highly efficient immunoglobulin leader sequence to increase the immunogenicity of constructs, can be included in the modified sequences. The LCMV antigen can comprise a signal peptide such as an immunoglobulin signal peptide (e.g., IgE or IgG signal peptide), and in some embodiments, may comprise an HA tag. The immunogens can be designed to elicit stronger and broader cellular immune responses than a corresponding codon optimized immunogen.

The LCMV antigen can be an antigen from LCMV Armstrong. The LCMV antigen can be an antigen from LCMV clone 13. The LCMV antigen can be a nucleoprotein (NP) from LCMV, a glycoprotein (GP; e.g., GP-1, GP-2, and GP-C) from LCMV, a L protein from LCMV, a Z polypeptide from LCMV, a fragment thereof, a variant thereof, or a combination thereof.

(2) Parasite Antigens

The antigen can be a parasite antigen or fragment or variant thereof. The parasite can be a protozoa, helminth, or ectoparasite. The helminth (i.e., worm) can be a flatworm (e.g., flukes and tapeworms), a thorny-headed worm, or a round worm (e.g., pinworms). The ectoparasite can be lice, fleas, ticks, and mites.

The parasite can be any parasite causing the following diseases: Acanthamoeba keratitis, Amoebiasis, Ascariasis, Babesiosis, Balantidiasis, Baylisascariasis, Chagas disease, Clonorchiasis, *Cochliomyia*, Cryptosporidiosis, Diphyllobothriasis, Dracunculiasis, Echinococcosis, Elephantiasis, Enterobiasis, Fascioliasis, Fasciolopsiasis, Filariasis, Giardiasis, Gnathostomiasis, Hymenolepiasis, Isosporiasis, Katayama fever, Leishmaniasis, Lyme disease, Malaria, Metagonimiasis, Myiasis, Onchocerciasis, Pediculosis, Scabies, Schistosomiasis, Sleeping sickness, Strongyloidiasis, Taeniasis, Toxocariasis, Toxoplasmosis, Trichinosis, and Trichuriasis.

The parasite can be Acanthamoeba, Anisakis, *Ascaris lumbricoides*, Botfly, *Balantidium coli*, Bedbug, *Cestoda* (tapeworm), Chiggers, *Cochliomyia hominivorax*, Entamoeba histolytica, *Fasciola hepatica, Giardia lamblia*, Hookworm, *Leishmania, Linguatula serrata*, Liver fluke, Loa loa, *Paragonimus*—lung fluke, Pinworm, *Plasmodium falciparum*, Schistosoma, *Strongyloides stercoralis*, Mite, Tapeworm, *Toxoplasma gondii, Trypanosoma*, Whipworm, or *Wuchereria bancrofti*.

(a) Malaria Antigen

IL-33 can be associated or combined with a malaria antigen (i.e., PF antigen or PF immunogen), or fragment thereof, or variant thereof. The antigen can be from a parasite causing malaria. The malaria causing parasite can be *Plasmodium falciparum*. The *Plasmodium falciparum* antigen can include the circumsporozoite (CS) antigen.

In some embodiments, the malaria antigen can be nucleic acid molecules such as plasmids which encode one or more of the *P. falciparum* immunogens CS, LSA1, TRAP, CelTOS, and Ama1. The immunogens may be full length or immunogenic fragments of full length proteins. The immunogens comprise consensus sequences and/or modifications for improved expression.

In other embodiments, the malaria antigen can be a consensus sequence of TRAP, which is also referred to as SSP2, designed from a compilation of all full-length *Plasmodium falciparum* TRAP/SSP2 sequences in the GenBank database (28 sequences total). Consensus TRAP immunogens (i.e., ConTRAP immunogen) may comprise a signal peptide such as an immunoglobulin signal peptide such as an IgE or IgG signal peptide and in some embodiments, may comprise an HA tag.

In still other embodiments, the malaria antigen can be CelTOS, which is also referred to as Ag2 and is a highly conserved *Plasmodium* antigen. Consensus CelTOS antigens (i.e., ConCelTOS immunogen) may comprise a signal peptide such as an immunoglobulin signal peptide such as an IgE or IgG signal peptide and in some embodiments, may comprise an HA tag.

In further embodiments, the malaria antigen can be Ama1, which is a highly conserved *Plasmodium* antigen. The malaria antigen can also be a consensus sequence of Ama1 (i.e., ConAmaI immunogen) comprising in some instances, a signal peptide such as an immunoglobulin signal peptide such as an IgE or IgG signal peptide and in some embodiments, may comprise an HA tag.

In some embodiments, the malaria antigen can be a consensus CS antigen (i.e., Consensus CS immunogen) comprising in some instances, a signal peptide such as an immunoglobulin signal peptide such as an IgE or IgG signal peptide and in some embodiments, may comprise an HA tag.

In other embodiments, the malaria antigen can be a fusion protein comprising a combination of two or more of the PF proteins set forth herein. For example, fusion proteins may comprise two or more of Consensus CS immunogen, ConLSA1 immunogen, ConTRAP immunogen, ConCelTOS immunogen and ConAma1 immunogen linked directly adjacent to each other or linked with a spacer or one or more amino acids in between. In some embodiments, the fusion protein comprises two PF immunogens; in some embodiments the fusion protein comprises three PF immunogens; in some embodiments the fusion protein comprises four PF immunogens; and in some embodiments the fusion protein comprises five PF immunogens. Fusion proteins with two Consensus PF immunogens may comprise: CS and LSA1; CS and TRAP; CS and CelTOS; CS and Ama1; LSA1 and TRAP; LSA1 and CelTOS; LSA1 and Ama1; TRAP and CelTOS; TRAP and Ama1; or CelTOS and Ama1. Fusion proteins with three Consensus PF immunogens may comprise: CS, LSA1 and TRAP; CS, LSA1 and CelTOS; CS, LSA1 and Ama1; LSA1, TRAP and CelTOS; LSA1, TRAP and Ama1; or TRAP, CelTOS and Ama1. Fusion proteins with four Consensus PF immunogens may comprise: CS, LSA1, TRAP and CelTOS; CS, LSA1, TRAP and Ama1; CS, LSA1, CelTOS and Ama1; CS, TRAP, CelTOS and Ama1; or LSA1, TRAP, CelTOS and Ama1. Fusion proteins with five Consensus PF immunogens may comprise CS or CS-alt, LSA1, TRAP, CelTOS and Ama1.

In some embodiments, the fusion proteins comprise a signal peptide linked to the N terminus. In some embodiments, the fusion proteins comprise multiple signal peptides linked to the N terminus of each Consensus PF immunogen. In some embodiments, a spacer may be included between PF immunogens of a fusion protein. In some embodiments, the spacer between PF immunogens of a fusion protein may be a proteolyic cleavage site. In some embodiments, the spacer may be a proteolyic cleavage site recognized by a protease found in cells to which the vaccine is intended to be administered and/or taken up. In some embodiments, a spacer may be included between PF immunogens of a fusion protein, wherein the spacer is a proteolyic cleavage site recognized by a protease found in cells to which the vaccine is intended to be administered and/or taken up and the fusion protein comprises multiple signal peptides linked to the N terminus of each Consensus PF immunogens such that upon cleavage, the signal peptide of each Consensus PF immunogen translocates the Consensus PF immunogen to outside the cell.

(3) Bacterial Antigens

The antigen can be a bacterial antigen or fragment or variant thereof. The bacterium can be from any one of the following phyla: Acidobacteria, Actinobacteria, Aquificae, Bacteroidetes, Caldiserica, Chlamydiae, Chlorobi, Chloroflexi, Chrysiogenetes, Cyanobacteria, Deferribacteres, Deinococcus-Thermus, Dictyoglomi, Elusimicrobia, Fibrobacteres, Firmicutes, Fusobacteria, Gemmatimonadetes, Lentisphaerae, Nitrospira, Planctomycetes, Proteobacteria, Spirochaetes, Synergistetes, Tenericutes, Thermodesulfobacteria, Thermotogae, and Verrucomicrobia.

The bacterium can be a gram positive bacterium or a gram negative bacterium. The bacterium can be an aerobic bacterium or an anerobic bacterium. The bacterium can be an autotrophic bacterium or a heterotrophic bacterium. The bacterium can be a mesophile, a neutrophile, an extremophile, an acidophile, an alkaliphile, a thermophile, a psychrophile, an halophile, or an osmophile.

The bacterium can be an anthrax bacterium, an antibiotic resistant bacterium, a disease causing bacterium, a food poisoning bacterium, an infectious bacterium, *Salmonella* bacterium, *Staphylococcus* bacterium, *Streptococcus* bacterium, or tetanus bacterium. The bacterium can be a mycobacteria, *Clostridium tetani, Yersinia pestis, Bacillus* anthraces, methicillin-resistant *Staphylococcus aureus* (MRSA), or *Clostridium difficile*. The bacterium can be *Mycobacterium tuberculosis*.

(a) *Mycobacterium tuberculosis* Antigens

IL-33 can be associated or combined with a *Mycobacterium tuberculosis* antigen (i.e., TB antigen or TB immunogen), or fragment thereof, or variant thereof. The TB antigen can be from the Ag85 family of TB antigens, for example, Ag85A and Ag85B. The TB antigen can be from the Esx family of TB antigens, for example, EsxA, EsxB, EsxC, EsxD, EsxE, EsxF, EsxH, EsxO, EsxQ, EsxR, EsxS, EsxT, EsxU, EsxV, and EsxW.

In some embodiments, the TB antigen can be nucleic acid molecules such as plasmids which encode one or more of the *Mycobacterium tuberculosis* immunogens from the Ag85 family and the Esx family. The immunogens can be full-length or immunogenic fragments of full-length proteins. The immunogens can comprise consensus sequences and/or modifications for improved expression. Consensus immunogens may comprise a signal peptide such as an immunoglobulin signal peptide such as an IgE or IgG signal peptide and in some embodiments, may comprise an HA tag.

(4) Fungal Antigens

The antigen can be a fungal antigen or fragment or variant thereof. The fungus can be *Aspergillus* species, *Blastomyces dermatitides, Candida* yeasts (e.g., *Candida albicans*), *Coccidioides, Cryptococcus neoformans, Cryptococcus gattii*, dermatophyte, *Fusarium* species, *Histoplasma capsulatum*, Mucoromycotina, *Pneumocystis jirovecii, Sporothrix schenckii, Exserohilum*, or *Cladosporium*.

c. Vector

The vaccine can comprise one or more vectors that include a nucleic acid encoding the antigen and the adjuvant. The one or more vectors can be capable of expressing the antigen and the adjuvant. The one or more vectors can be an expression construct, which is generally a plasmid that is used to introduce a specific gene into a target cell. Once the expression vector is inside the cell, the protein that is encoded by the gene is produced by the cellular-transcription and translation machinery ribosomal complexes. The plasmid is frequently engineered to contain regulatory sequences that act as enhancer and promoter regions and lead to efficient transcription of the gene carried on the expression vector. The vectors of the present invention express large amounts of stable messenger RNA, and therefore proteins.

The vectors may have expression signals such as a strong promoter, a strong termination codon, adjustment of the distance between the promoter and the cloned gene, and the insertion of a transcription termination sequence and a PTIS (portable translation initiation sequence).

(1) Expression Vectors

The vector can be a circular plasmid or a linear nucleic acid. The circular plasmid and linear nucleic acid are capable of directing expression of a particular nucleotide sequence in an appropriate subject cell. The vector can have a promoter operably linked to the antigen-encoding nucleotide sequence, or the adjuvant-encoding nucleotide sequence, which may be operably linked to termination signals. The vector can also contain sequences required for proper translation of the nucleotide sequence. The vector comprising the nucleotide sequence of interest may be chimeric, meaning that at least one of its components is heterologous with respect to at least one of its other components. The expression of the nucleotide sequence in the expression cassette may be under the control of a constitutive promoter or of an inducible promoter, which initiates transcription only when the host cell is exposed to some particular external stimulus. In the case of a multicellular organism, the promoter can also be specific to a particular tissue or organ or stage of development.

(2) Circular and Linear Vectors

The vector may be a circular plasmid, which may transform a target cell by integration into the cellular genome or exist extrachromosomally (e.g., autonomous replicating plasmid with an origin of replication).

The vector can be pVAX, pcDNA3.0, or provax, or any other expression vector capable of expressing DNA encoding the antigen, or the adjuvant and enabling a cell to translate the sequence to an antigen that is recognized by the immune system, or the adjuvant.

Also provided herein is a linear nucleic acid vaccine, or linear expression cassette ("LEC"), that is capable of being efficiently delivered to a subject via electroporation and expressing one or more desired antigens, or one or more desired adjuvants. The LEC may be any linear DNA devoid of any phosphate backbone. The DNA may encode one or more antigens, or one or more adjuvants. The LEC may contain a promoter, an intron, a stop codon, and/or a polyadenylation signal. The expression of the antigen, or the adjuvant may be controlled by the promoter. The LEC may not contain any antibiotic resistance genes and/or a phosphate backbone. The LEC may not contain other nucleic acid sequences unrelated to the desired antigen gene expression, or the desired adjuvant expression.

The LEC may be derived from any plasmid capable of being linearized. The plasmid may be capable of expressing the antigen, or the adjuvant. The plasmid may be capable of expressing the adjuvant IL-33. The plasmid can be pNP (Puerto Rico/34) or pM2 (New Caledonia/99). The plasmid may be WLV009, pVAX, pcDNA3.0, or provax, or any other expression vector capable of expressing DNA encoding the antigen, or encoding the adjuvant, and enabling a cell to translate the sequence to an antigen that is recognized by the immune system, or the adjuvant.

The LEC can be perM2. The LEC can be perNP. perNP and perMR can be derived from pNP (Puerto Rico/34) and pM2 (New Caledonia/99), respectively.

(3) Promoter, Intron, Stop Codon, and Polyadenylation Signal

The vector may have a promoter. A promoter may be any promoter that is capable of driving gene expression and regulating expression of the isolated nucleic acid. Such a promoter is a cis-acting sequence element required for transcription via a DNA dependent RNA polymerase, which transcribes the antigen sequence, or the adjuvant sequence described herein. Selection of the promoter used to direct expression of a heterologous nucleic acid depends on the particular application. The promoter may be positioned about the same distance from the transcription start in the vector as it is from the transcription start site in its natural setting. However, variation in this distance may be accommodated without loss of promoter function.

The promoter may be operably linked to the nucleic acid sequence encoding the antigen and signals required for efficient polyadenylation of the transcript, ribosome binding sites, and translation termination. The promoter may be operably linked to the nucleic acid sequence encoding the adjuvant and signals required for efficient polyadenylation of the transcript, ribosome binding sites, and translation termination.

The promoter may be a CMV promoter, SV40 early promoter, SV40 later promoter, metallothionein promoter, murine mammary tumor virus promoter, Rous sarcoma virus promoter, polyhedrin promoter, or another promoter shown effective for expression in eukaryotic cells.

The vector may include an enhancer and an intron with functional splice donor and acceptor sites. The vector may contain a transcription termination region downstream of the structural gene to provide for efficient termination. The termination region may be obtained from the same gene as the promoter sequence or may be obtained from different genes.

d. Excipients and Other Components of the Vaccine

The vaccine may further comprise a pharmaceutically acceptable excipient. The pharmaceutically acceptable excipient can be functional molecules such as vehicles, adjuvants other than IL-33, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate may be present in the vaccine at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. The DNA plasmid vaccines may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be an adjuvant in addition to IL-33. The additional adjuvant can be other genes that are expressed in an alternative plasmid or are delivered as proteins in combination with the plasmid above in the vaccine. The adjuvant may be selected from the group consisting of: α-interferon (IFN-α), (β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

Other genes that can be useful as adjuvants in addition to IL-33 include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, IL-22, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAIL-recDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The vaccine may further comprise a genetic vaccine facilitator agent as described in U.S. Ser. No. 021,579 filed Apr. 1, 1994, which is fully incorporated by reference.

The vaccine can be formulated according to the mode of administration to be used. An injectable vaccine pharmaceutical composition can be sterile, pyrogen free and particulate free. An isotonic formulation or solution can be used. Additives for isotonicity can include sodium chloride, dextrose, mannitol, sorbitol, and lactose. The vaccine can comprise a vasoconstriction agent. The isotonic solutions can include phosphate buffered saline. The vaccine can further comprise stabilizers including gelatin and albumin.

The stabilizers can allow the formulation to be stable at room or ambient temperature for extended periods of time, including LGS or polycations or polyanions.

3. METHOD OF VACCINATION

The present invention is also directed to a method of increasing an immune response in a subject. Increasing the immune response can be used to treat and/or prevent disease in the subject, for example, cancer as described in more detail below. The method can include administering the herein disclosed vaccine to the subject. The subject administered the vaccine can have an increased or boosted immune response as compared to a subject administered the antigen alone. In some embodiments, the immune response can be increased by about 75% to about 200%. Alternatively, the immune response in the subject administered the vaccine can be increased by about 90% to about 130%. In still other alternative embodiments, the immune response in the subject administered the vaccine can be increased by about 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, or 130%.

In other embodiments, the immune response in the subject administered the vaccine can be increased by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, or at least about 10.0-fold.

The vaccine dose can be between 1 μg to 10 mg active component/kg body weight/time, and can be 20 μg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, or 10.

a. Treatment and Prevention of Cancer

The subject administered the vaccine can have an increased or boosted immune response as compared to the subject administered the antigen alone. The increased immune response can be used to treat and/or prevent disease in the subject. The disease can be cancer, for example, an HPV-associated cancer, HBV-associated cancer, ovarian cancer, prostate cancer, breast cancer, brain cancer, head and neck cancer, throat cancer, lung cancer, liver cancer, cancer of the pancreas, kidney cancer, bone cancer, melanoma, metastatic cancer, hTERT-associated cancer, FAP-antigen associated cancer, non-small cell lung cancer, blood cancer, esophageal squamous cell carcinoma, cervical cancer, bladder cancer, colorectal cancer, gastric cancer, anal cancer, synovial carcinoma, testicular cancer, recurrent respiratory papillomatosis, skin cancer, glioblastoma, hepatocarcinoma, stomach cancer, acute myeloid leukemia, triple-negative breast cancer, and primary cutaneous T cell lymphoma. The cancer can be HPV-associated cancer.

The method can further include reducing the size of an established tumor or lesion in the subject. The tumor can be reduced in size by about 50% to about 100%, about 60% to about 100%, about 70% to about 100%, about 80% to about 100%, about 90% to about 100%, about 50% to about 95%, about 60% to about 95%, about 70% to about 95%, about 80% to about 95%, about 90% to about 95%, about 50% to about 90%, about 60% to about 90%, about 70% to about 90%, or about 80% to about 90%. The tumor can be reduced in size by about 80%, by about 81%, by about 82%, by about 83%, by about 84%, by about 85%, by about 86%, by about 87%, by about 88%, by about 89%, by about 90%, by about 91%, by about 92%, by about 93%, by about 94%, by about 95%, by about 96%, by about 97%, by about 98%, by about 99%, or by about 100%.

The method can further include increasing tumor regression in the subject as compared to the subject administered the antigen alone. Administration of the vaccine can increase tumor regression by about 40% to about 60%, about 45% to about 55%, or about 50%. Administration of the vaccine can also increase the rate of tumor regression. Administration of the vaccine can further achieve tumor regression in the subject of about 80% to about 100%, about 85% to about 100%, about 90% to about 100%, about 95% to about 100%, about 80% to about 95%, about 85% to about 95%, about 90% to about 95%, about 80% to about 90%, or about 85% to about 90%. Tumor regression can be about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% in the subject administered the vaccine. Tumor regression in the subject administered the vaccine can further be about 90% or about 100%.

The method can further include preventing cancer or tumor growth in the subject administered the vaccine. This prevention can allow the subject administered the vaccine to survive a future cancer. In other words, the vaccine affords protection against cancer to the subject administered the vaccine. The subject administered the vaccine can have about 90% to about 100% survival of cancer. The subject administered the vaccine can have about 90%, about 91%, about 92%, about 93%, about 94%, about 95%, about 96%, about 97%, about 98%, about 99%, or about 100% survival of cancer.

b. Administration

The vaccine can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular subject, and the route of administration. The subject can be a mammal, such as a human, a horse, a cow, a pig, a sheep, a cat, a dog, a rat, or a mouse.

The vaccine can be administered prophylactically or therapeutically. In prophylactic administration, the vaccines can be administered in an amount sufficient to induce an immune response. In therapeutic applications, the vaccines are administered to a subject in need thereof in an amount sufficient to elicit a therapeutic effect. An amount adequate to accomplish this is defined as a "therapeutically effective dose." Amounts effective for this use will depend on, e.g., the particular composition of the vaccine regimen administered, the manner of administration, the stage and severity of the disease, the general state of health of the patient, and the judgment of the prescribing physician.

The vaccine can be administered by methods well known in the art as described in Donnelly et al. (Ann. Rev. Immunol. 15:617-648 (1997)); Felgner et al. (U.S. Pat. No. 5,580,859, issued Dec. 3, 1996); Felgner (U.S. Pat. No. 5,703,055, issued Dec. 30, 1997); and Carson et al. (U.S.

Pat. No. 5,679,647, issued Oct. 21, 1997), the contents of all of which are incorporated herein by reference in their entirety. The DNA of the vaccine can be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

The vaccine can be delivered via a variety of routes. Typical delivery routes include parenteral administration, e.g., intradermal, intramuscular or subcutaneous delivery. Other routes include oral administration, intranasal, and intravaginal routes. For the DNA of the vaccine in particular, the vaccine can be delivered to the interstitial spaces of tissues of an individual (Felgner et al., U.S. Pat. Nos. 5,580,859 and 5,703,055, the contents of all of which are incorporated herein by reference in their entirety). The vaccine can also be administered to muscle, or can be administered via intradermal or subcutaneous injections, or transdermally, such as by iontophoresis. Epidermal administration of the vaccine can also be employed. Epidermal administration can involve mechanically or chemically irritating the outermost layer of epidermis to stimulate an immune response to the irritant (Carson et al., U.S. Pat. No. 5,679,647, the contents of which are incorporated herein by reference in its entirety).

The vaccine can also be formulated for administration via the nasal passages. Formulations suitable for nasal administration, wherein the carrier is a solid, can include a coarse powder having a particle size, for example, in the range of about 10 to about 500 microns which is administered in the manner in which snuff is taken, i.e., by rapid inhalation through the nasal passage from a container of the powder held close up to the nose. The formulation can be a nasal spray, nasal drops, or by aerosol administration by nebulizer. The formulation can include aqueous or oily solutions of the vaccine.

The vaccine can be a liquid preparation such as a suspension, syrup or elixir. The vaccine can also be a preparation for parenteral, subcutaneous, intradermal, intramuscular or intravenous administration (e.g., injectable administration), such as a sterile suspension or emulsion.

The vaccine can be incorporated into liposomes, microspheres or other polymer matrices (Felgner et al., U.S. Pat. No. 5,703,055; Gregoriadis, Liposome Technology, Vols. I to III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

The vaccine can be administered via electroporation, such as by a method described in U.S. Pat. No. 7,664,545, the contents of which are incorporated herein by reference. The electroporation can be by a method and/or apparatus described in U.S. Pat. Nos. 6,302,874; 5,676,646; 6,241,701; 6,233,482; 6,216,034; 6,208,893; 6,192,270; 6,181,964; 6,150,148; 6,120,493; 6,096,020; 6,068,650; and 5,702,359, the contents of which are incorporated herein by reference in their entirety. The electroporation may be carried out via a minimally invasive device.

The minimally invasive electroporation device ("MID") may be an apparatus for injecting the vaccine described above and associated fluid into body tissue. The device may comprise a hollow needle, DNA cassette, and fluid delivery means, wherein the device is adapted to actuate the fluid delivery means in use so as to concurrently (for example, automatically) inject DNA into body tissue during insertion of the needle into the said body tissue. This has the advantage that the ability to inject the DNA and associated fluid gradually while the needle is being inserted leads to a more even distribution of the fluid through the body tissue. The pain experienced during injection may be reduced due to the distribution of the DNA being injected over a larger area.

The MID may inject the vaccine into tissue without the use of a needle. The MID may inject the vaccine as a small stream or jet with such force that the vaccine pierces the surface of the tissue and enters the underlying tissue and/or muscle. The force behind the small stream or jet may be provided by expansion of a compressed gas, such as carbon dioxide through a micro-orifice within a fraction of a second. Examples of minimally invasive electroporation devices, and methods of using them, are described in published U.S. Patent Application No. 20080234655; U.S. Pat. No. 6,520,950; U.S. Pat. No. 7,171,264; U.S. Pat. No. 6,208,893; U.S. Pat. No. 6,009,347; U.S. Pat. No. 6,120,493; U.S. Pat. No. 7,245,963; U.S. Pat. No. 7,328,064; and U.S. Pat. No. 6,763,264, the contents of each of which are herein incorporated by reference.

The MID may comprise an injector that creates a high-speed jet of liquid that painlessly pierces the tissue. Such needle-free injectors are commercially available. Examples of needle-free injectors that can be utilized herein include those described in U.S. Pat. Nos. 3,805,783; 4,447,223; 5,505,697; and 4,342,310, the contents of each of which are herein incorporated by reference.

A desired vaccine in a form suitable for direct or indirect electrotransport may be introduced (e.g., injected) using a needle-free injector into the tissue to be treated, usually by contacting the tissue surface with the injector so as to actuate delivery of a jet of the agent, with sufficient force to cause penetration of the vaccine into the tissue. For example, if the tissue to be treated is mucosa, skin or muscle, the agent is projected towards the mucosal or skin surface with sufficient force to cause the agent to penetrate through the stratum corneum and into dermal layers, or into underlying tissue and muscle, respectively.

Needle-free injectors are well suited to deliver vaccines to all types of tissues, particularly to skin and mucosa. In some embodiments, a needle-free injector may be used to propel a liquid that contains the vaccine to the surface and into the subject's skin or mucosa. Representative examples of the various types of tissues that can be treated using the invention methods include pancreas, larynx, nasopharynx, hypopharynx, oropharynx, lip, throat, lung, heart, kidney, muscle, breast, colon, prostate, thymus, testis, skin, mucosal tissue, ovary, blood vessels, or any combination thereof.

The MID may have needle electrodes that electroporate the tissue. By pulsing between multiple pairs of electrodes in a multiple electrode array, for example set up in rectangular or square patterns, provides improved results over that of pulsing between a pair of electrodes. Disclosed, for example, in U.S. Pat. No. 5,702,359 entitled "Needle Electrodes for Mediated Delivery of Drugs and Genes" is an array of needles wherein a plurality of pairs of needles may be pulsed during the therapeutic treatment. In that application, which is incorporated herein by reference as fully set forth, needles were disposed in a circular array, but have connectors and switching apparatus enabling a pulsing between opposing pairs of needle electrodes. A pair of needle electrodes for delivering recombinant expression vectors to cells may be used. Such a device and system is described in U.S. Pat. No. 6,763,264, the contents of which are herein incorporated by reference. Alternatively, a single needle device may be used that allows injection of the DNA and electroporation with a single needle resembling a normal injection needle and applies pulses of lower voltage than those delivered by presently used devices, thus reducing the electrical sensation experienced by the patient.

The MID may comprise one or more electrode arrays. The arrays may comprise two or more needles of the same diameter or different diameters. The needles may be evenly or unevenly spaced apart. The needles may be between 0.005 inches and 0.03 inches, between 0.01 inches and 0.025 inches; or between 0.015 inches and 0.020 inches. The needle may be 0.0175 inches in diameter. The needles may be 0.5 mm, 1.0 mm, 1.5 mm, 2.0 mm, 2.5 mm, 3.0 mm, 3.5 mm, 4.0 mm, or more spaced apart.

The MID may consist of a pulse generator and a two or more-needle vaccine injectors that deliver the vaccine and electroporation pulses in a single step. The pulse generator may allow for flexible programming of pulse and injection parameters via a flash card operated personal computer, as well as comprehensive recording and storage of electroporation and patient data. The pulse generator may deliver a variety of volt pulses during short periods of time. For example, the pulse generator may deliver three 15 volt pulses of 100 ms in duration. An example of such a MID is the Elgen 1000 system by Inovio Biomedical Corporation, which is described in U.S. Pat. No. 7,328,064, the contents of which are herein incorporated by reference.

The MID may be a CELLECTRA (Inovio Pharmaceuticals, Blue Bell Pa.) device and system, which is a modular electrode system, that facilitates the introduction of a macromolecule, such as a DNA, into cells of a selected tissue in a body or plant. The modular electrode system may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The macromolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the macromolecule into the cell between the plurality of electrodes. Cell death due to overheating of cells is minimized by limiting the power dissipation in the tissue by virtue of constant-current pulses. The Cellectra device and system is described in U.S. Pat. No. 7,245,963, the contents of which are herein incorporated by reference.

The MID may be an Elgen 1000 system (Inovio Pharmaceuticals). The Elgen 1000 system may comprise device that provides a hollow needle; and fluid delivery means, wherein the apparatus is adapted to actuate the fluid delivery means in use so as to concurrently (for example automatically) inject fluid, the described vaccine herein, into body tissue during insertion of the needle into the said body tissue. The advantage is the ability to inject the fluid gradually while the needle is being inserted leads to a more even distribution of the fluid through the body tissue. It is also believed that the pain experienced during injection is reduced due to the distribution of the volume of fluid being injected over a larger area.

In addition, the automatic injection of fluid facilitates automatic monitoring and registration of an actual dose of fluid injected. This data can be stored by a control unit for documentation purposes if desired.

It will be appreciated that the rate of injection could be either linear or non-linear and that the injection may be carried out after the needles have been inserted through the skin of the subject to be treated and while they are inserted further into the body tissue.

Suitable tissues into which fluid may be injected by the apparatus of the present invention include tumor tissue, skin or liver tissue but may be muscle tissue.

The apparatus further comprises needle insertion means for guiding insertion of the needle into the body tissue. The rate of fluid injection is controlled by the rate of needle insertion. This has the advantage that both the needle insertion and injection of fluid can be controlled such that the rate of insertion can be matched to the rate of injection as desired. It also makes the apparatus easier for a user to operate. If desired means for automatically inserting the needle into body tissue could be provided.

A user could choose when to commence injection of fluid. Ideally however, injection is commenced when the tip of the needle has reached muscle tissue and the apparatus may include means for sensing when the needle has been inserted to a sufficient depth for injection of the fluid to commence. This means that injection of fluid can be prompted to commence automatically when the needle has reached a desired depth (which will normally be the depth at which muscle tissue begins). The depth at which muscle tissue begins could for example be taken to be a preset needle insertion depth such as a value of 4 mm which would be deemed sufficient for the needle to get through the skin layer.

The sensing means may comprise an ultrasound probe. The sensing means may comprise a means for sensing a change in impedance or resistance. In this case, the means may not as such record the depth of the needle in the body tissue but will rather be adapted to sense a change in impedance or resistance as the needle moves from a different type of body tissue into muscle. Either of these alternatives provides a relatively accurate and simple to operate means of sensing that injection may commence. The depth of insertion of the needle can further be recorded if desired and could be used to control injection of fluid such that the volume of fluid to be injected is determined as the depth of needle insertion is being recorded.

The apparatus may further comprise: a base for supporting the needle; and a housing for receiving the base therein, wherein the base is moveable relative to the housing such that the needle is retracted within the housing when the base is in a first rearward position relative to the housing and the needle extends out of the housing when the base is in a second forward position within the housing. This is advantageous for a user as the housing can be lined up on the skin of a patient, and the needles can then be inserted into the patient's skin by moving the housing relative to the base.

As stated above, it is desirable to achieve a controlled rate of fluid injection such that the fluid is evenly distributed over the length of the needle as it is inserted into the skin. The fluid delivery means may comprise piston driving means adapted to inject fluid at a controlled rate. The piston driving means could for example be activated by a servo motor. However, the piston driving means may be actuated by the base being moved in the axial direction relative to the housing. It will be appreciated that alternative means for fluid delivery could be provided. Thus, for example, a closed container which can be squeezed for fluid delivery at a controlled or non-controlled rate could be provided in the place of a syringe and piston system.

The apparatus described above could be used for any type of injection. It is however envisaged to be particularly useful in the field of electroporation and so it may further comprise means for applying a voltage to the needle. This allows the needle to be used not only for injection but also as an electrode during electroporation. This is particularly advantageous as it means that the electric field is applied to the same area as the injected fluid. There has traditionally been a problem with electroporation in that it is very difficult to accurately align an electrode with previously injected fluid and so users have tended to inject a larger volume of fluid than is required over a larger area and to apply an electric field over a higher area to attempt to guarantee an overlap between the injected substance and the electric field. Using the present invention, both the volume of fluid injected and the size of electric field applied may be reduced while achieving a good fit between the electric field and the fluid.

The present invention has multiple aspects, illustrated by the following non-limiting examples.

4. EXAMPLES

Example 1

Materials and Methods for Examples 2-10

Plasmid Construction.

Figure 10:
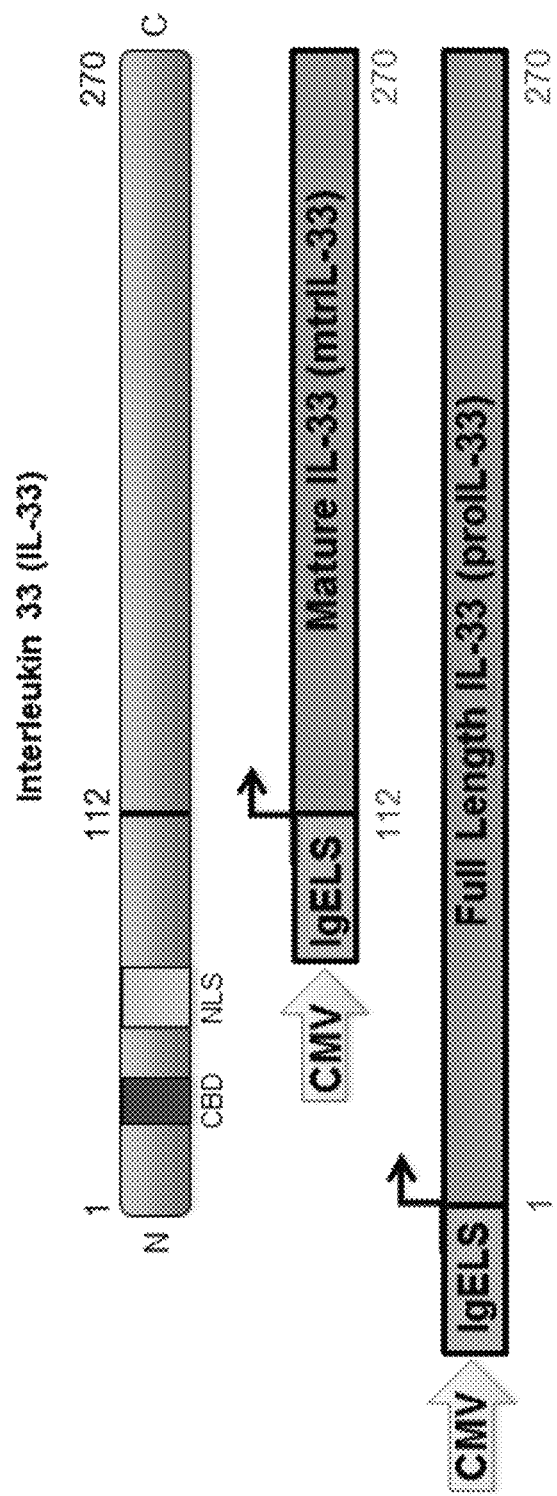
FIG. 10 shows a schematic representation of the human proIL-33 and human mtrIL-33 constructs.

The GenBank sequence NM_001164724.1 for mouse IL-33 was used to synthesize full-length (proIL-33) and mature IL-33 (mtrIL-33) (aa 109-266) plasmid DNA constructs (see FIG. 1A for a schematic illustration of the mouse proIL-33 and mouse mtrIL-33 constructs. Sequence for human IL-33 was also used to synthesize full-length (proIL-33) and mature (mtrIL-33) (aa 112-270) plasmid DNA constructs (see FIG. 10 for a schematic illustration of the human proIL-33 and human mtrIL-33 constructs). Each construct had a highly efficient immunoglobulin E (IgE) leader sequence inserted at the 5' end of the gene. Each construct was commercially synthesized and optimized. The optimized nucleic acid sequence SEQ ID NO:5 encoded mouse proIL-33 (SEQ ID NO:6). The optimized nucleic acid sequence SEQ ID NO:7 encoded mouse mtrIL-33 (SEQ ID NO:8). The optimized nucleic acid sequence SEQ ID NO:1 encoded human mtrIL-33 (SEQ ID NO:2). The optimized nucleic acid sequence SEQ ID NO:3 encoded human proIL-33 (SEQ ID NO:4). In each of these four constructs, the first eighteen amino acids (i.e., residues 1-18) were the IgE leader sequence. Plasmid expressing HPV 16 ConE6E7 and the GP33 construct were also prepared.

Transfection and Expression of Plasmids.

ProIL-33 and mtrIL-33 construct expression was confirmed by western blot and immunofluorescence. Human Rhabdomyosarcoma (RD) cell lines were cultured, transfected and harvested. Briefly, RD cells were cultured in 6-well plates and transfected with the constructs (pVAX as control) using LIPOFECTAMINE 2000 (Invitrogen) following the manufacturer's protocol. Forty-eight hours later, cells were lysed using modified RIPA cell lysis buffer and cell lysate was collected. Western blot analysis was performed with an anti-IL33 monoclonal antibody (R&D systems) and visualized with horseradish peroxidase (HRP)-conjugated anti-rat IgG (Cell Signaling) using an ECL western blot analysis system (GE Amersham). In addition, supernatants were also collected at 48 hours after transfection and cytokine secretion was examined by mouse/rat IL-33 Quantikine ELISA kit (R&D Systems) according to manufacturer's protocol.

Furthermore, an indirect immunofluorescent assay was also utilized to confirm expression of proIL-33 and mtrIL-33. Briefly, RD cells were plated on two-well chamber slides (BD Biosciences) and grown to 70% confluence overnight in a 37 degrees Celsius incubator with 5% $CO_2$. The cells were transfected with 1 μg of IL-33 constructs and the control plasmid pGX0001 (1 ug/well) using TURBOFECTION 8.0 Transfection Reagent (OriGene) according to the manufacturer's instructions. Forty-eight hours later, the cells were fixed on slides using ice cold methanol for 10 min. The cells were stained with anti-IL-33 mouse monoclonal antibody (R&D Systems, Minneapolis, Minn.) and subsequently incubated with Alexa 555-conjugated anti-rat secondary antibody (Cell Signaling). Images were analyzed by fluorescent microscopy (Leica DM4000B, Leica Mcirosystems Inc, USA) and quantification were conducted using SPOT Advanced software program (SPOT Diagnostic Instruments, Inc).

Animals.

Female 8-week-old C57BL/6 (B6) mice were purchased from Jackson Laboratory (Bar Harbor, Me., USA). The P14 mice bearing the $D^bGP33$-specific T-cell receptor were obtained from the University of Pennsylvania (laboratory of Dr. John Wherry). To generate the "P14 chimera" mice, $1.6 \times 10^5$ naïve T-cell receptor transgenic T cells were adoptively transferred into naïve B6 mice.

Immunization and Electroporation of Mice.

Mice were immunized three times at three-week intervals in the tibialis anterior muscle. In vivo Electroporation (EP), with the CELLECTRA adaptive constant current EP device (Inovio Pharmaceuticals, Blue Bell, Pa.), occurred at the same site immediately followed vaccinations. The mice (n=4) were immunized with either 5 μg pVAX1 or 5 μg ConE6E7 alone or with various amounts of proIL-33 and mtrIL-33 constructs, depending on the experiment (e.g., 5 μg and 7 μg). GP33 construct was administered at 5 μg.

ELISpot Assays.

First, spleens were harvested 8 days following the final immunization. After spleens were harvested and processed, both IFN-γ and IL-4 ELISpot assays were performed to determine antigen-specific cytokine secretion from immunized mice. A set of peptides (15 amino acid residues overlapping by 8 amino acids) representing the entire consensus E6/E7 fusion protein sequence of HPV 16 was synthesized from GenScript. This set of peptides was pooled into two pools, spanning the length of the E6 and E7 antigens. Concavalin A (Sigma-Aldrich, St. Louis, Mo.) at 5 μg/ml was used as positive control and complete culture medium was used as negative control. Spots were enumerated using an automated ELISPOT reader (Cellular Technology, Shaker Heights, Ohio).

Intracellular Cytokine Stain for Flow Cytometry.

Lymphocytes were isolated from the spleen and peripheral blood. Major histocompatibility complex class I peptide tetramer to LCMV-GP33 was used. Specifically, splenocytes were added to a 96-well plate ($1 \times 10^5$/well) and were stimulated with pooled HPV-16 E6/E7 pooled peptide for 5-6 hours at 37° C./5% $CO_2$ in the presence of Protein Transport Inhibitor Cocktail (Brefeldin A and Monensin) (ebioscience) according to the manufacturer's instructions. The Cell Stimulation Cocktail (plus protein transport inhibitors) (phorbol 12-myristate 13-acetate (PMA), ionomycin, brefeldin A and monensin) (ebioscience) was used as a positive control and R10 media as negative control. In cultures being used to measure degranulation, anti-CD107a (FITC; clone 1D4B; Biolegend) was added at this time to enhance staining.

All cells were then stained for surface and intracellular proteins. Briefly, the cells were washed in FACS buffer (PBS containing 0.1% sodium azide and 1% FCS) before surface staining with flourochrome-conjugated antibodies. Cells were washed with FACS buffer fixation and permeabilization using the BD CYTOFIX/CYTOPERM (BD, San Diego, Calif., USA) according to the manufacturer's protocol followed by intracellular staining.

The following antibodies were used for surface staining: LIVE/DEAD Fixable Violet Dead Cell stain kit (Invitrogen), CD19 (V50; clone 1D3; BD Biosciences), CD4 (V500; clone RM4-5; BD Biosciences), CD8 (PE-TexasRed; clone 53-6.7; Abcam), CD44 (A700; clone IM7; Biolegend); KLRG1 (FITC; clone 2F1; eBioscience); and PD-1 (PeCy7; clone RMP1-30; Biolegend). Major histocompatibility complex class I peptide tetramer to LCMV-GP33 was used. For intracellular staining, the following antibodies were used: IFN-γ (APC; clone XMG1.2; Biolegend), TNF-α (PE; clone MP6-XT22; ebioscience), and CD3 (PerCP/Cy5.5; clone 145-2C11; Biolegend).

All data were collected using a LSRII flow cytometer (BD Biosciences) and analyzed using FlowJo software (Tree Star, Ashland, Oreg.) and SPICE v5.2 (available from the National Institutes of Health (NIH), specifically, the National Institutes of Allergy and Infectious Disease (NIAID)). Boolean gating was performed using FlowJo software to examine the polyfunctionality of the T cells from vaccinated animals. Dead cells were removed by gating on a LIVE/DEAD fixable violet dead cell stain kit (invtirogen) versus forward scatter (FSC-A).

Ag-Specific Antibody Determination.

The measurement of IgG antibodies specific for viral genes E6 and E7 was performed by ELISA (enzyme linked immunosorbent assay) in both immunized and controlled mice. The plates were coated with 1 µg/ml of each protein (ProteinX Lab) and incubated overnight at 4 degrees Celsius. After washing, plates were blocked with 10% fetal bovine serum (FBS) in 1× phosphate-buffered saline (PBS) for 1 hour at room temperature. Plates were then washed again and serum was added at a 1:25 dilution in 1% FBS+PBS+0.05% Tween-20 and incubated at room temperature for 1 hour. After another wash, goat anti-mouse IgG HRP (Santa Cruz) at a 1:5000 dilution was added to each well and incubated for 1 hour at room temperature. Following a final wash, the reaction was developed with the substrate 3,3',5,5'-tetramethylbenzidine (Sigma-Aldrich) and stopped with 100 µL of 2N sulfuric acid/well. Plates were read at 450 nm on Glomax Multi-Detection System (Promega). All serum samples were tested in duplicate.

The amount of antigen specific IgE was also determined using a similar ELISA protocol using the secondary rat anti-mouse IgE HRP antibody (Southern Biotech). Total IgE was determined using GenWay's mouse IgE kit. The manufacturer's protocol was followed with serum dilutions at 1:50. All serum samples were tested in duplicate.

Tumor Cell Line.

The TC-1 cell line constitutively expresses E6 and E7 and is highly tumorigenic. TC-1 cells were cultured, prepared, and mixed with Matrigel (BD Bioscience) prior to subcutaneous (s.c.) tumor implantation.

In Vivo Tumor Treatment (Regression) Study.

Female B6 mice were separated into four groups of 10 mice each and 5×10$^4$ TC-1 cells were s.c. implanted into the flanks of each wild-type female B6 mice. On day 4, (after tumor implantation and when tumors reached 3 mm), each group of mice was immunized intramuscularly by electroporation (i.m./EP; described above) with pVAX, ConE6E7, ConE6E7 proIL-33, and ConE6E7 mtrIL-33, respectively, and boosted on day 11 and 18. Mice were monitored twice a week for tumor growth by measurement of the tumors. Animals were sacrificed when tumor diameter reached 20 mm.

Statistical Analysis.

Student's t-test was applied for comparison of the quantitative data of the cellular immune response and tumor diameters. In this study, p<0.05 were regarded as statistically significant.

Example 2

Construction and Expression of IL-33 Isoforms

To examine whether IL-33 may function as an adjuvant in DNA vaccination, proIL-33 and mtrIL-33 constructs were designed and generated as depicted in FIG. 1A and described above. Each construct was under the control of a cytomegalovirus (CMV) promoter and contained an IgE leader sequence.

To determine the expression of the proIL-33 and mtrIL-33 forms, human rhabdomyosarcoma (RD) cells were transfected separately with each construct. RD cells transfected with the expression vector pVAX served as a negative control. Cell lysates were harvested 48 hours (hrs) after transfection. Expression of proIL-33 and mtrIL-33 was detected in respective cell lysates by western immunoblotting using an anti-IL-33 monoclonal antibody (mAb). No IL-33 protein was detected in the lane corresponding to the negative pVAX control (FIG. 1B). In the lane corresponding to mrtIL-33, the expected band size was observed (about 20 kiloDaltons (kDA)). In the lane corresponding to proIL-33, a larger band (about 30 kDA) and a smaller band (about 20 kDA) were observed and corresponded to the expected sizes for proIL-33 and mtrIL-33, respectively. Accordingly, these data indicated that proIL-33 and mtrIL-33 were expressed from the constructs.

To examine secretion of the proIL-33 and mtrIL-33 forms, cell supernatants were obtained 48 hrs after transfection of RD cells. Detection of protein secretion into the extracellular environment was carried out by enzyme-linked immunosorbent assays (ELISAs). As shown in FIG. 1C, supernatants from mtrIL-33 and proIL-33 transfected RD cells contained mtrIL-33 and proIL-33 at concentrations of roughly 20,000 pg/ml and 600 pg/ml, respectively. Cell supernatants from RD cells transfected with the expression vector pVAX served as a negative control and no IL-33 was secreted from these same cells. Data shown in FIG. 1C are the means with standard error of the means (SEM) for two replicate assays.

Expression of both proIL-33 and mtrIL-33 was further confirmed using immunofluorescent staining. The primary antibody was an anti-IL-33 mouse mAb and the secondary antibody was an Alexa 555-conjugated anti-rat antibody. DAPI was used to stain nuclei. In RD cells transiently transfected with the proIL-33 construct, high nuclear expression with some cytoplasmic expression of proIL-33 was observed, indicating that proIL-33 is primarily localized in the nucleus (FIG. 1D, bottom panel). In RD cells transiently transfected with the mtrIL-33 construct, only high cytoplasmic expression of mtrIL-33 was observed, indicating that mtrIL-33 is localized to the cytoplasm (FIG. 1D, middle panel). RD cells transiently transfected with the expression vector pVAX served as a negative control and no IL-33 was detected in these same cells (FIG. 1D, top panel). These staining data reflected one structural difference between proIL-33 and mtrIL-33, namely the nuclear localization signal present in proIL-33 and not mtrIL-33.

Example 3

IL-33 Enhanced the Cellular Immune Response to a DNA Vaccine

As described above, IL-33 induces and supports a Th2 immune response. The Th2 immune response includes induction of the cytokine Interleukin-4 (IL-4). Accordingly, the above described proIL-33 and mtrIL-33 constructs were further examined to determine if IL-33 could increase induction of the Th2 immune response to an antigen, for example, a consensus-based fusion HPV 16 E6/E7 (ConE6E7) antigen. The Th1 immune response to ConE6E7 was also studied by examining IFN-γ secretion. In particular, a plasmid encoding ConE6E7 antigen (ConE6E7 construct) was administered to mice alone or in combination with the proIL-33 or mtrIL-33 constructs. Administration of the construct(s) was followed by electroporation.

Figure 2:
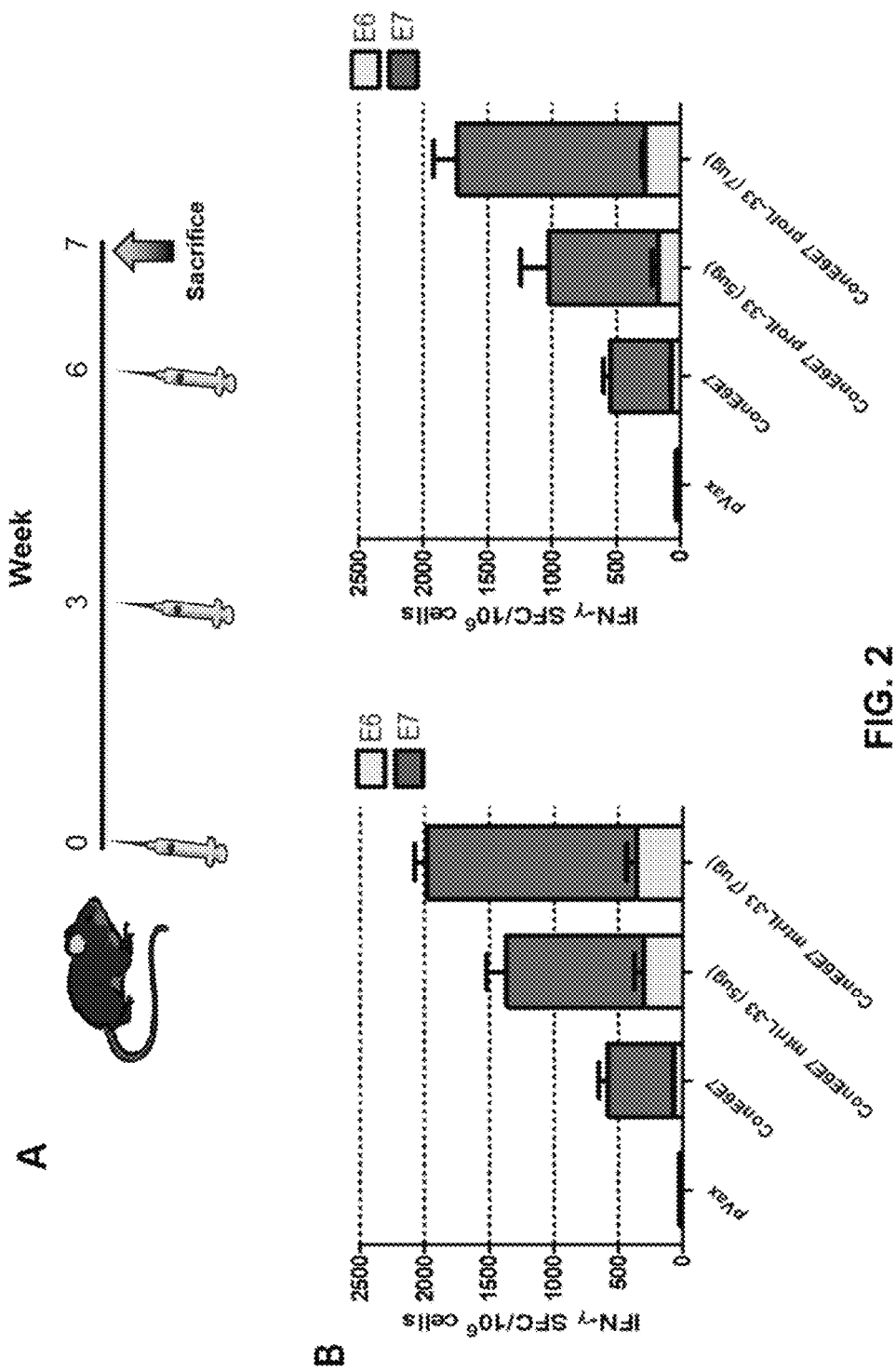
FIG. 2 shows in (A) a DNA vaccine immunization schedule; (B) IFN-γ ELISpot; and (C) IL-4 ELISpot.

FIG. 2A shows the DNA vaccine immunization schedule. C57BL/6 (B6) mice (n=4 for each group) were administered intramuscular (i.m.) a dosage of 5 μg of ConE6E7 construct alone or in combination with either mtrIL-33 or proIL-33 construct at various doses (i.e., 5 μg and 7 μg). The fourth group of mice was administered by i.m. a dosage of 5 μg of pVAX. Intramuscular administration of the construct(s) was followed by electroporation. Immunization occurred at weeks 0, 3, and 6. One week after final immunization (i.e., week 7), mice were sacrificed to collect spleens. Lymphocytes were isolated from the spleens and the immune responses of each group of mice was analyzed using a quantative ELISpot assay.

The ELISpot assay was used to determine the number of antigen-specific IFN-γ or IL-4 secreting cells in response to stimulation with the E6 and E7 peptide pool (described above in Example 1). As shown in FIG. 2B, IL-33 drove Th1-polarized immune responses. The induction of the Th1 immune response is shown by the frequency of HPV 16 E6- and E7-specific IFN-γ spot-forming units (SFU) per million splenocytes. Co-immunization with plasmid encoding either proIL-33 or mtrIL-33 induced higher numbers of E6- and E7-specific IFN-γ secreting T cells at all doses (i.e., 5 μg and 7 μg) when compared with mice vaccinated with the ConE6E7 construct alone (about 500 SFU per million splenocytes). The dose of 7 μg of mtrIL-33 or proIL-33 resulted in a total 4- or 3.5-fold increase in IFN-γ ELISpot magnitude, respectively.

As shown in FIG. 2C, neither proIL-33 nor mtrIL-33 drove robust secretion of IL-4. The induction of the Th2 immune response is shown by the frequency of HPV 16 E6- and E7-specific IL-4 spot-forming units (SFU) per million splenocytes.

As noted above, IL-33 was thought to induce and support a Th2 immune response. Instead, both proIL-33 and mtrIL-33 as adjuvants were biased towards the Th1, and not the Th2, cytokine associated immune responses. Accordingly, these data are unexpected and surprising in that IL-33 (both the proIL-33 and mtrIL-33 forms) increased induction of the Th1 (cellular immune response as evidenced by IFN-γ), but did not increase induction of the Th2 (humoral immune response as evidenced by IL-4) for the DNA vaccine. These data showed that both proIL-33 and mtrIL-33 are effective adjuvants that induce a cellular immune response.

Example 4

IL-33 Enhanced HPV Antigen-Specific CD4$^+$ T Cell Immunity

As demonstrated above, both proIL-33 and mtrIL-33 amplified the antigen (Ag)-specific IFN-γ immune response induced by vaccination. This immune response was further examined by characterizing the phenotype and cytokine profile of the effector T cells generated by the immune response. In particular, CD4$^+$ and CD8$^+$ (discussed below in Example 5) T cell immunity was examined via IFN-γ and TNF-α secretion because multifunctional CD4$^+$ and CD8$^+$ T cell immunity facilitates elimination of HPV 16-infected cells.

B6 mice were immunized by intramuscular (i.m.) injection with a dosage of 5 μg of ConE6E7 construct with or without 7 μg of mtrIL-33 or proIL-33 construct, followed by electroporation. A fourth group of mice was administered by i.m. a dosage of 5 μg of pVAX. Intramuscular administration of the construct(s) was followed by electroporation. Immunization occurred at weeks 0, 3, and 6. One week after final immunization (i.e., week 7), mice were sacrificed to collect spleens. Accordingly, immunization occurred at 3 week intervals, and splenocytes were collected one week after the final immunization. The splenocytes were stimulated with pooled E6 and E7 peptide to determine the ability of vaccine-induced Ag-specific T cell populations to secrete IFN-γ and TNF-α in response to stimulation. After stimulation, splenocytes were analyzed using flow cytometry following intracellular staining with antibodies against IFN-γ and TNF-α. The gating strategy for analyzing the frequency of CD4$^+$ T cells positive for IFN-γ and TNF-α cytokines is shown in FIG. 3A.

Figure 3:
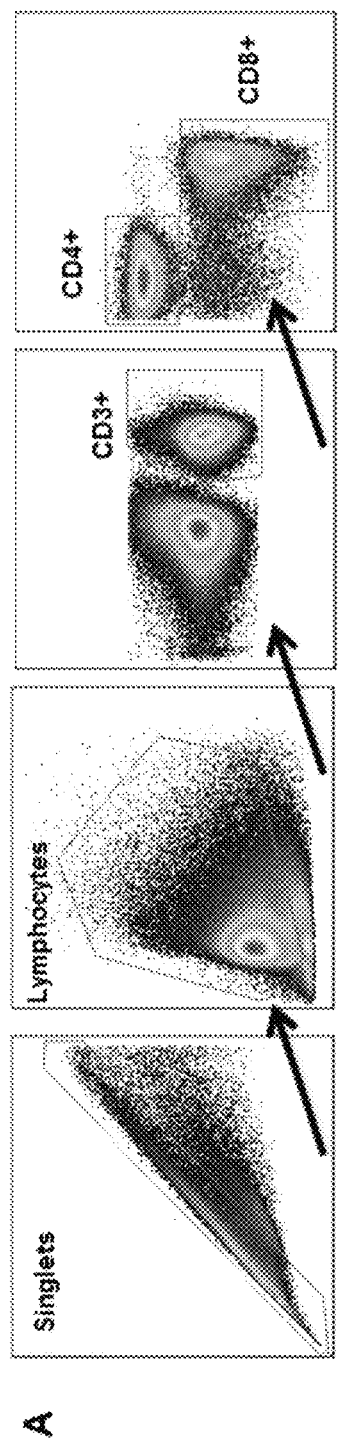
FIG. 3 shows in (A) the gating strategy for the flow cytometry analysis; (B) E6/E7-specific CD4$^+$ T cells releasing IFN-γ; (C) E6/E7-specific CD4$^+$ T cells releasing TNF-α; (D) E6/E7-specific CD4$^+$ T cells releasing IFN-γ and TNF-α; and (E) subpopulations of single- and double-positive CD4$^+$ T cells.
Figure 3:
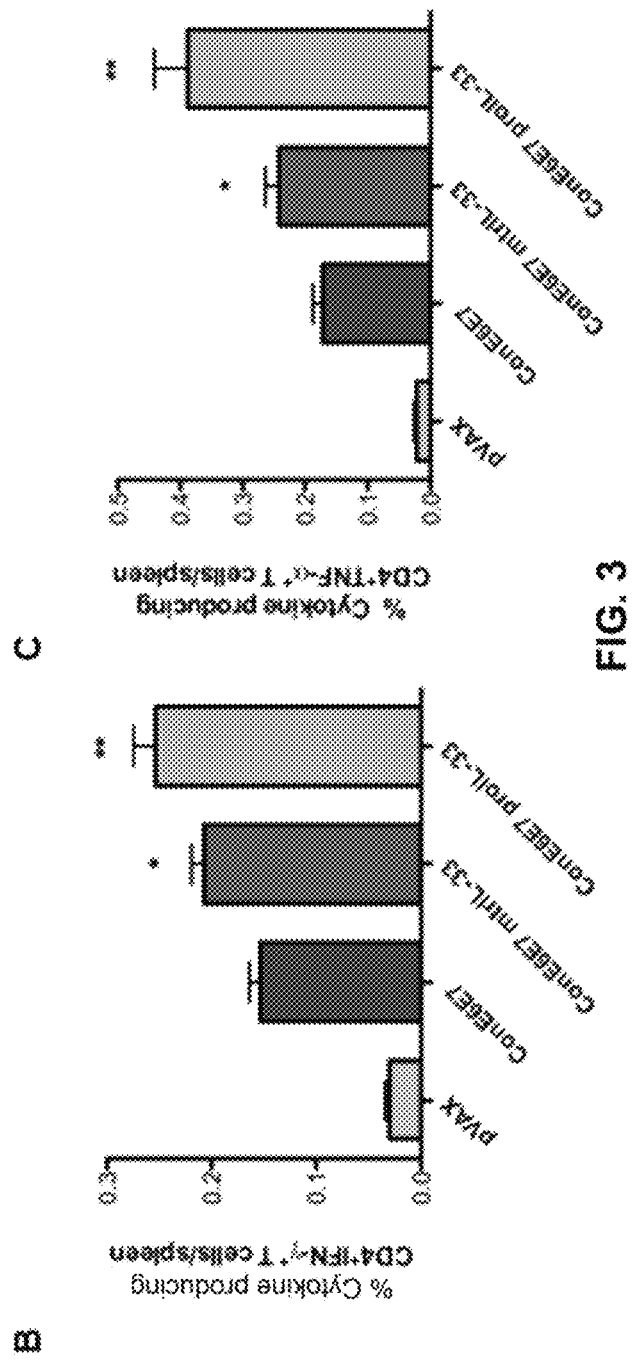

FIGS. 3B-3E show the data from the analysis of CD4$^+$ T cells positive for IFN-γ, TNF-α, or both IFN-γ and TNF-α. Data represent mean±SEM of four mice per group. **$P<0.01$, *$P<0.05$ compared with ConE6E7 (Student's t-test). Compared with the negative control pVAX and ConE6E7 vaccination alone, the ConE6E7 co-administered with mtrIL-33 or proIL-33 elicited a higher frequency of HPV-specific CD4$^+$ T cells producing either total IFN-γ (mtrIL-33: 0.21%; proIL-33: 0.25%), total TNF-α (mtrIL-33: 0.25%; proIL-33: 0.39%) and dual IFN-γ/TNF-α (mtrIL-33: 0.12%; proIL-33: 0.15%) (FIGS. 3B-3D). A similar trend was observed with the frequency of Ag-specific CD4$^+$ T cells producing IFN-γ alone and TNF-γ alone (FIG. 3E). In FIG. 3E, column graphs show plurifunctional subpopulations of single- and double-positive CD4$^+$ T cells releasing cytokines IFN-γ and/or TNF-α. Single-positive CD4$^+$ T cells are those cells releasing either IFN-γ or TNF-α while double-positive CD4$^+$ T cells are those cells releasing both IFN-γ and TNF-α. The pie charts in FIG. 3E show the relative proportion of each cytokine subpopulation to Ag-specific stimulation.

The above data demonstrated that the frequencies of CD4$^+$ T cells producing IFN-γ, TNF-α and dual IFN-γ/TNF-α was significantly increased when either proIL-33 or mtrIL-33 was an adjuvant in the vaccine. The high frequencies of effector T cells secreting anti-viral cytokines such as IFN-γ and TNF-α are indicative of the adjuvant effects of both proIL-33 and mtrIL-33 to enhance vaccine potency. These data further indicated the ability of both proIL-33 and mtrIL-33 to act as effective adjuvants, namely by inducing CD4$^+$ T cell immunity and secretion of the IFN-γ and TNF-α cytokines.

Example 5

IL-33 Enhanced HPV Antigen-Specific CD8+ T Cell Immunity

Similar to CD4+ T cell immunity, multifunctional CD8+ T cell immunity also facilitates elimination of HPV 16-infected cells. Accordingly, IFN-γ and TNF-α secretion in response to vaccination was also examined for CD8+ T cells.

Specifically, B6 mice were immunized by intramuscular (i.m.) injection with a dosage of 5 µg of ConE6E7 construct with or without 7 µg of mtrIL-33 or proIL-33 construct, followed by electroporation. A fourth group of mice was administered by i.m. a dosage of 5 µg of pVAX. Intramuscular administration of the construct(s) was followed by electroporation. Immunization occurred at weeks 0, 3, and 6. One week after final immunization (i.e., week 7), mice were sacrificed to collect spleens. Accordingly, immunization occurred at 3 week intervals, and splenocytes were collected one week after the final immunization. The splenocytes were stimulated with pooled E6 and E7 peptide to determine the ability of vaccine-induced Ag-specific T cell populations to secrete IFN-γ and TNF-α in response to stimulation. After stimulation, splenocytes were analyzed using flow cytometry following intracellular staining with antibodies against IFN-γ and TNF-α. The gating strategy for analyzing the frequency of CD8+ T cells positive for IFN-γ and TNF-α cytokines is shown in FIG. 3A.

Figure 4:
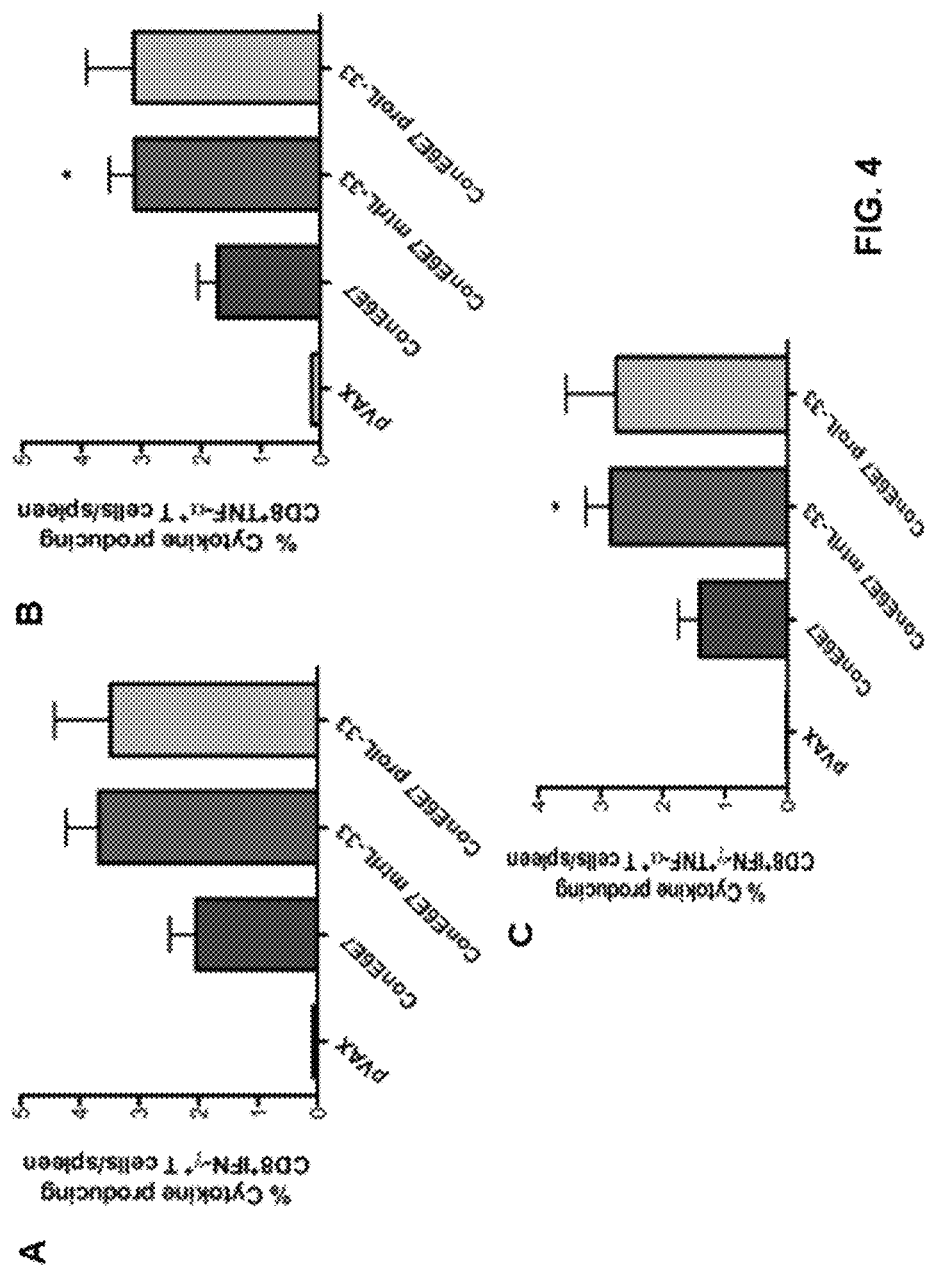
FIG. 4 shows in (A) E6/E7-specific CD8$^+$ T cells releasing IFN-γ; (B) E6/E7-specific CD8$^+$ T cells releasing TNF-α; (C) E6/E7-specific CD8$^+$ T cells releasing IFN-γ and TNF-α; (D) subpopulations of single- and double-positive CD8$^+$ T cells; (E) E6/E7-specific CTLs expressing degranulation marker CD107a; and (F) subpopulations of single-, double-, and triple-positive CD8$^+$ T cells.

FIGS. 4A-D show the data from the analysis of CD8+ T cells positive for IFN-γ, TNF-α, or both IFN-γ and TNF-α. Data represent mean±SEM of four mice per group. *P<0.05 compared with ConE6E7 construct (Student's t-test). Compared with the negative control pVAX and ConE6E7 vaccination alone, the ConE6E7 co-administered with mtrIL-33 or proIL-33 elicited substantially higher frequencies of HPV-specific CD8+ T cells producing total IFN-γ (mtrIL-33: 3.68%; proIL-33: 3.50%), total TNF-α (mtrIL-33: 3.11%; proIL-33: 3.13%) and dual IFN-γ/TNF-α (mtrIL-33: 2.83%; proIL-33: 2.75%) (FIGS. 4A-4C).

The same trend was observed with the frequency of Ag-specific CD8+ T cells secreting IFN-γ alone and TNF-α alone (FIG. 4D). In FIG. 4D, the column graph shows plurifunctional subpopulations of single- and double-positive CD8+ T cells releasing cytokines IFN-γ and/or TNF-α. Single-positive CD8+ T cells are those cells releasing either IFN-γ or TNF-α while double-positive CD8+ T cells are those cells releasing both IFN-γ and TNF-α. The pie charts in FIG. 4D show the relative proportion of each cytokine subpopulation to Ag-specific stimulation. The dot plots in FIG. 4D are representative of four mice and depict double-positive CD8+ T cells after stimulation with pooled E6/E7 peptide. The proportional order of effector CD8+ T cell subpopulations in response to E6E7 stimulation was greatest with cells double positive for both cytokines, IFN-γ+/TNF-α+, followed by IFN-γ alone, which in turn was greater than cells secreting TNFα+ alone (FIG. 4D).

The above data demonstrated that the frequencies of CD8+ T cells producing IFN-γ, TNF-α and dual IFN-γ/TNF-α was significantly increased when either proIL-33 or mtrIL-33 was an adjuvant in the vaccine. The co-administration with proIL-33 and mtrIL-33 produced similar amounts of Ag-specific CD4+ and CD8+ T cells producing IFN-γ, TNF-α and dual IFN-γ/TNF-α, in which cytokine production was mediated mainly by CD8+ T cells. The high frequencies of effector T cells secreting anti-viral cytokines such as IFN-γ and TNF-α are indicative of the adjuvant effects of IL-33 to enhance vaccine potency. These data further indicated the ability of both proIL-33 and mtrIL-33 to act as effective adjuvants, namely by inducing CD8+ T cell immunity and secretion of the IFN-γ and TNF-α cytokines.

Example 6

IL-33 Induced Cytotoxic CD8+ T Lymphocytes (CTLs)

Cytotoxic CD8+ T lymphocytes (CTLs) also provide protective immunity by undergoing degranulation. CD107a is a marker of degranulation. Whether CD8+ T cells are induced to undergo degranulation when IL-33 was an adjuvant in the vaccine was examined to better understand the cytotoxic potential of the vaccine.

B6 mice were immunized by intramuscular (i.m.) injection with a dosage of 5 µg of ConE6E7 construct with or without 7 µg of mtrIL-33 or proIL-33 construct, followed by electroporation. A fourth group of mice was administered by i.m. a dosage of 5 µg of pVAX. Intramuscular administration of the construct(s) was followed by electroporation. Immunization occurred at weeks 0, 3, and 6. One week after final immunization (i.e., week 7), mice were sacrificed to collect spleens. Accordingly, immunization occurred at 3 week intervals, and splenocytes were collected one week after the final immunization. The splenocytes were stimulated with pooled E6 and E7 peptide to determine the ability of vaccine-induced Ag-specific T cell populations to secrete IFN-γ and TNF-α in response to stimulation. The ability of vaccine-induced Ag-specific T cell populations to express CD107a in response to stimulation was also examined. After stimulation, splenocytes were analyzed using flow cytometry following intracellular staining with antibodies against IFN-γ, TNF-α, and CD107a. The gating strategy for analyzing the frequency of CD8+ T cells positive for IFN-γ, TNF-α, and CD107a is shown in FIG. 3A.

FIGS. 4E and 4F show the antigen-specific cytolytic degranulation of T cells as measured by the degranulation marker CD107a and the cytokine profile of the cytolytic phenotype, respectively. Data represent mean±SEM of four mice per group. *P<0.05 compared with ConE6E7 construct (Student's t-test).

CD8+ T cells isolated from mice vaccinated with proIL-33 or mtrIL-33 as an adjuvant showed a higher frequency of the degranulation marker, CD107a (mtrIL-33: 4.4%; proIL-33: 4.9%), compared to mice that received the ConE6E7 construct alone (FIG. 4E). A substantial proportion of HPV-specific effector cells were plurifunctional, expressing the degranulation marker CD107a and simultaneously expressing IFN-γ and TNF-α in various combinations (FIG. 4F). Vaccines including proIL-33 or mtrIL-33 as an adjuvant elicited substantially higher frequencies of effector CD8+ T cells co-expressing CD107a/IFN-γ/TNF-α (mtrIL-33: 2.5%; proIL-33: 2.5%). These results indicated the adjuvant potential of both proIL-33 and mtrIL-33 to induce functional effector cytotoxic CTLs, which have a phenotype that indicated the cells ability to clear HPV16 infected cells. These data further indicated the ability of both proIL-33 and mtrIL-33 to act as effective adjuvants, namely by inducing CD8+ T cell immunity and secretion of the IFN-γ and TNF-α cytokines.

Together, the data from Examples 4-6 demonstrated that co-immunization of HPV ConE6E7 construct with either mtrIL-33 or proIL-33 construct as the adjuvant resulted in stronger HPV-specific cellular immunity. Accordingly, vaccines including proIL-33 and mtrIL-33 as adjuvants showed therapeutic potential.

Example 7

ProIL-33 Induced Expansion of CD8+ T Cells

The CD8+ T cell response induced by inclusion of proIL-33 as an adjuvant in the vaccine was further examined to determine if proIL-33 could induce expansion of CD8+ T cells. Populations of T cell subsets can be tracked using the P14 ($D^b$GP33-specific T cell receptor (TCR)) mouse model, thereby allowing for the monitoring of the expansion of CD8+ T cells in response to vaccination. As described in more detail below, the expansion of GP33/Ly5.1+-specific CD8+ T cells was monitored in response to immunization with vaccine that did or did not include proIL-33 as an adjuvant.

Figure 5:
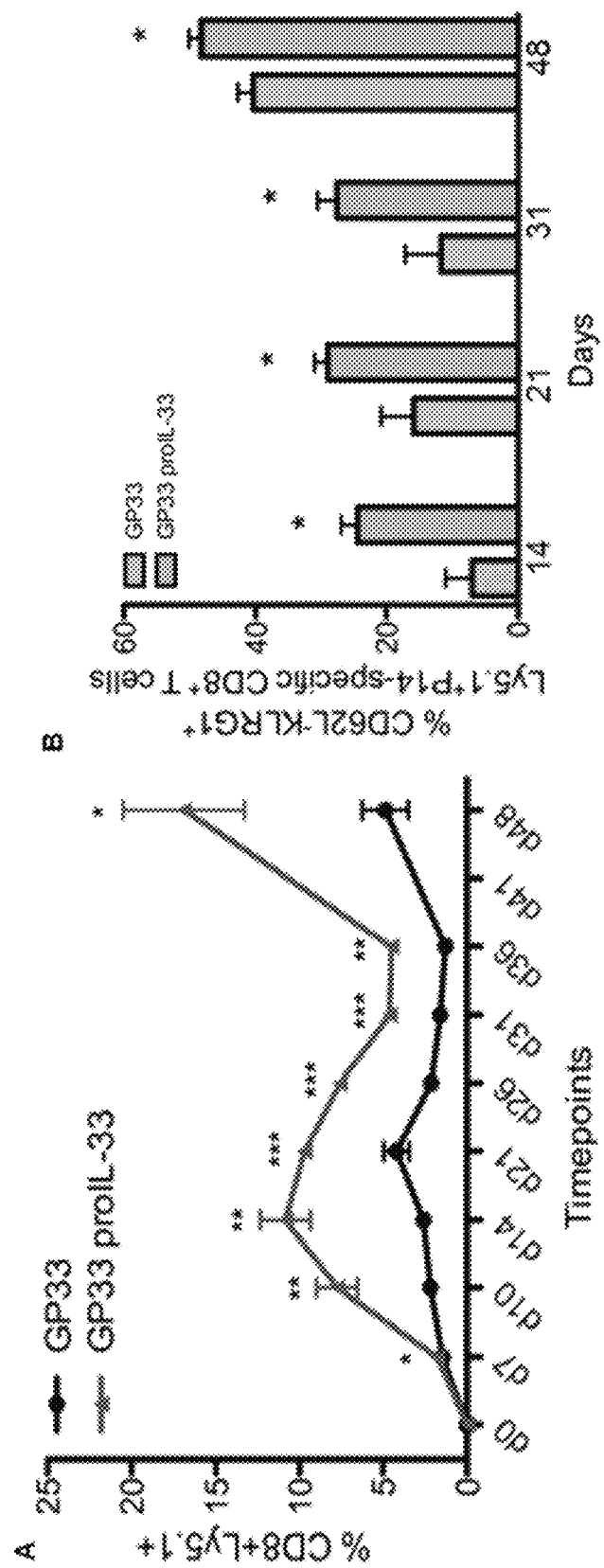
FIG. 5 shows in (A) kinetics of Ly5.1 expression and (B) distribution of effector-memory CD8$^+$ T cells.
Figure 6:
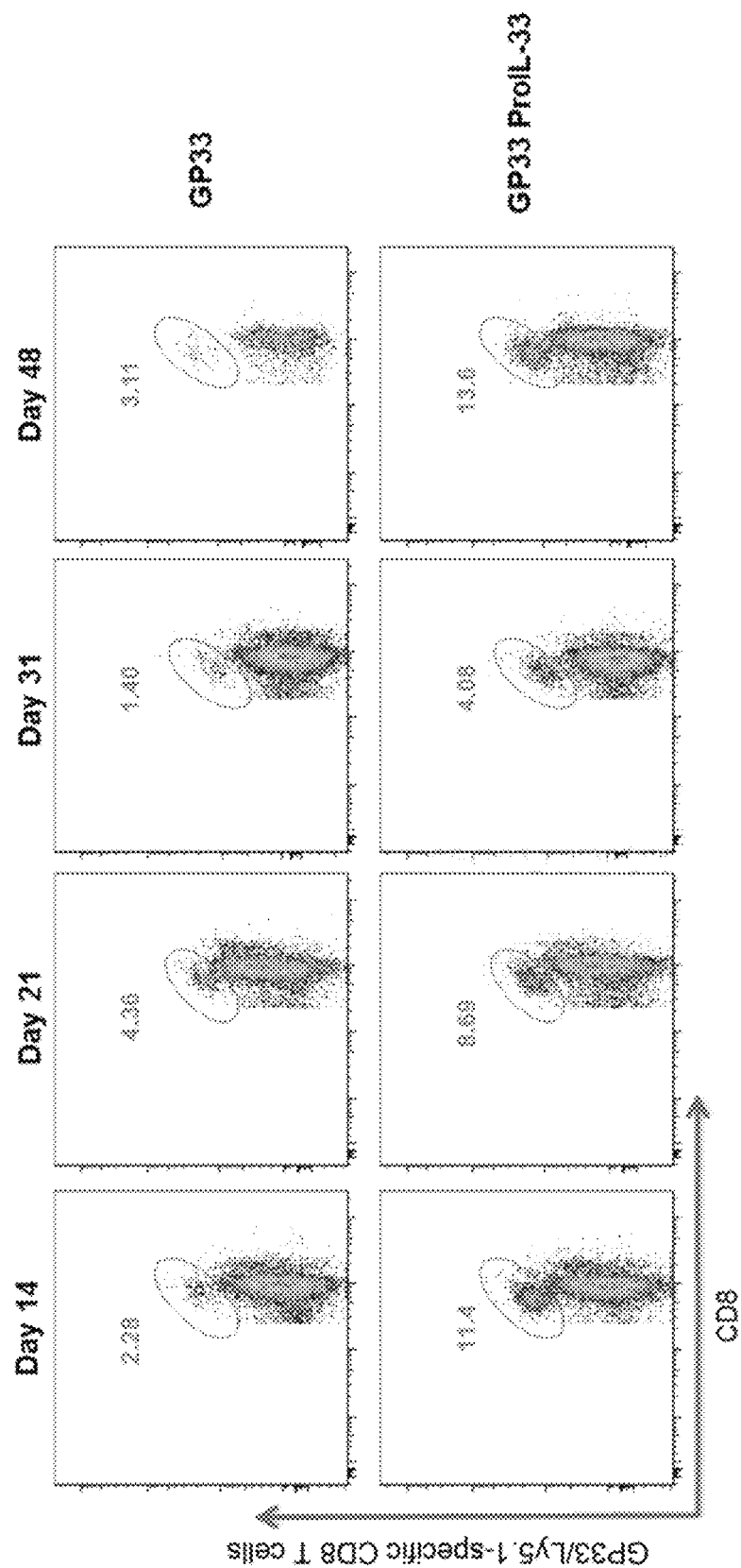
FIG. 6 shows representative flurorescent intensity plots of GP33/Ly5.1-specific CD8$^+$ T cell responses.

Specifically, about 150,000 Ly5.1+ naïve P14 TCR transgenic CD8+ T cells were transferred into naïve wild-type recipients to make "P14 chimeric mice." The P14 chimeric mice were subsequently vaccinated twice with GP33 alone or GP33 in combination with proIL-33 construct on day 0 (prime) and day 41 (boost). The frequency of the Ag-specific CD8+ T cell response was monitored in the blood during the course of the prime and boost DNA vaccination with or without proIL-33 adjuvant (FIGS. 5A and 6). In particular, FIG. 5A shows the kinetics of Ly5.1 expression on P14-specific CD8+ T cells in peripheral blood mononuclear cells (PBMC). For FIG. 5A, error bars represented mean±SEM of four mice per group while *$P<0.001$, $P<0.01$, and *$P<0.05$ compared with GP33 alone (Student's t-test). FIG. 6 shows representative fluorescent intensity plots of GP33/Ly5.1-specific CD8+ T cells in the blood of vaccinated mice at days 14, 21, and 31 after first vaccination and day 48 (day 7 after the second vaccination). The numbers in FIG. 6 indicate the percentage of Ag-specific CD8+ T cells within the total CD8+ T cell populations.

The data in FIGS. 5A and 6 indicated that mice administered GP33 and proIL-33 constructs had a significantly increased frequency of P14 CD8+Ly5.1+ T cells in the blood as compared to the mice administered only GP33 construct. This significantly increased frequency (about 5-fold) of Ly5.1+CD8+ T cells in the mice vaccinated with GP33 and proIL-33 constructs peaked at about 14 dpv (days post vaccination) as compared to the GP33 immunized group. Specifically, the increase in frequency for the GP33 and proIL-33 vaccinated group peaked 7 days before the GP33 only vaccinated group reached its peak at about 21 dpv. These data indicated that inclusion of proIL-33 as an adjuvant in the vaccine significantly expanded the magnitude of Ag-specific CD8+ T cell response.

Furthermore, seven days after homologous boosting (48 days after initial vaccination), proIL-33 immunoadjuvant significantly increased the frequency of Ag-specific CD8+ T cells compared to mice that received GP33-only vaccine (FIG. 5A). This increase in frequency of Ag-specific CD8+ T cells after boost indicated recall of the established memory CD8+ T cell pool. These data further indicated that inclusion of proIL-33 as an adjuvant in the vaccine not only significantly expanded the magnitude of Ag-specific CD8+ T cell response after prime vaccination, but also significantly increased Ag-specific CD8+ T cells response after boost vaccination. Accordingly, these data further demonstrated that the ability of proIL-33 to function as an adjuvant in a vaccine by significantly enhancing the Ag-specific CD8+ T cell response by expanding both effector and effector-memory Ag-specific CD8+ T cell responses.

Example 8

ProIL-33 Elicited CD62L−KLRG1+ Effector-Memory T Cells

Effector CD8+ T cells (e.g., CD62L−KLRG1+ effector-memory T cells) provide protective immunity and pathogen control, and the above data indicated that as an adjuvant, proIL-33 increased the frequency of Ag-specific CD8+ T cells both in response to prime and boost vaccinations. To further determine the efficacy of vaccines including proIL-33 as an adjuvant, the P14 mouse model was examined with regards to the CD62L−KLRG1+ effector-memory T cell response.

Specifically, populations of T cell subsets can be tracked using the P14 ($D^b$GP33-specific T cell receptor (TCR)) mouse model. About 150,000 Ly5.1+ naïve P14 TCR transgenic CD8+ T cells were transferred into naïve wild-type recipients to make "P14 chimeric mice." The P14 chimeric mice were subsequently vaccinated twice with GP33 alone or GP33 in combination with proIL-33 construct on day 0 (prime) and day 41 (boost).

FIG. 5B shows the distribution of effector memory CD8+ T cells from immunized mice at day 14, 21, 31 after the first vaccination and day 48 (day 7 after the second vaccination). Error bars represented mean±SEM of four mice per group while *$P<0.05$ compared with GP33 alone (Student's t-test).

In particular, the phenotype of the effector CD8+ T cells within the vaccine-induced P14-specific CD8+ T cell population was examined starting at 14 dpv. The following cell surface expression markers were examined: Ly5.1, CD62L and KLRG1 (FIG. 5B). As shown in FIG. 5B, the percentages of CD62L−KLRG1+ effector memory cells were significantly higher in the proIL-33 adjuvant group compared to the GP33-only vaccinated group. Although it was observed that the frequency of Ag-specific CD8+ T cells began a gradual contraction 14 dpv (FIG. 5A), the effector population in both vaccinated groups remained the same for 3 weeks (FIG. 5B). Together, these data indicated that high expression of KLRG1 by CD8+ T cells was associated with repetitive antigen stimulation. These data also indicated the ability of proIL-33 to enhance ongoing Ag persistent exposure.

Additionally, secondary memory cells showed a greatly expanded population of KLRG1+ T cells in both groups (i.e., GP33 alone and GP33 and proIL-33) after homologous DNA boosting, which occurred 48 days after initial immunization. The effector-memory responses remained significantly higher in the proIL-33-adjuvanted group compared to GP33-alone group (FIG. 5B). Together, the data of FIGS. 5A, 5B, and 6 as described here in Examples 7 and 8 indicated that proIL-33 increased the formation of Ag-specific CD8+ T cells and enhanced clonal expansion of the effector memory pool. These data further supported that proIL-33 is an effective adjuvant.

Example 9

ProIL-33 Induced IgG Humoral Response

As described in Example 3, proIL-33 and mtrIL-33 did not induce secretion of IL-4, which is part of the Th2 or humoral immune response. Accordingly, the humoral response to vaccines including proIL-33 or mtrIL-33 was further examined.

Respective groups of mice (n=4) were immunized with ConE6E7 construct alone, ConE6E7 construct with mtrIL-33 construct, and ConE6E7 construct with proIL-33 construct. As a negative control, one group of mice (n=4) was vaccinated with pVAX. Specifically, vaccination included intramuscular injection of the construct(s) followed by electroporation. Immunization occurred at weeks 0, 3, and 6. Blood was collected from each group of mice one week after the last immunization. ELISAs were then performed to measure the levels of IgG and IgE antibodies specific for HPV E6 and E7.

Figure 7:
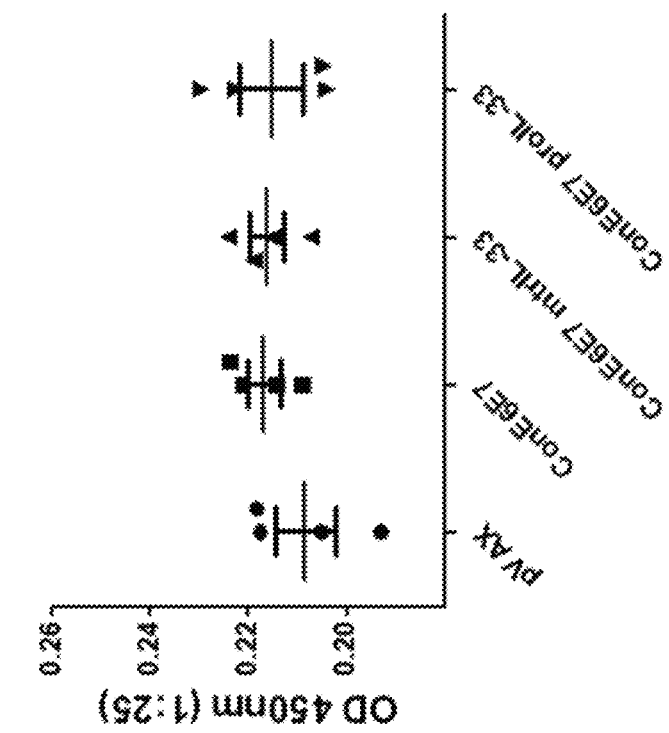
FIG. 7 shows in (A) specific total IgG antibodies against HPV16 E7; (B) specific total IgE antibodies against HPV16 E7; and (C) total IgE antibodies detected in serum.
Figure 7:
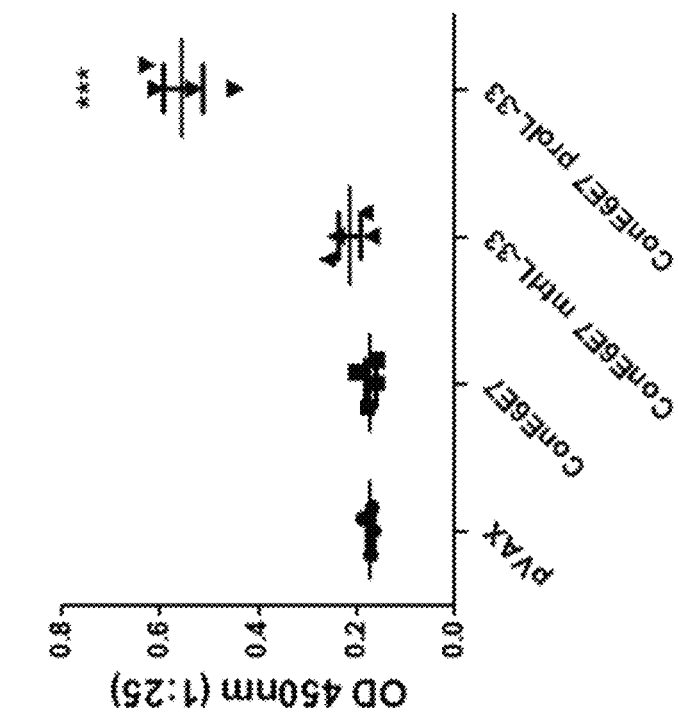

As shown in FIG. 7A, only co-immunization with proIL-33 significantly induced E7-specific total IgG compared to other immunized groups. ***P<0.001 compared with ConE6E7 construct alone (Student's t-test). No E6-specific antibodies were induced or detected (data not shown).

In addition, IL-33 has been implicated in allergic responses, which involve IgE antibodies. Accordingly, E7-specific IgE and total IgE responses in sera were measured by ELISA. As shown in FIGS. 7B and 7C, mtrIL-33 and proIL-33 did not enhance levels of IgE as compared to control vaccinated groups. IgE class-switch is driven by IL-4, and thus, this lack of enhancement was consistent with the low induction of IL-4 shown in FIG. 2C and described in Example 3. Additionally, careful evaluation at the site of DNA vaccination showed no detectable allergic skin reaction. These results supported that IL-33 adjuvant effects in a DNA vaccination setting did not induce Th2-associated responses.

In summary, the combination of antigen and proIL-33 increased Ag-specific IgG humoral responses, indicating proIL-33's role as an effective adjuvant to enhance both Ag-specific cell-mediated and humoral immune responses.

Example 10

IL-33 Induced Anti-Tumor Immunity and Regression of Established Tumors

Given the above data that both proIL-33 and mtrIL-33 were effective adjuvants that elicited significant HPV Ag-specific Th1- and CD8-biased T cell immune responses, an in vivo tumor therapy study was used to determine the therapeutic efficacy of IL-33 adjuvants. In particular, the in vivo tumor therapy study examined the ability of vaccines including either proIL-33 or mtrIL-33 as an adjuvant to clear established HPV-associated tumors or lesions and to protect against the formation of new HPV-associated tumors or lesions.

To examine clearance of established tumors or lesions, HPV16 E6/E7-expressing TC-1 tumors ($5 \times 10^4$) cells were implanted in naïve B6 recipient mice. Four days after TC-1 cell implantation, tumors were measured (tumors had reached an average size of 3 mm) and groups of mice (n=10) were immunized with pVAX (5 µg), ConE6E7 (5 µg) alone, or ConE6E7 (5 µg) co-administered with 7 µg of mtrIL-33 or proIL-33, followed with two boosts at one week intervals as outlined in FIG. 8A. pVAX immunized mice served as a negative control. Tumors were then measured twice a week in two dimensions with electronic calipers and data are presented with the average of these values over time for each individual mouse. Mice were sacrificed when tumor diameter reached approximately 2.0 cm.

Figure 8:
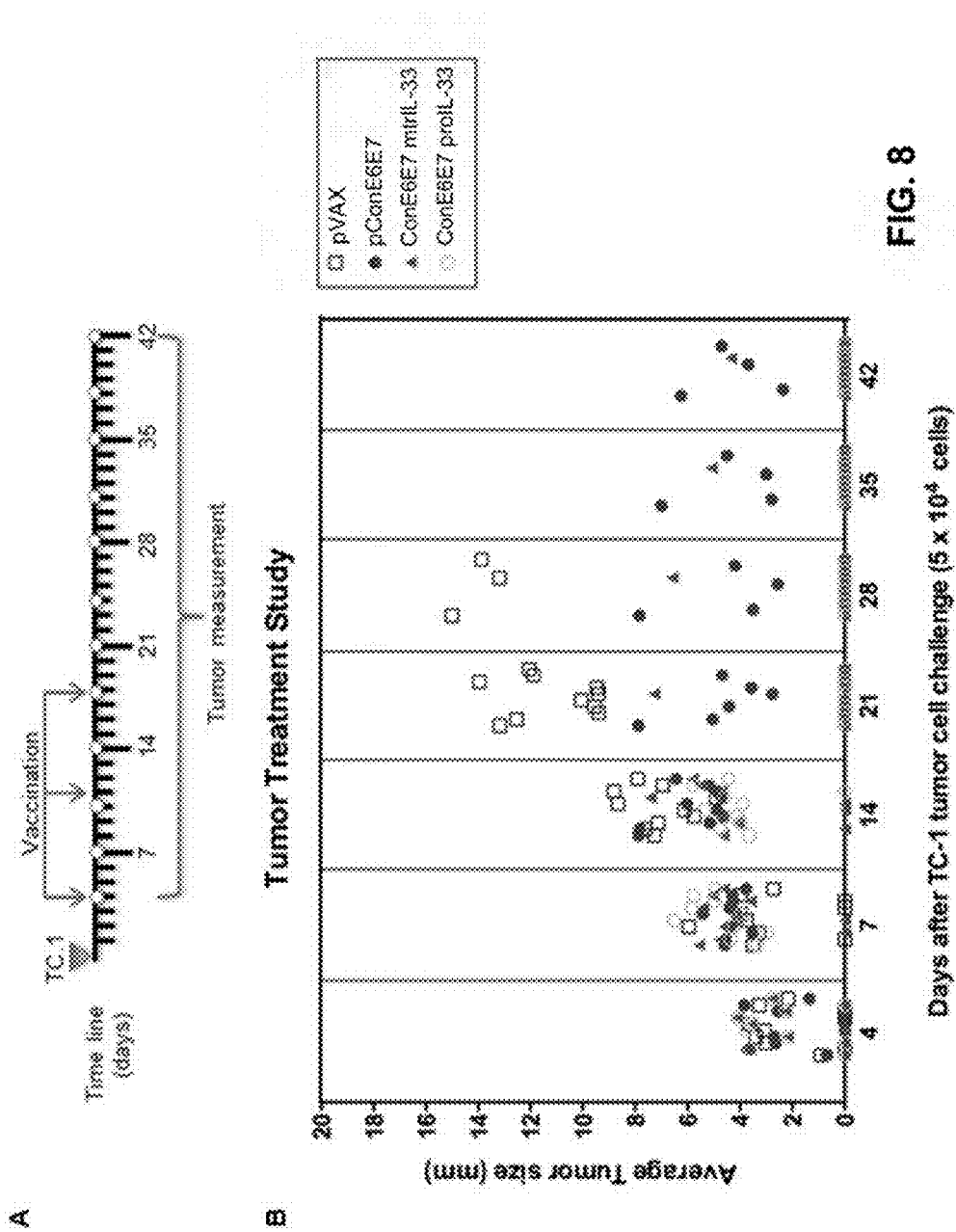
FIG. 8 shows in (A) a schematic illustration of the timeline of the therapeutic regimen; and (B) average tumor size over time after tumor cell challenge.

FIG. 8B shows the average tumor size in millimeters (mm) over time. Tumor measurements for each time point are shown only for surviving mice. Pairwise comparisons were done for the groups of mice at days 7, 14, 21, 28, and 35 after initial tumor implantation and the p values are shown below in Table 1. 9 out of 10 mice in the mtrIL-33-adjuvanted groups were tumor free 42 days after initial tumor implantation, while ConE6E7-proIL-33 vaccinated mice (i.e., 10 out of 10 mice) induced complete regression of established TC-1 tumors (FIG. 8B).

TABLE 1

P Values for FIG. 8B

| Comparison | p Value |
|---|---|
| Day 7: pVax vs. pConE6E7 | p ≤ 0.05 |
| Day 7: pVax vs. ConE6E7 mtrIL-33 | p ≤ 0.01 |
| Day 7: pVax vs. ConE6E7 proIL-33 | p ≤ 0.001 |
| Day 7: pConE6E7 vs. ConE6E7 mtrIL-33 | p ≤ 0.05 |
| Day 7: pConE6E7 vs. ConE6E7 proIL-33 | p ≤ 0.05 |
| Day 14: pVax vs. pConE6E7 | p ≤ 0.001 |
| Day 14: pVax vs. ConE6E7 mtrIL-33 | p ≤ 0.001 |
| Day 14: pVax vs. ConE6E7 proIL-33 | p ≤ 0.001 |
| Day 14: pConE6E7 vs. ConE6E7 mtrIL-33 | p = NS |
| Day 14: pConE6E7 vs. ConE6E7 proIL-33 | p ≤ 0.01 |
| Day 21: pVax vs. pConE6E7 | p ≤ 0.001 |
| Day 21: pVax vs. ConE6E7 mtrIL-33 | p ≤ 0.001 |
| Day 21: pVax vs. ConE6E7 proIL-33 | p ≤ 0.001 |
| Day 21: pConE6E7 vs. ConE6E7 mtrIL-33 | p = NS |
| Day 21: pConE6E7 vs. ConE6E7 proIL-33 | p ≤ 0.05 |
| Day 28: pConE6E7 vs. ConE6E7 mtrIL-33 | p = NS |
| Day 28: pConE6E7 vs. ConE6E7 proIL-33 | p ≤ 0.05 |
| Day 35: pConE6E7 vs. ConE6E7 mtrIL-33 | p = NS |
| Day 35: pConE6E7 vs. ConE6E7 proIL-33 | p ≤ 0.05 |

NS is not significant.

Meanwhile, only six mice in the pConE6E7-vaccinated group were tumor free after 42 days and in the control group all mice died by day 21. Significantly, ConE6E7 vaccinated animals co-immunized with mtrIL-33 or proIL-33 began to show regression of established tumors, within 10 days after first immunization, with the majority tumor free 17 days post first immunization (FIG. 8B). In contrast, mice that were treated with ConE6E7 alone displayed slower tumor regression, and only 4 out of 10 mice were tumor free by 17 days after initial vaccination. The IL-33 groups remained tumor free until day 42, with the exception of one mouse in the mtrIL-33-adjuvant group. In addition, the proIL-33 adjuvant group showed complete tumor regression by 17 days post vaccination, which correlated with the peak of CD8$^+$ T cell expansion (14 days post vaccination) mediated by proIL-33 described above and in FIGS. 5A and 6. These data indicated that CD8$^+$ T cell immunity induced by adjuvants mtrIL-33 and proIL-33 facilitated tumor regression.

Figure 9:
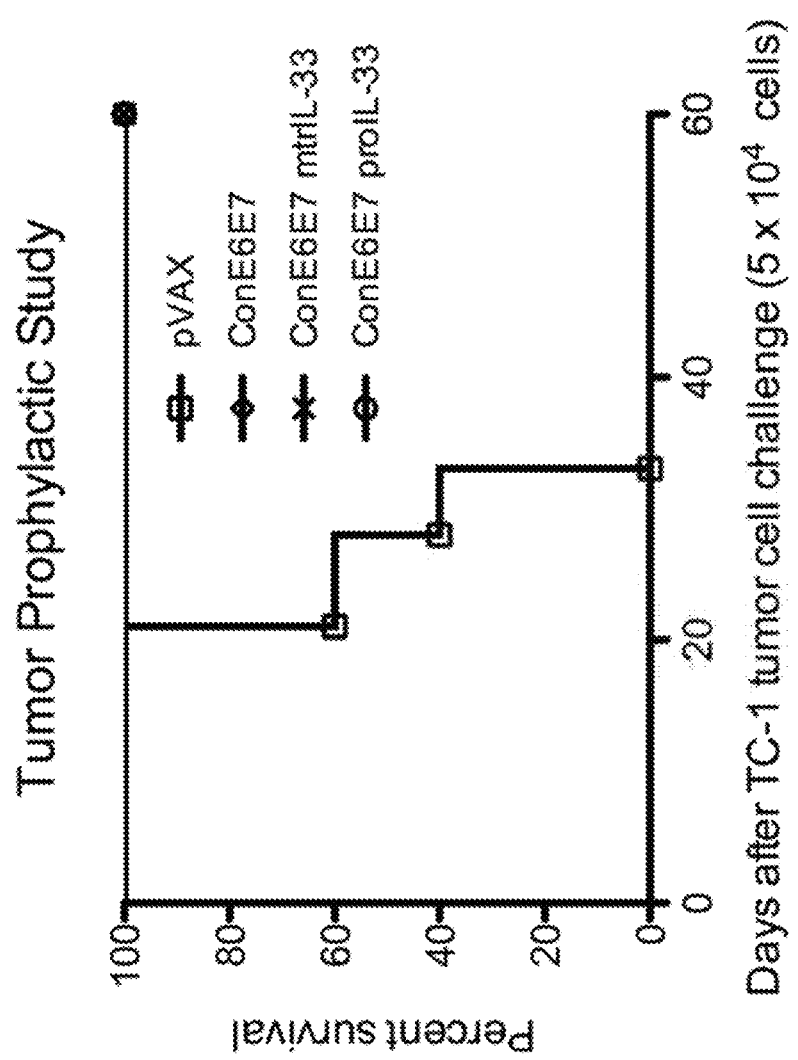
FIG. 9 shows the percent survival of mice after tumor cell challenge.

To examine protection or prophylaxis against new tumors or lesions, respective groups of B6 mice (10 mice per group) were immunized three times at three week intervals with pVAX, ConE6E7 construct alone, ConE6E7 construct with proIL-33 construct, and ConE6E7 construct with mtrIL-33 construct. Immunization with pVAX served as a negative control. The dosage of the mtrIL-33 and proIL-33 constructs was 7 µg. Mice were challenged with $5 \times 10^4$ TC-1 cells one week after the last immunization to assess the anti-tumor or prophylactic efficacy of the vaccines. As shown in FIG. 9, the vaccines prevented tumor growth upon implantation, but mice immunized with pVAX (the negative control) died within 40 days after implantation. Both proIL-33 and mtrIL-33 maintained and elicited anti-tumor memory responses similar to ConE6E7.

These data showed that ConE6E7 prevented E6/E7 tumor growth, but did not cause tumor regression as effectively as when mtrIL-33 or proIL-33 was an adjuvant in the vaccine. As an adjuvant in the vaccine, mtrIL-33 and proIL-33 prevented tumor growth and caused 90% and complete regression of established tumor, respectively. While only proIL-33 induced humoral immunity (i.e., increased IgG levels as described above), both mtrIL-33 and proIL-33 induced (increased) $CD4^+$ T cell immunity, $CD8^+$ T cell immunity, and cytolytic effector $CD8^+$ T cells undergoing degranulation. Accordingly, these data together indicated that because both mtrIL-33 and proIL-33 provided significant levels of tumor regression, the anti-tumor protection is afforded by the T cell immunity induced by inclusion of proIL-33 and mtrIL-33 as adjuvants in vaccines. In summary, the HPV-specific T cell immunity induced by the proIL-33 and mtrIL-33 adjuvants provided substantial protective anti-tumor immunity by delaying and rapidly inducing complete regression of established TC-1 tumors.

Example 11

Materials and Methods for Examples 12-15

Constructs.

The DNA construct encoding mature IL-33 (mtrIL-33) is described above in Example 1. The DNA constructs also included an HIV (ConC), LCMV-GP construct, and TB Ag85B construct. All constructs had highly efficient immunoglobulin E (IgE) leader sequence inserted at the 5' end of the gene. The constructs were synthesized and optimized.

Animals.

Female C57BL/6 ($H-2^b$) 8-week old mice were purchased from Jackson Laboratory (Bar Harbor, Me.).

Animal Immunizations and Anti-CD122 Treatment.

Mice were immunized once intramuscularly (i.m.) in the tibialis anterior muscle. In vivo electroporation (EP) was delivered with the CELLECTRA adaptive constant current EP device (Inovio Pharmaceuticals) at the same site immediately following vaccination.

The mice were immunized with either 10 μg pVAX1 or 10 μg pLCMV-NP with or without 11 μg of mtrIL-33 construct. Three weeks after the initial immunization, mice were sacrificed and splenocytes were harvested to measure immune responses.

The LCMV-GP (GP) construct was administered at 10 μg. Depletion of $CD122^+$ cells was achieved by s.c. injection of 20 μg of anti-CD122 monoclonal antibody (mAb) (AbD Serotec).

For the HIV and TB immunizations, mice were immunized three times at two-week intervals with 10 μg of each construct (ConC, Ag85B) with or without 11 μg of mtrIL-33. One week after immunization, the mice were sacrificed and splenocytes were harvested to monitor immune responses.

All studies were repeated at least two times.

LCMV Viral Challenge.

For lethal challenge studies, immunized mice were challenged i.c. 21 days after initial vaccination with either $20 \times LD_{50}$ or $40 \times LD_{50}$ of LCMV Armstrong in 30 μl of virus diluent (PBS with 20% FBS and 1× Anti-Anti (Invitrogen, Carlsbad, Calif.). All mice LCMV challenged were housed in a BSL-2 facility and were observed daily for 21 days.

ELISPOT Assay.

For mice vaccinated with DNA, all spleens were processed and IFN-γ ELISpot assays were performed to determine the antigen-specific cytokine secretion. Spleens were collected in RPMI 1640 medium (supplemented with 10% FBS, 1× Antibiotic-Antimycotic, and 1×β-ME) and splenocytes were isolated by mechanical disruption of the spleen using a Stomacher machine (Seward Laboratory Systems, Bohemia, N.Y.). The resulting mashed spleens were filtered using a 40 μm cell strainer, treated with ACK lysis buffer for 5 minutes to lyse the RBCs, washed in PBS and then resuspended in RPMI medium for use in ELISpot or Flow Cytometry assay.

The measurement of LCMV-specific T cell responses were assessed by stimulating splenocytes with immunodominant LCMV epitope from the $H-2^b$ background ($D^bNP_{306-404}$ (NP396)) or ($DbGP_{33-41}$ (GP33)) (Invitrogen). The HIV-specific T cell responses were measured by using pooled peptides (15-mers overlapping by 9 amino acids; 2.5 μg/ml final). The Ag85B-specific T cell responses were measured by using pooled peptides (11-mers overlapping by 8 amino acids; 2.5 μg/ml final) spanning the entire TB Ag85B antigen. All peptides were synthesized from GenScript. Concavalin A (Sigma-Aldrich, St. Louis, Mo.) was used as positive control and complete culture medium was used as negative control. Spots were enumerated using an automated ELISPOT reader (Cellular Technology, Shaker Heights, Ohio).

Flow Cytometry.

Lymphocytes were isolated and processed from the peripheral blood. Cells were stained with CD8, CD44, CD62L, KLRG1, CD122 and MHC class I peptide tetramer to LCMV-GP33 (KAVYNFATC (SEQ ID NO:9)) (Beckman Coulter). Intracellular cytokine staining was performed after 5 hours (hr) of ex vivo stimulation with either LCMV epitope $D^bNP_{396-404}$ or $D^bGP_{33-41}$ peptide, HIV pooled peptides, and Ag85B pooled peptides depending on the study.

The following antibodies were used for surface staining: LIVE/DEAD Fixable Violet Dead Cell stain kit (Invitrogen), CD4 (FITC; clone RM4-5; ebioscience), CD8 (APC-Cy7; clone 53-6.7; BD Biosciences); CD44 (A700; clone IM7; Biolegend). For intracellular staining, the following antibodies were used: IFN-γ (APC; clone XMG1.2; Biolegend), TNF-α (PE; clone MP6-XT22; ebioscience), CD3 (PerCP/Cy5.5; clone 145-2C11; Biolegend); IL-2 (PeCy7; clone JES6-SH4; ebioscience).

All data was collected using a LSRII flow cytometer (BD Biosciences) and analyzed using FlowJo software (Tree Star, Ashland, Oreg.) and SPICE v5.2 (available from the National Institutes of Health (NIH), specifically, the National Institutes of Allergy and Infectious Disease (NIAID)). Boolean gating was performed using FlowJo software to examine the polyfunctionality of the T cells from vaccinated animals.

T Cell Proliferation Assay.

Splenocytes isolated from immunized B6 mice 21 days after initial immunization were labeled with Cell Tracer violet Violet (Molecular Probes) and pulsed with 10 μM peptide for 5 days. CD8 T cell proliferation was determined using flow cytometry to assess Cell Trace Violet dilution.

Statistical Analysis.

Group analyses were completed by matched, two-tailed, unpaired t-test and survival curves were analyzed by log-rank Mantel-Cox test. For non-equally distributed samples, nonparametric Mann-Whitney test was performed (FIGS. 12E and 12F). All values are mean±SEM and statistical analyses were performed by GraphPad Prism (La Jolla, Calif.).

Example 12

IL-33 Elicited Protection Against a Lethal LCMV Challenge

As described above, IL-33 induced both anti-viral and anti-tumor $CD8^+$ T cell responses when administered in a vaccine, and thus, IL-33 served as an adjuvant in this vaccine. To further study the protection afforded by IL-33, when present in a vaccine, the LCMV infection model (also known herein as the "i.c. LCMV challenge model") was used. The LCMV infection model was a model for virus-specific CD8+ T cell responses in the context of vaccine-elicited protection. The LCMV NP structural protein was a component and target for protective LCMV immunity because it was not a target for neutralizing antibodies.

In particular, three groups of C57BL/6 mice (B6) (n=10/group) were vaccinated by electroporation (EP) one time intramuscular (i.m.) with 10 µg of empty vector control plasmid (pVAX) or 10 µg pLCMV-NP (NP) construct with or without 11 µg of mature IL-33 (mtrIL-33) construct. The empty vector pVAX was used as a negative control.

Figure 11:
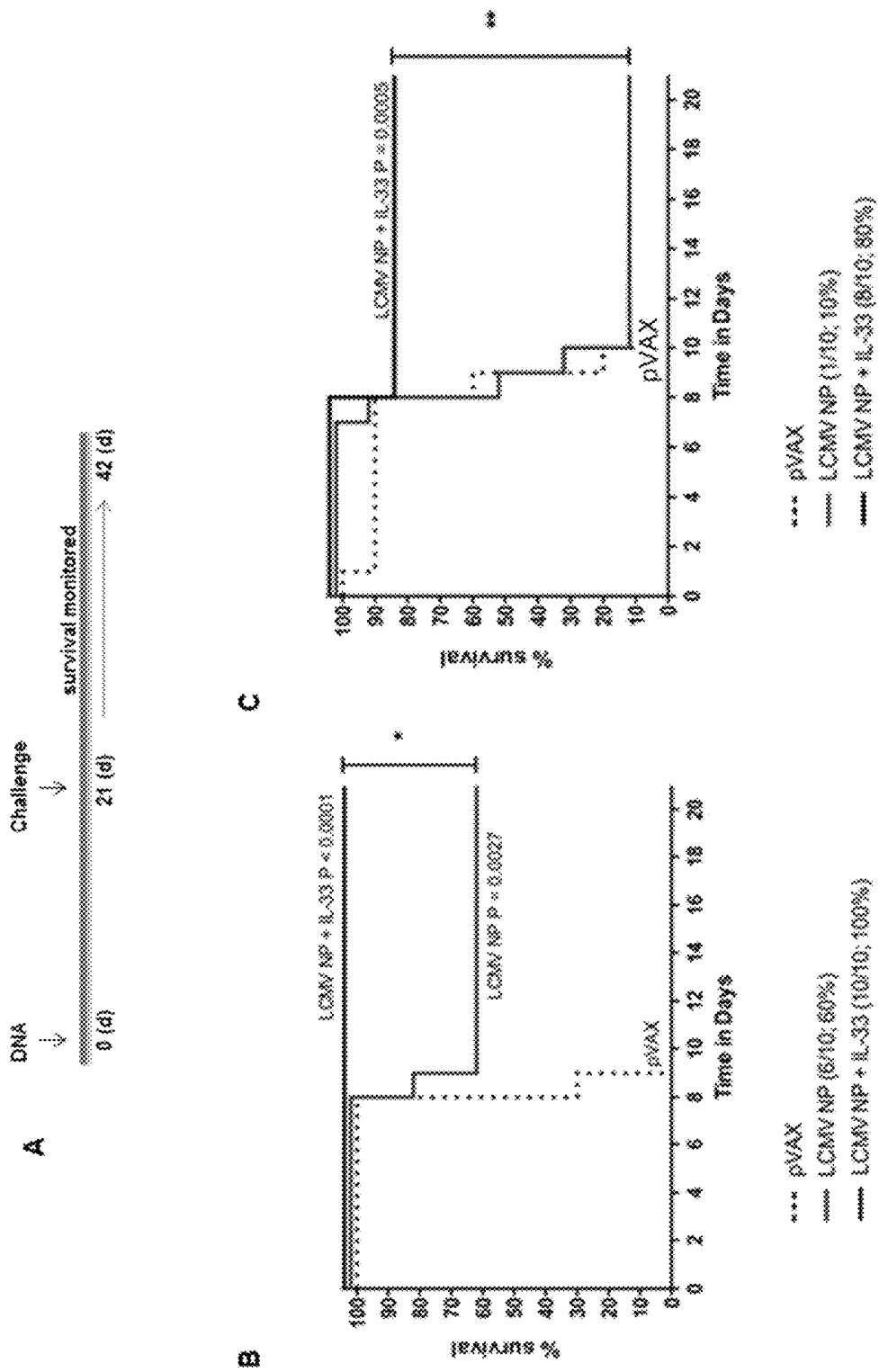
FIG. 11 shows in (A) a schematic illustration of the timeline for experiments examining LCMV challenge; (B) percent survival of mice challenged i.c. with 20×LD$_{50}$ Armstrong LCMV; and (C) percent survival of mice challenged i.c. with 40×LD$_{50}$ Armstrong LCMV.

All animals were challenged 21 days post-vaccination (dpv) i.c. with a lethal 20×LD$_{50}$ dose or a lethal 40×LD$_{50}$ of LCMV Armstrong (FIG. 11A). Animal survival was monitored 21 days post challenge. Experiments were performed at least two times in independent experiments and the data shown in FIG. 11 were representative of the result.

Vaccinated animals with NP plus mtrIL-33 showed complete protection while the NP alone group achieved only 60% protection (FIG. 11B). In FIG. 11B, *<0.05. In contrast, all control pVAX vaccinated animals succumbed to infection. Accordingly, these data showed that mice immunized with the vaccine using mtrIL-33 as an adjuvant exhibited 100% survival rate to LCMV challenge.

Further studies were completed to determine whether vaccinated mice, which had received the mtrIL-33 adjuvant, would be protected against an even higher lethal dose of LCMV challenge. Therefore, mice where challenged with a 40×LD$_{50}$ dose of LCMV Armstrong, 21 days post-single vaccination (FIG. 11C). Animals receiving one immunization of NP plus mtrIL-33 yielded a significant 80% protection, while the NP alone group only conferred 10% protection against this highly lethal dose of LCMV (FIG. 11C). In FIG. 11C, **<0.01.

In summary, the above data showed that IL-33, when included in the vaccine, elicited protection against a lethal LCMV challenge.

Example 13

IL-33 Increased LCMV-Specific CD8+ T Cell Responses

Figure 12:
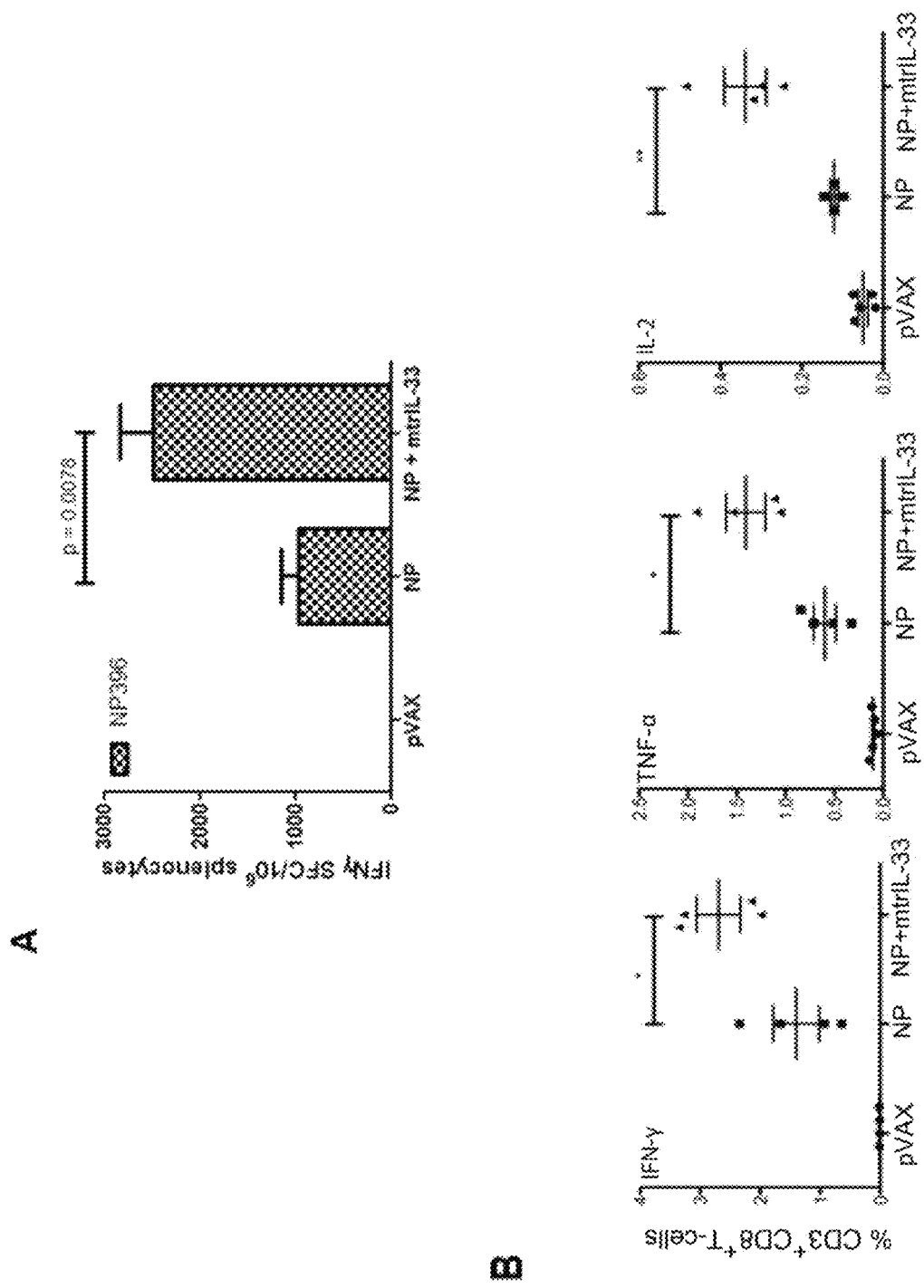
FIG. 12 shows in (A) the ability of CD8$^+$ T cells to produce IFN-γ in response to the D$^b$NP396 epitope as determined by IFN-γ ELISpot assay; (B) the total cytokine (i.e., IFN-γ, TNF-α, and IL-2) frequencies of D$^b$NP396-specific CD8$^+$ T cells as measured by flow cytometry; (C) subpopulations of single-, double-, and triple-positive CD8$^+$ T cells releasing the cytokines IFN-γ, TNF-α, and IL-2; (D) the percentage of antigen-specific cytolytic, degranulation T cells producing IFN-γ, in which degranulation T cells were identified by the degranulation marker CD107a and dot plots were representative of each mouse group; (E) the percent proliferation of CD8$^+$ T cells stimulated with D$^b$NP396 peptide, anti-CD3, and anti-CD28 as measured by cell tracer violet and flow cytometry; and (F) the percent proliferation of effector-memory CD8$^+$ T cells upon stimulation with D$^b$NP396 peptide, in which the dot plots were representative of CD62L$^-$CD44$^+$CD8$^+$ T cells after stimulation.

To determine if the above-described protection against LCMV challenge was mediated by the induction of CD8+ T cells, antigen-specific T cell responses were examined by the ELISPOT assay in immunized mice. In particular, groups of C57BL/6 mice (n=4-5) were immunized i.m. once with 10 µg nucleoprotein (NP) either with or without 11 µg mtrIL-33 followed by electroporation. Mice that received only 10 µg pVAX served as a negative control. Splenocytes were harvested 21 days post vaccination to assess the cellular immune responses. Specifically, the magnitude of NP-specific immune responses was measured 21 days post vaccination (dpv) in response to peptide re-stimulation using the immunodominant epitope in the H-2$^b$ background: D$^b$NP$_{396-40}$ (NP396). The results of these experiments are shown in FIG. 12 as described in more detail below. In FIG. 12, data was shown as the standard error of the mean (SEM) of two independent experiments repeated at least two to three times. In FIG. 12, *, P<0.05; , P<0.01; and *, P<0.001 compared with NP.

Compared to NP alone-vaccinated mice, co-immunization with mtrIL-33-encoding plasmid elicited stronger NP-specific T cell responses by greater than 2.5 fold (FIG. 12A). IFN-γ ELISPOT counts were about 2,500 spot-forming cells (SFCs) per 10$^6$ splenocytes in the IL-33 vaccinated mice versus about 980 SFC/10$^6$ spenocytes for the NP alone group.

The phenotypic and functional profile of vaccine-induced CD8+ T cells in response to NP396 peptide re-stimulation was also assessed. Twenty-one days after vaccination, a significant difference among vaccine groups in the frequency of CD8+ T cells producing effector cytokines was observed (FIGS. 12B and 12C). The NP vaccine co-administered with mtrIL-33 elicited a higher percentage of antigen (Ag)-specific CD8+ T cells producing all three cytokines (i.e., interferon-gamma (IFN-γ), tumor necrosis factor-alpha (TNF-α), and interleukin-2 (IL-2) (FIG. 12B), and a significant number of these CD8+ T cells were polyfunctional (FIG. 12C). Compared with the NP alone vaccinated group, the NP+mtrIL-33 vaccinated group elicited substantially higher frequencies of NP-specific CD8+ T cells producing either IFN-γ alone (NP, 1.3%; NP+mtrIL-33, 2.3%), dual IFN-γ+ TNF-α+ (NP, 0.76%; NP+mtrIL-33, 1.63%), or triple-positive IFN-γ+ TNF-α+IL-2+ (NP, 0.20%; NP+mtrIL-33, 0.43%) in the spleens 21 dpv (FIG. 12C). Collectively, the enhanced Ag-specific CD8+ T cell response induced by IL-33 was indicative of the ability of IL-33 to provide substantial protection against LCMV challenge.

The cytotoxic potential of vaccine-induced CD8+ T cells was also examined in these studies. CD8+ T cells isolated from mice vaccinated with mtrIL-33 showed a significantly higher frequency of antigen-specific (IFN-γ+CD107a+: 2.5%) degranulation compared to NP alone-vaccinated mice (IFN-γ+CD107a+: 1.2%) (FIG. 12D).

Additionally, the proliferative capacity of the CD8+ T cells was evaluated by monitoring Cell Trace Violet dilution in splenocytes isolated from mice 21 dpv and re-challenged in vitro with NP396 peptide re-stimulation. FIG. 12E shows that mtrIL-33 vaccinated mice underwent significantly higher Ag-specific proliferation of CD8+ T cells, being about 2 fold greater than NP control group. There was also an enrichment of effector memory CD8+ T cells (CD44+ CD62L−) in the adjuvant-vaccinated group (FIG. 12F). Taken together, the inclusion of mtrIL-33 elicited robust levels of NP-specific T cell immunity and enhanced enhancing CD8+ T cell immune responses.

Figure 13:
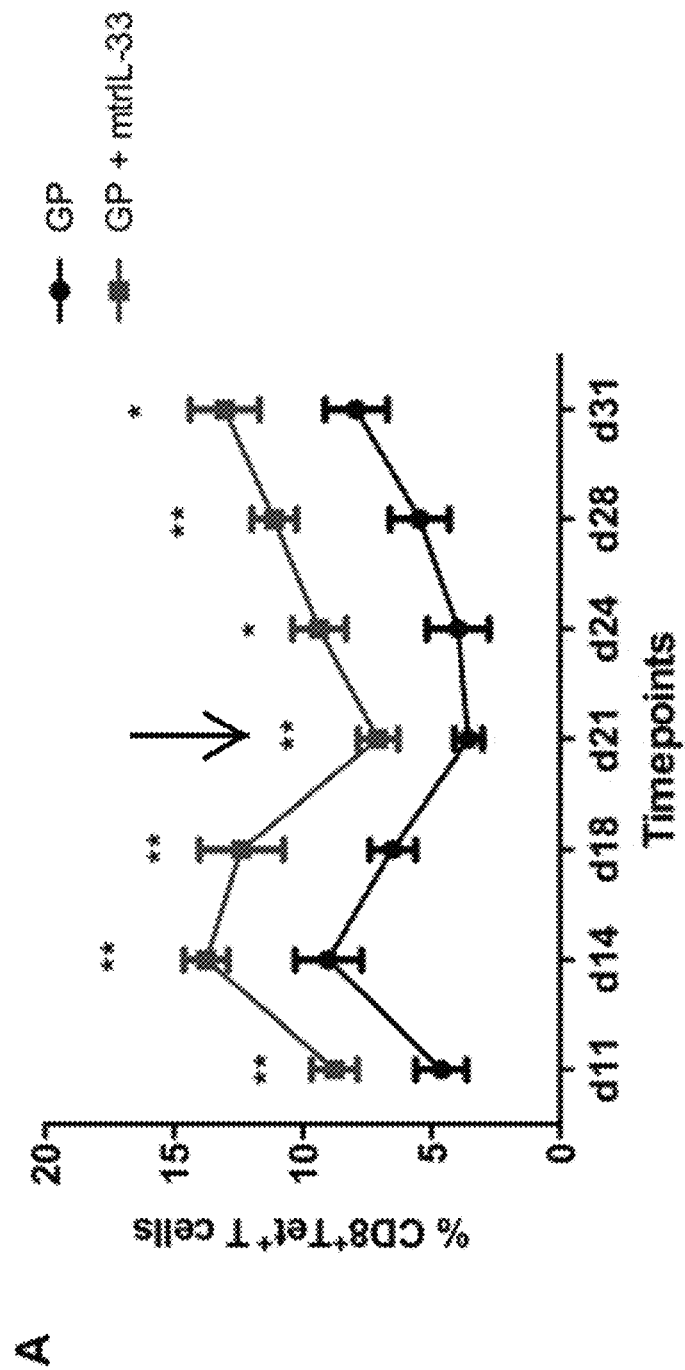
FIG. 13 shows in (A) the kinetics of D$^b$Gp33 (Tet$^+$)-specific CD8 T cells in the blood following DNA vaccination with a prime at day 0 and a boost with GP alone (arrow) on day 21 post vaccination (dpv); (B) the frequency of D$^b$GP33 CD8$^+$ T cells at 21 dpv; (C) GP-specific T cells producing IFN-γ on 21 dpv as measured by IFN-γ ELISpot assay; (D) the frequency of GP-specific IFN-γ$^+$CD8$^+$ T cells at 21 dpv; (E) the frequency of GP-specific CD107a$^+$CD8$^+$ T cells at 21 dpv; and (F) the frequency of GP-specific T-bet$^+$CD8$^+$ T cells at 21 dpv.

To further examine the induction of Ag-specific CD8+ T cells during the course of vaccination, the ability of mtrIL-33 to expand the Ag-specific effector memory CD8+ T cell population was studied. In these studies, the D$^b$GP$_{33-41}$ MHC class I tetramer was employed to follow Ag-specific CD8+ T cells as they developed after initial priming. In particular, C57BL/6 mice (n=4-8) were vaccinated once with 10 µg of a LCMV glycoprotein LCMV-GP (GP) DNA vaccine with or without mtrIL-33. The antigen-specific CD8 T cell population was monitored during the course of vaccination. In particular, the frequency of D$^b$GP33-specific CD8+ T cells was monitored in the peripheral blood during the course of vaccination either with or without mtrIL-33 (FIG. 14A). At day 21, spleens (n=4) were harvested and antigen-specific responses were monitored ex vivo with GP33 peptide. The results of these experiments are shown in FIG. 13 as described below in more detail. In FIG. 13, the data was shown as the SEM of two independent experiments repeated at least two times. In FIG. 13, *, P<0.05 and **, P<0.01.

Inclusion of mtrIL-33 in the vaccine resulted in an expansion of the number of $D^bGP33$ tetramer-specific CD8$^+$ T cells in the peripheral blood (FIG. 13A). In FIG. 13A, the cells were gated on live CD9$^+$CD44$^+$ T cells. In peripheral blood lymphocytes (PBLs), the frequency of GP33-specific CD8$^+$ T cells was 2-fold higher at 18 and 21 dpv compared with the nonadjuvanted group (FIG. 13A). The inclusion of mtrIL-33 in the vaccine also increased the number of GP33-specific CD8$^+$ T cells in the spleen 21 dpv (FIG. 13B) and Ag-specific CD8$^+$ T cells secreting IFN-γ, undergoing degranulation, and expressing the transcription factor T-bet (FIGS. 13C, 13D, 13E, and 13F).

Additionally, all mice were boosted with the GP construct alone (21 days after initial immunization) to quantify the Ag-specific recall responses. Compared to the control group, the mtrIL-33 vaccinated group significantly increased the Ag-specific CD8$^+$ T cells. In the mtrIL-33 immunized group, GP33 tetramer-specific T cells were about 3-fold higher starting 3 days post-boost vaccination (d24) compared to the NP-vaccinated group (FIG. 13A). This significant difference in the amplification of the GP33-specific CD8$^+$ T cells was still observed 10 days after DNA boost (d31). Consistent with FIG. 12, these data further confirmed the ability of IL-33 to induce rapid expansion and proliferation of Ag-specific CD8$^+$ T cells. Accordingly, IL-33 significantly increased LCMV-specific CD8$^+$ T cell immunity against two separate viral proteins, i.e., NP and GP.

In summary, the above data demonstrated that the frequency of the CD8$^+$ T cell response was significantly increased when mtrIL-33 was an adjuvant in the vaccine. This increased CD8$^+$ T cell response was antigen specific and resulted in increased production of the cytokines IFN-γ, TNF-α, and IL-2. Additionally, increased frequencies of polyfunctional CD8$^+$ T cells (i.e., IFN-γ$^+$ TNF-α$^+$ and IFN-γ$^+$ TNF-α$^+$IL-2$^+$) were observed when mtrIL-33 was an adjuvant in the vaccine. This increased CD8$^+$ T cell response also included a significantly higher frequency of antigen-specific degranulation when mtrIL-33 was an adjuvant in the vaccine. The above data also demonstrated that expansion of antigen-specific CD8$^+$ T cells, including effector-memory CD8$^+$ T cells, was increased when mtrIL-33 was an adjuvant in the vaccine. Together, these data further indicated the ability of mtrIL-33 to act as an effective adjuvant, namely by inducing CD8$^+$ T cell immunity.

Example 14

Figure 14:
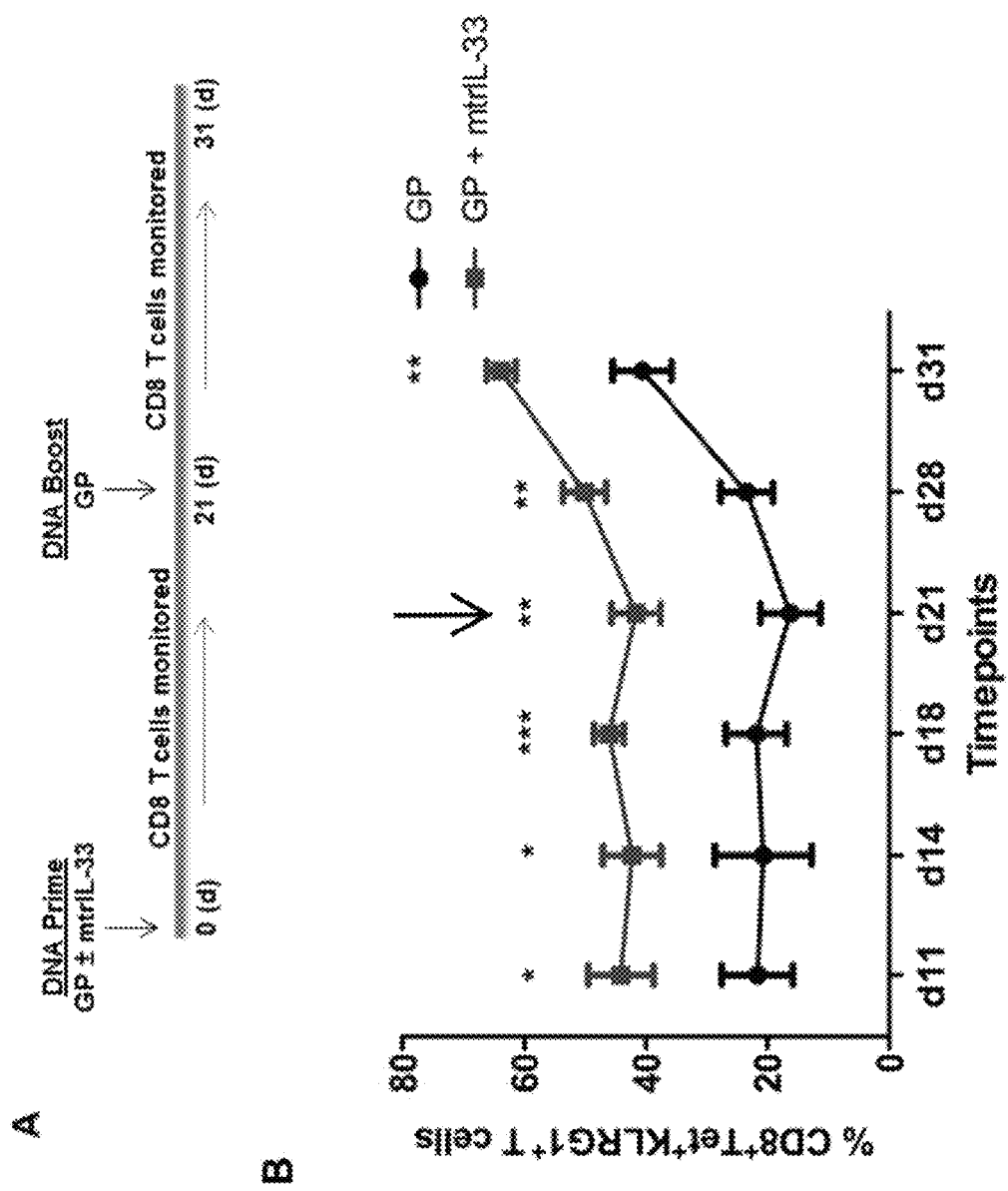
FIG. 14 shows in (A) a schematic illustrating a vaccine immunization schedule; and (B) the kinetics of the CD8$^+$ KLRG1$^+$ T cell population after DNA vaccination.
Figure 15:
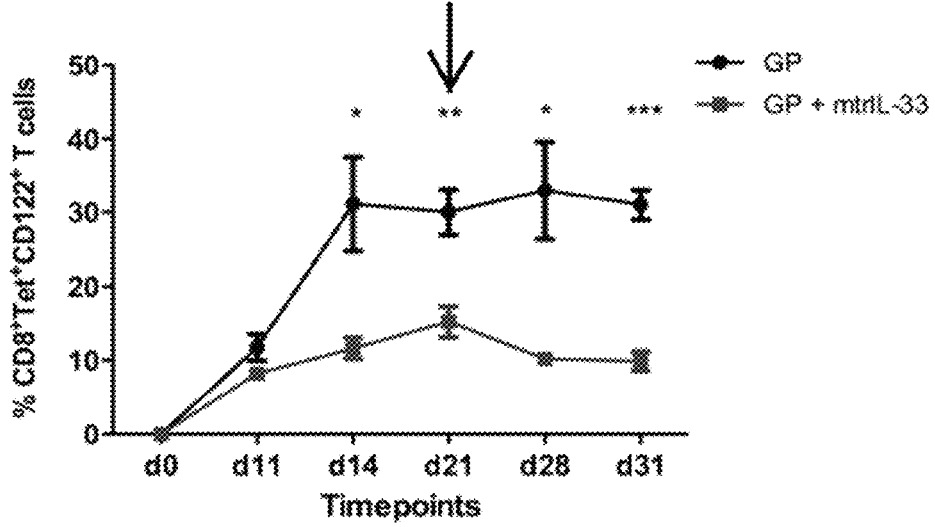
FIG. 15 shows in (A) the kinetics of D$^b$GP33$^+$CD8$^+$ CD122$^+$ T cell development after DNA vaccination with a prime at day 0 and a boost with GP-alone (arrow) at day 21 as well as representative contour plots indicating CD122 cell surface expression in D$^b$GP33$^+$ tetramer-specific CD8$^+$ T cells in peripheral blood on day 21 and day 31; (B) IFN-γ production by CD8$^+$CD122$^+$ T cells following re-stimulation ex vivo with GP antigen peptide pool on 21 dpv from harvested mice (n=4) spleens; and (C) representative IFN-γ production by CD8 T cell subsets (i.e., CD8$^+$KLRG1$^+$, CD8$^+$CD122$^+$, CD8$^+$KLRG1$^-$, and CD8$^+$CD122$^-$) following re-stimulation ex vivo with D$^b$NP396 peptide on 21 dpv from harvested mice spleens (n=4).
Figure 15:
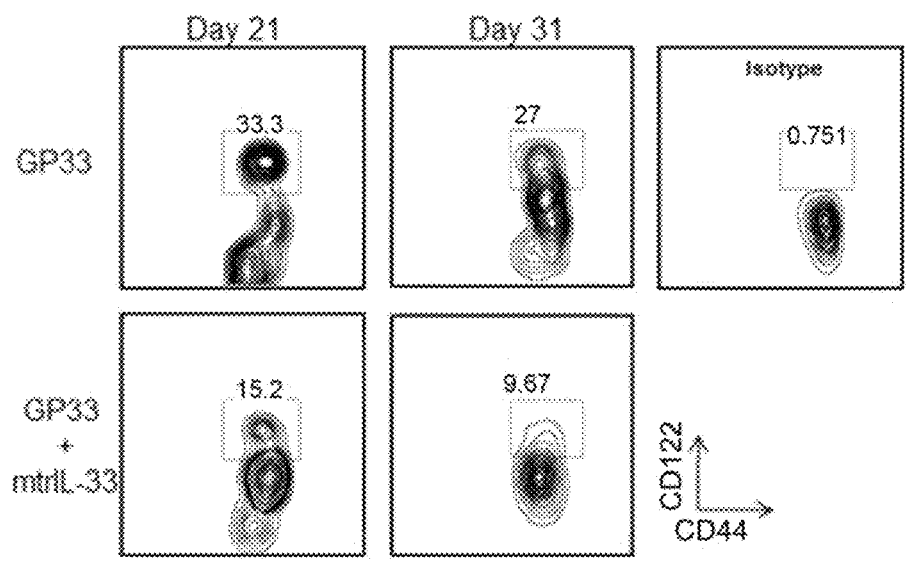

IL-33 Drove Effector-memory CD8$^+$KLRG1 T Cell Subset Differentiation and Prevented CD8$^+$CD122$^+$ Regulatory T Cell Expansion Protective immunity against invading pathogens may be mediated by memory CD8$^+$ T cells. Effector-phenotype memory T cells ($T_{eff}$) may mediate clearance of blood-borne pathogens. CD44 and KLRG1 are expression markers of $T_{eff}$ cell differentiation, and thus, are expressed on activated and memory CD8$^+$ T cells, but not naïve CD8$^+$ T cells. As described above, inclusion of IL-33 in the vaccine induced expansion and proliferation of antigen-specific CD8$^+$ T cells. As detailed below, studies were conducted to examine the ability of IL-33 to promote memory differentiation in the Ag-specific CD8+ T cell subsets induced during the course of vaccination (FIGS. 14 and 15). In particular, the markers CD44 and KLRG1 were first examined to determine if inclusion of IL-33 in the vaccine induced differentiation of $T_{eff}$ cells (FIG. 14A).

C57BL/6 mice (n=4-8) were immunized once with 10 μg of GP plasmid with or without 11 μg of mtrIL-33 construct and were boosted with only GP at 21 days after initial vaccination. Antigen-specific responses in the blood were monitored as indicated in FIG. 14A. In FIG. 14, experiments were repeated two times. In FIG. 14, *, $P<0.05$; , $P<0.01$; and *, $P<0.001$.

The administration of mtrIL-33 resulted in a significant expansion in the percentages of CD8$^+$KLRG1$^+$ $T_{eff}$ cells in the PBLs compared with the GP-only vaccinated group (FIG. 14B). In FIG. 14B, the population was gated on $D^bGp33^+$CD8$^+$CD44$^+$KLRG1$^+$. The recall response of $D^bGP33$ tetramer-specific CD8$^+$KLRG1$^+$ T cells after DNA-GP boosting was also evaluated 21 days after initial immunization. Marked expansion of GP33-specific memory CD8$^+$KLRG1$^+$ T cells in both groups was observed after boosting; however, the proportion of CD8$^+$KLRG1$^+$ T cells remained significantly higher in the mtrIL-33 adjuvant group (FIG. 14B).

The ability of mtrIL-33 to alter the differentiation of the CD8$^+$CD122$^+$ T cell subset population was examined because this population may have a regulatory function and suppress vaccine-induced immune responses. As such, the expansion of such a CD8$^+$ T cell suppressor population may be a drawback to vaccination strategies.

The kinetics of the vaccine-induced $D^bGP33^+$CD8$^+$CD122$^+$ specific T cell subset during the course of vaccination in PBLs revealed a striking difference (FIG. 15A). GP-only vaccinated mice induced higher $D^bGP33$ tetramer-specific CD8$^+$CD122$^+$ T cell responses during the course of vaccination compared to the GP+mtrIL-33-treated group. Each group had 4-8 mice. The frequency of GP33-specific CD8$^+$CD122$^+$ T cells in GP-group was about 3-fold higher starting at 14 dpv compared to the mtrIL-33 treated group (FIG. 15A). The inclusion of mtrIL-33 in the vaccine maintained relatively constant low levels of tetramer-specific CD8$^+$CD122$^+$ T cell subset over the course of vaccination. As such, inclusion of mtrIL-33 in the vaccine suppressed expansion of CD122$^+$CD8$^+$ regulatory T cells, which in turn, increased the immune response induced by the vaccine.

In FIG. 15, the data shown were the results of three independent experiments repeated twice. In FIG. 15, *, $P<0.05$; , $P<0.01$; and *, $P<0.001$.

Figure 16:
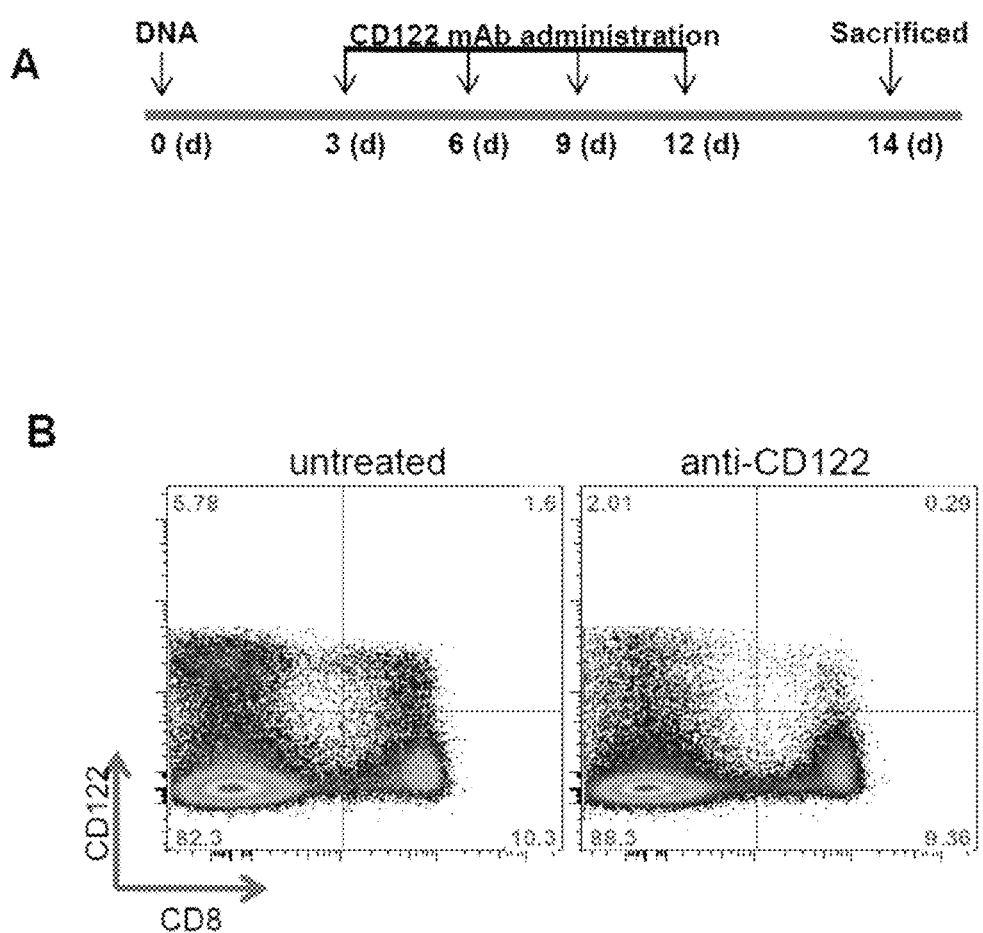
FIG. 16 shows in (A) a schematic of the immunization schedule of delivery of the DNA vaccine with anti-CD122 mAb; (B) an assessment of T cells expressing CD8 and CD122 in untreated and anti-CD122 treated mice; and (C) the frequency of D$^b$GP33 tetramer-specific CD8$^+$ T cells in the spleen after anti-CD122 mAb treatment and representative contour plots depicting D$^b$GP33 CD8$^+$ T cells after treatment.

When the functionality of this GP-specific CD8$^+$CD122$^+$ T cell subset was examined 21 dpv in the spleen, the Ag-specific CD8$^+$CD122$^+$ T cells were not capable of producing IFN-γ (FIG. 15B) upon GP33 peptide re-stimulation. Similarly, the NP-specific CD8$^+$CD122$^+$ T cells secreted very little IFN-γ compared to the NP-specific CD8$^+$KLRG1$^+$ T cell subset or other uncharacterized Ag-specific CD8$^+$ T cells (FIG. 15C). As such, NP-specific CD8$^+$KLRG1$^+$ T cells induced IFN-γ, but not CD8$^+$CD122$^+$ regulatory T cells. Accordingly, the inclusion of mtrIL-33 in the vaccine significantly altered the CD8$^+$CD122$^+$ regulatory population. Therefore, the modulation of the CD8$^+$CD122$^+$ regulatory population was one mechanism by which mtrIL-33 increased vaccine-induced CD8$^+$ T cell responses To further examine this modulation, studies were conducted to determine whether depletion of CD8$^+$CD122$^+$ regulatory T cells would enhance the Ag-specific responses in the GP vaccinated group similar to the administration of mtrIL-33. In particular, two groups of C57BL/6 mice (n=4 per group) were vaccinated with DNA encoding GP antigen alone. Anti-CD122 monoclonal antibody (mAb) (20 μg) was injected intraperitoneal (i.p.) into one group of mice on days 3, 6, 9 and 12 post-single vaccination (FIG. 16A). The anti-CD122 mAb was used to deplete CD122. The other group of mice did not receive the anti-CD122 mAb and thus, served as a control. Mice were sacrificed at 14 dpv and spleens were harvested to assess for the expression of CD8 and CD122. The results of these experiments are shown in FIG. 16 and described below in more detail. In FIG. 16, data were shown as the results of one representative out of two.

CD122 depletion resulted in elimination of the CD8+CD122+ T cells in mice treated with anti-CD122 mAb (FIG. 16B). At week 2 after vaccination, the CD122-depleted mice exhibited a pronounced increase in the number of $D^bGP33^+$-specific CD8+ T cells in the spleen compared with Ag-specific CD8+ T cells in the control group (FIG. 16C). As such, depletion of CD8+CD122+ regulatory T cells by in vivo administration of anti-CD122 mAb resulted in an increase in vaccine-induced immune responses similar to the co-administration of mtrIL-33 adjuvant as shown in FIG. 13.

In summary, these data indicated the ability of mtrIL-33 to prevent the differentiation or expansion of these regulatory T cells, i.e., the CD8+CD122+ T cell subset. Such a reduction was another mechanism by which mtrIL-33 facilitated anti-viral immunity.

Examples 12, 13, and 14 demonstrated that the co-administration of mtrIL-33 construct not only increased the magnitude of IFN-γ spot-forming NP396-specific CD8+ T cells, but also improved their polyfunctionality, increased the cytolytic phenotype of the CD8+ T cells, and their effector memory differentiation. As measured by IFN-γ ELISpot for the specific CD8 T cell epitope $D^bNP396-40$, the inclusion of mtrIL-33 induced a 2.5-fold greater response compared to NP-alone immunization. Furthermore, these examples showed that mtrIL-33 enhanced the polyfunctional CD8+ T cell populations secreting IFN-γ+TNF-α+IL2+, IFN-γ+ TNF-α+ and IFN-γ+ and elicited a greater Ag-specific CD8+ cytolytic degranulation (FIG. 12). This data was in accordance with the studies of Examples 1-10 that IL-33 (both of the proIL-33 and mtrIL-33 forms) increased the Ag-specific cell-mediated immune response when co-administered with a DNA vaccine.

Further in accordance with the studies of Examples 1-10, it was demonstrated in the studies of examples 12-14 that mtrIL-33, like proIL-33, induced significant amplification of GP33+CD8+ T cell responses in the blood in response to vaccination. As such, IL-33 modulated the expansion of CD8+ T cells.

These studies of examples 12-14 also demonstrated that secondary recall responses after boost elicited rapid expansion of tetramer-specific CD8+KLRG1+ T cells as compared to the GP-alone vaccinated group (FIG. 13A). This difference and rapid recall response of the Ag-specific effector memory CD8+ T cells 8 days after boosting agreed with the ability of IL-33 to provide an adjuvant effect and mediate antiviral protection as shown in FIG. 11. Overall, these results demonstrated that inclusion of IL-33 as an adjuvant promoted antiviral immunity by inducing effector-memory T cells that initiated immediate effector function.

Additionally, these examples demonstrated that depletion of the CD8+CD122+ regulatory T cells increased the tetramer-specific CD8+ T cell responses (FIG. 16C), which indicated that the increase in Ag-specific CD8+ T cell expansion and function in IL-33 vaccinated mice was related to the prevention of the expansion of CD8+CD122+ regulatory T cells.

Example 15

IL-33 Augmented HIV- and TB-Specific T Cell-Mediated Responses

Figure 17:
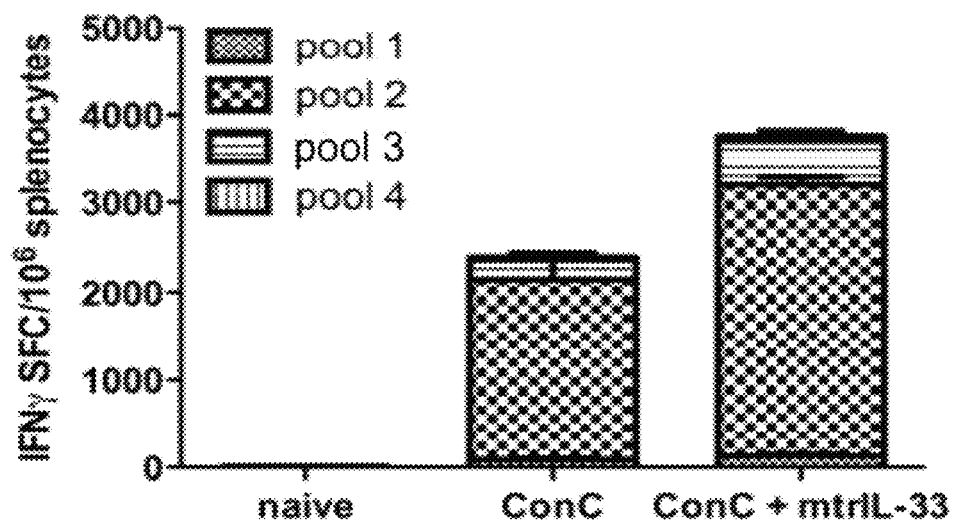
FIG. 17 shows in (A) detection of antigen-specific cells secreting IFN-γ after vaccination as measured by IFN-γ ELISpot assay; (B) the percentage of polyfunctional CD4$^+$ T cells as determined by multi-parameter flow cytometry, in which the bar chart depicted the percentage of HIV-specific T cells displayed as triple-, double-, and single-positive cells secreting cytokines IFN-γ, IL-2, and TNF-α, and the pie chart depicted the relative proportion of each cytokine subpopulation; and (C) the percentage of polyfunctional CD8$^+$ T cells as determined by multi-parameter flow cytometry, in which the bar chart depicted the percentage of HIV-specific T cells displayed as triple-, double-, and single-positive cells secreting cytokines IFN-γ, IL-2, and TNF-α, and the pie chart depicted the relative proportion of each cytokine subpopulation.
Figure 18:
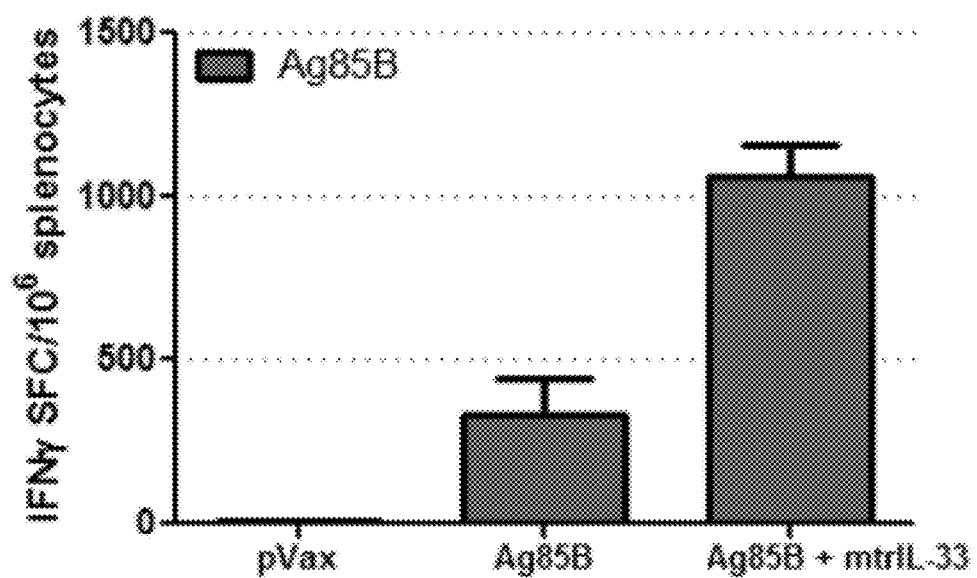
FIG. 18 shows in (A) detection of antigen-specific cells secreting IFN-γ after vaccination as measured by IFN-γ ELISpot assay; (B) the percentage of polyfunctional CD4$^+$ T cells as determined by multi-parameter flow cytometry, in which the bar chart depicted the percentage of TB-specific T cells displayed as triple-, double-, and single-positive cells secreting cytokines IFN-γ, IL-2, and TNF-α, and the pie chart depicted the relative proportion of each cytokine subpopulation; and (C) the percentage of polyfunctional CD8$^+$ T cells as determined by multi-parameter flow cytometry, in which the bar chart depicted the percentage of TB-specific T cells displayed as triple-, double-, and single-positive cells secreting cytokines IFN-γ, IL-2, and TNF-α, and the pie chart depicted the relative proportion of each cytokine subpopulation.

To determine whether mtrIL-33 adjuvant enhanced the vaccine potency for other pathogens requiring both $T_H1$ and CD8+ T cell responses, the Ag-specific T cell-mediated responses of mtrIL-33 co-delivered with a HIV or a TB DNA antigen was assessed (FIGS. 17 and 18). C57BL/6 mice (n=4-5) were vaccinated three times intramuscular (i.m.) at two week intervals with 10 μg of either HIV Consensus Glade C (ConC) or TB Antigen 85B (Ag85B) given alone or in combination with 11 μg of mtrIL-33 followed by EP. One week after final immunization, mice were sacrificed and spleens were processed. Antigen-specific immune responses were measured using cells derived from these spleens.

Consistent with findings in the LCMV model (FIGS. 12A, 12B, and 12C), the inclusion of mtrIL-33 in the vaccine enhanced the numbers of HIV- and TB-specific IFN-γ secreting T cells (ConC, about 3,800 SFC; Ag85B, about 1,062 SFC) when compared with nonadjuvanted groups (ConC, about 2,300 SFC; Ag85B, about 333 SFC), respectively (FIGS. 17A and 18A).

In FIG. 17, experiments were performed at least two times with similar results. Also in FIG. 17, *, P<0.05; , P<0.01; and *, P<0.001 compared with ConC group. In FIG. 18, experiments were performed at least two times with similar results. Also in FIG. 18, *, P<0.05; and **, P<0.01 compared with Ag85B group.

Furthermore, the cytokine-producing phenotype of the CD4+ and CD8+ T cell population after immunization was examined for both of the HIV and TB antigens (FIGS. 17B and 17C, and 18B and 18C, respectively). In mice, the Ag-specific $T_H1$ response after both of the HIV and TB vaccinations consisted of a high frequency of polyfunctional triple-positive (IFN-γ+ TNF-α+IL-2+), double-positive (IFN-γ+ TNF-α+), and IFN-γ single-positive CD4+ T cells in the spleen (FIGS. 17B and 18B, respectively). Regarding CD8+ T cells, it was observed that the responses after HIV and TB vaccination with mtrIL-33 induced significantly higher frequency of polyfunctional double-positive (IFN-γ+ TNF-α+) and TNF-α- and IFN-γ-single-positive CD8+ T cells (FIGS. 17C and 18C, respectively). These data, along with the data from the above examples, indicated that IL-33 was an effective adjuvant in vaccines targeting different pathogens.

In summary, examples 12-15 demonstrated that co-administration of IL-33 during vaccination augmented the magnitude and function of antigen (Ag)-specific T cells against different antigens, for example, LCMV NP as well as HIV and TB antigens. These responses were characterized by higher frequencies of $T_H1$-type, polyfunctional T cells that exhibited cytotoxic phenotypes. These T cells were capable of robust expansion upon Ag-specific re-stimulation in vivo and protected against high dose lethal LCMV challenge. These T cells were also capable of robust antigen-specific IFN-γ production.

In addition, IL-33 modulated Ag-specific immunity by amplifying KLRG1+ effector memory T cells and preventing the expansion of CD122+ regulatory CD8+ T cells. In this manner, the adjuvant IL-33 improved the T cell immunity induced by vaccines.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A vaccine comprising:
   a) at least one selected from the group consisting of an antigen and a nucleotide sequence encoding an antigen; and
   b) a nucleotide sequence encoding interleukin-33 (IL-33), wherein the nucleotide sequence encoding IL-33 comprises a nucleotide sequence selected from the group consisting of: a nucleotide sequence having at least about 95% identity to a nucleotide sequence as set forth in SEQ ID NO:1, a nucleotide sequence as set forth in SEQ ID NO:1, a nucleotide sequence having at least about 95% identity to a nucleotide sequence as set forth in SEQ ID NO:3, and a nucleotide sequence as set forth in SEQ ID NO:3.

2. The vaccine of claim 1, wherein the nucleotide sequence encoding IL-33 comprises the nucleotide sequence as set forth in SEQ ID NO:1.

3. The vaccine of claim 1, wherein the nucleotide sequence encoding IL-33 comprises the nucleotide sequence as set forth in SEQ ID NO:3.

4. The vaccine of claim 1, wherein the antigen is encoded by a first nucleic acid and IL-33 is encoded by a second nucleic acid.

5. The vaccine of claim 4, further comprising an antigen peptide with the same encoded nucleic acid sequence as the antigen of claim 4, and an IL-33 peptide with the same encoded nucleic acid sequence as the IL-33 of claim 4.

6. The vaccine of claim 4, wherein the second nucleic acid further comprises an expression vector.

7. The vaccine of claim 1, wherein IL-33 is selected from the group consisting of full-length IL-33 (proIL-33) and mature IL-33 (mtrIL-33).

8. The vaccine of claim 7, wherein IL-33 is proIL-33.

9. The vaccine of claim 8, wherein proIL-33 is encoded by a nucleotide sequence as set forth in SEQ ID NO:3.

10. The vaccine of claim 7, wherein IL-33 is mtrIL-33.

11. The vaccine of claim 10, wherein mtrIL-33 is encoded by a nucleotide sequence as set forth in SEQ ID NO:1.

12. The vaccine of claim 1, wherein the antigen is selected from the group consisting of: a human papilloma virus (HPV) antigen, a fragment of an HPV antigen, an Human Immunodeficiency Virus (HIV) antigen, a fragment of an HIV antigen, an influenza antigen, a fragment of an influenza antigen, a *Plasmodium falciparum* antigen, a fragment of a *Plasmodium falciparum* antigen, a *Mycobacterium tuberculosis* antigen, a fragment of a *Mycobacterium tuberculosis* antigen, a lymphocytic choriomeningitis (LCMV) antigen, and a fragment of a LCMV antigen.

13. The vaccine of claim 12, wherein the HPV antigen is selected from the group consisting of: HPV16 E6 antigen, HPV16 E7 antigen, and a combination thereof.

14. The vaccine of claim 12, wherein the HIV antigen is selected from the group consisting of: Env A, Env B, Env C, Env D, B Nef-Rev, Gag, and any combination thereof.

15. The vaccine of claim 12, wherein the influenza antigen is selected from the group consisting of: H1 HA, H2 HA, H3 HA, H5 HA, BHA antigen, and any combination thereof.

16. The vaccine of claim 12, wherein the *Plasmodium falciparum* antigen includes a circumsporozoite (CS) antigen.

17. The vaccine of claim 12, wherein the *Mycobacterium tuberculosis* antigen is selected from the group consisting of: Ag85A, Ag85B, EsxA, EsxB, EsxC, EsxD, EsxE, EsxF, EsxH, EsxO, EsxQ, EsxR, EsxS, EsxT, EsxU, EsxV, EsxW, and any combination thereof.

18. The vaccine of claim 12, wherein the LCMV antigen is selected from the group consisting of: nucleoprotein (NP), glycoprotein (GP), and a combination thereof.

19. The vaccine of claim 1, further comprising a pharmaceutically acceptable excipient.

20. A nucleic acid molecule comprising one or more nucleotide sequences selected from the group consisting of: SEQ ID NO:1, SEQ ID NO:3, a nucleotide sequence that is 95% identical or greater to SEQ ID NO:1, a nucleotide sequence that is 95% identical or greater to SEQ ID NO:3, and any combination thereof.

21. The nucleic acid molecule of claim 20, wherein the nucleic acid molecule is a plasmid.

22. The nucleic acid molecule of claim 20, wherein the nucleic acid molecule is one or more plasmids.

* * * * *